(12) United States Patent
Al-Shafei et al.

(10) Patent No.: US 10,947,461 B2
(45) Date of Patent: Mar. 16, 2021

(54) SELECTIVE LIQUID-LIQUID EXTRACTION OF OXIDATIVE DESULFURIZATION REACTION PRODUCTS

(71) Applicant: Saudi Arabian Oil Company, Dhahran (SA)

(72) Inventors: Emad Naji Al-Shafei, Dhahran (SA); Esam Zaki Hamad, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/366,237

(22) Filed: Mar. 27, 2019

(65) Prior Publication Data
US 2019/0284487 A1    Sep. 19, 2019

Related U.S. Application Data

(60) Division of application No. 15/076,353, filed on Mar. 21, 2016, now abandoned, which is a continuation of
(Continued)

(51) Int. Cl.
*C10G 53/14* (2006.01)
*C10G 21/16* (2006.01)
(Continued)

(52) U.S. Cl.
CPC ............ *C10G 53/14* (2013.01); *C10G 21/16* (2013.01); *C10G 27/00* (2013.01); *C10G 27/12* (2013.01); *C10G 27/14* (2013.01); *C10G 29/20* (2013.01); *C10G 29/22* (2013.01); *C10G 29/28* (2013.01); *C10G 53/04* (2013.01); *G01N 33/287* (2013.01);
(Continued)

(58) Field of Classification Search
CPC ........ C10G 53/04; C10G 53/14; C10G 29/20; C10G 29/22; C10G 29/28; C10G 21/16; C10G 27/00; C10G 27/12; C10G 27/14
See application file for complete search history.

(56) References Cited

U.S. PATENT DOCUMENTS 2,749,284 A   6/1956 Noble
3,341,448 A   9/1967 Ford et al.
(Continued)

FOREIGN PATENT DOCUMENTS

EP    0 565 324 A1   10/1993

OTHER PUBLICATIONS

Hsun-Yi Huang et al., Per-acetic Acid Yield Optimization via Design of Experiments, Journal of Petroleum, Sep. 2010, vol. 46, No. 3, pp. 75-88 (Year: 2010).*
(Continued)

*Primary Examiner* — Prem C Singh
*Assistant Examiner* — Brandi M Doyle
(74) *Attorney, Agent, or Firm* — Abelman, Frayne and Schwab

(57) ABSTRACT

The present invention provides selective extraction of sulfoxides, or sulfoxides in combination with sulfones, from hydrocarbon mixtures containing these compounds. A significant advantage of the invention is that oxidation products resulting from oxidative desulfurization of hydrocarbon feedstocks are selectively extracted with minimum co-extraction of non-oxidized products such as valuable hydrocarbon fuel components.

11 Claims, 26 Drawing Sheets

Related U.S. Application Data application No. 13/627,606, filed on Sep. 26, 2012, now abandoned.

(60) Provisional application No. 61/539,734, filed on Sep. 27, 2011.

(51) Int. Cl.
| | |
|---|---|
| *C10G 27/00* | (2006.01) |
| *C10G 27/12* | (2006.01) |
| *C10G 27/14* | (2006.01) |
| *C10G 53/04* | (2006.01) |
| *C10G 29/20* | (2006.01) |
| *C10G 29/22* | (2006.01) |
| *C10G 29/28* | (2006.01) |
| *G01N 33/28* | (2006.01) |

(52) U.S. Cl.
CPC ... *C10G 2300/202* (2013.01); *C10G 2300/44* (2013.01); *C10G 2400/04* (2013.01)

(56) References Cited

U.S. PATENT DOCUMENTS

| | | | |
|---|---|---|---|
| 3,945,914 A | 3/1976 | Yoo et al. | |
| 3,981,887 A | 9/1976 | Gante et al. | |
| 4,502,988 A | 3/1985 | Hatfield | |
| 5,310,479 A * | 5/1994 | Audeh | C10G 27/12 208/219 |
| 5,621,097 A | 4/1997 | Brown et al. | |
| 5,731,423 A | 3/1998 | Kakarla et al. | |
| 5,753,102 A | 5/1998 | Funakoshi et al. | |
| 5,824,207 A | 10/1998 | Lyapin et al. | |
| 5,910,440 A | 6/1999 | Grossman et al. | |
| 5,958,224 A | 9/1999 | Ho et al. | |
| 6,013,761 A | 1/2000 | Zierer et al. | |
| 6,160,193 A | 12/2000 | Gore | |
| 6,277,271 B1 | 8/2001 | Kocal | |
| 6,402,939 B1 | 6/2002 | Yen et al. | |
| 6,402,940 B1 | 6/2002 | Rappas | |
| 6,638,419 B1 | 10/2003 | Da Silva et al. | |
| 6,673,236 B2 | 1/2004 | Stanciulescu et al. | |
| 7,001,504 B2 | 2/2006 | Schoonover | |
| 7,144,499 B2 | 12/2006 | Han et al. | |
| 7,314,545 B2 | 1/2008 | Karas et al. | |
| 2002/0035306 A1 | 3/2002 | Gore et al. | |
| 2003/0171589 A1 | 9/2003 | Oguma et al. | |
| 2004/0118750 A1 | 6/2004 | Gong et al. | |
| 2004/0154959 A1 | 8/2004 | Schoebrechts et al. | |
| 2004/0178121 A1 | 9/2004 | Leyshon et al. | |
| 2004/0222131 A1 | 11/2004 | Cullen | |
| 2005/0150819 A1 | 7/2005 | Wachs | |
| 2005/0189261 A1 | 9/2005 | Briot et al. | |
| 2006/0089386 A1 | 4/2006 | Parthasaradhi Reddy et al. | |
| 2006/0108263 A1 | 5/2006 | Lin et al. | |
| 2007/0051667 A1 * | 3/2007 | Martinie | C10G 27/00 208/208 R |
| 2007/0151901 A1 * | 7/2007 | Sain | C10G 21/20 208/208 R |
| 2008/0121565 A1 | 5/2008 | Yoo et al. | |
| 2009/0299100 A1 | 12/2009 | Ren et al. | |

OTHER PUBLICATIONS

Mohammad Amin Sobati, Liquid—liquid extraction of oxidized sulfur-containing compounds of non-hydrotreated kerosene, Fuel Processing Technology 91 (Year: 2010).*

Zannikos et al., Desulfurization of petroleum fractions by oxidation and solvent extraction, Fuel Processing Technology 42, pp. 35-45 (Year: 1995).*

International Search Report for PCT/US2012/057299 dated Feb. 8, 2013 (6 pages).

Perry's Chemical Engineers' Handbook, Chapter 15 Liquid-Liquid Extraction and Other Liquid-Liquid Operations and Equiptment (2008).

* cited by examiner

SELECTIVE LIQUID-LIQUID EXTRACTION OF OXIDATIVE DESULFURIZATION REACTION PRODUCTS

RELATED APPLICATIONS

This application is a Continuation of co-pending U.S. patent application Ser. No. 13/627,606 filed Sep. 26, 2012, which claims the benefit of U.S. Provisional Patent Application No. 61/539,734 filed Sep. 27, 2011, the disclosures of which are hereby incorporated by reference in its entirety.

BACKGROUND OF THE INVENTION

Field of the Invention

This invention relates to a system and process for extraction of sulfoxides or a combination of sulfoxides and sulfones, and more particularly to a selective liquid-liquid system and method for the extraction of oxidative desulfurization reaction products from a hydrocarbon mixture.

Description of Related Art

It is well known that certain sources of crude oil known as "sour" crude contain significant amounts of sulfur. If chemically-combined sulfur, such as organosulfur compounds, is not removed from the resultant hydrocarbon products, including paraffins, olefins and aromatics, particularly gasoline, diesel or other fuels, its presence can cause corrosion of processing equipment and engine parts, as well as other deleterious effects, particularly when water is present. Further, the discharge into the atmosphere of sulfur compounds during processing and end-use of the petroleum products derived from sour crude oil pose safety and environmental problems.

Conventional technologies such as hydrocracking and two-stage hydrotreating offer solutions to refiners for the production of clean transportation fuels that, to some extent, meet certain regulatory requirements. These technologies are available and can be applied when new production facilities are constructed. However, many existing hydroprocessing facilities, such as low pressure hydrotreaters, which represent substantial prior capital investment, were constructed before more stringent sulfur specifications were enacted. It is very difficult to upgrade existing hydroprocessing systems because of the comparably more severe operational requirements (i.e., higher temperature and pressure) to obtain clean fuel production. Available retrofitting options for refiners include elevating the hydrogen partial pressure by increasing the recycle gas quality, utilizing catalyst compositions having greater activity, installing improved reactor components to enhance liquid-solid contact, increasing reactor volume, and improving the feedstock quality. However, all retrofitting alternatives are limited by process economics and the basic existing hydrotreating system upon which they improve.

Sulfur-containing compounds that are typically present in hydrocarbon fuels include aliphatic molecules such as sulfides, disulfides and mercaptans as well as aromatic molecules such as thiophene, benzothiophene, dibenzothiophene (DBT), and alkyl derivatives such as 4,6-dimethyldibenzothiophene.

Among the sulfur-containing aromatic compounds, thiophenes and benzothiophenes are relatively easy to hydrodesulfurize. The addition of alkyl groups to the ring compounds increases the difficulty of hydrodesulfurization. Dibenzothiophenes resulting from addition of another ring to the benzothiophene family are even more difficult to desulfurize, and the difficulty varies greatly according to their alkyl substitution, with di-beta substitution being the most difficult to desulfurize, thus justifying their "refractory" appellation. These beta substituents hinder exposure of the heteroatom to the active site on the catalyst.

To keep pace with recent trends toward higher production of ultra-low sulfur fuels, i.e., having sulfur levels at or below 15 parts per million by weight (ppmw), refiners must choose among the processes or crude oils that provide flexibility to ensure that future specifications are met with minimum additional capital investment, in many instances by utilizing existing equipment.

The development of non-catalytic processes to carry out the final desulfurization of petroleum distillate feedstocks has been widely studied. Certain conventional approaches are based on oxidation of sulfur-containing compounds, e.g., as described in U.S. Pat. Nos. 5,910,440, 5,824,207, 5,753,102, 3,341,448 and 2,749,284. Oxidation of organosulfur compounds is a desirable process to minimize the sulfur content of hydrocarbon feeds, particularly to remove refractory organosulfur compounds such as dibenzothiophene and other aromatic organosulfur compounds. During oxidation, the sulfur-containing compounds are converted to their corresponding sulfoxides, having one oxygen atom bonded to the sulfur heteroatom, and/or to sulfones, having two oxygen atoms bonded to the sulfur heteroatom. Oxidation of certain sulfur-containing compounds increases their solubility in certain solvents. The hydrocarbon stream containing soluble sulfoxides and/or sulfones are extracted from the hydrocarbon using a liquid-liquid extraction process.

Commonly owned Martinie et al. U.S. Patent Publication 2007/0051667, now issued U.S. Pat. No. 7,744,749, discloses oxidative desulfurization of diesel fuel followed by liquid-liquid countercurrent extraction. The oxidation uses an oxidant such as hydrogen peroxide combined with acetic acid. The oxidations products, mainly sulfones, are extracted with a polar solvent such as methanol, acetonitrile, DMSO, or DMF.

Schoonover U.S. Pat. No. 7,001,504 discloses a method for extracting organosulfur compounds from hydrocarbons using ionic liquid. The organic sulfur is partially oxidized to sulfoxides and/or sulfones prior to or during the extraction step. However, the selectivity of the ionic liquids to the sulfur-containing compounds is not discussed in this reference. It is likely that non-treated organosulfur compounds, other aromatics and other hydrocarbons are also co-extracted to a considerable degree, thereby detrimentally impacting product yield.

Stanciulescu et al. U.S. Pat. No. 6,673,236 discloses catalytic oxidative desulfurization of hydrocarbon fuels followed by the extraction of oxidation products using a polar solvent. Ethanol was used during the catalytic oxidation step, and pure methanol was used as a polar solvent for removing the oxidized sulfurous compounds. However, it is known that the polar solvent methanol has a significant affinity for non-treated sulfur compounds, aromatics and other hydrocarbons, thus reducing the overall product yield in a manner that may not be commercially acceptable.

While the processes described above can be effective to remove sulfoxides and/or sulfones from a hydrocarbon mixture, problems remain related to co-extraction of other valuable hydrocarbon components, thus reducing the overall hydrocarbon product yield.

Therefore, it is an object of the present invention to provide a process for selective removal of oxidized sulfur compounds from a hydrocarbon mixture that minimizes co-extraction of valuable hydrocarbon components.

SUMMARY OF THE INVENTION

The process described herein is directed to selective extraction of sulfoxides, or sulfoxides in combination with sulfones, from hydrocarbon mixtures containing these compounds. A significant advantage of the process described herein is that oxidation products resulting from oxidative desulfurization of hydrocarbon feedstocks are selectively extracted with minimum co-extraction of non-oxidized products such as valuable hydrocarbon fuel components.

According to the process described herein, a selective solvent formulation, which, as used herein refers to a solvent formulation having particular solubility to the target oxidation by-product, is brought into contact with a hydrocarbon mixture during or after oxidation reactions that produce sulfoxides and/or sulfones. In certain embodiments, the hydrocarbon mixture containing sulfoxides and/or sulfones is contacted with the selective solvent formulation under mild conditions, i.e., at a temperature in the range of from about 0° C. to about 40° C., and a pressure in the range of from about 10 kPa to about 205 kPa, in certain embodiments about 95 kPa to about 105 kPa, and in further embodiments about 101 kPa.

The liquid-liquid extraction process can be carried out in a batch reactor, a continuous flow reactor, a tubular flow reactor, and/or in a liquid-liquid separator. An advantage of the process described herein compared to prior art extraction processes relates to the use of a selective solvent formulation that minimizes co-extraction of valuable hydrocarbon compounds during the liquid-liquid extraction step.

Another advantage of the process described herein is facilitating extraction of sulfoxides, and/or sulfoxides combined with sulfones, resulting from oxidation of hydrocarbon feeds by using the selective solvent formulation, thereby reducing the complexity and overall number of extractive steps. In conventional approaches, pure solvent is required, and necessary steps include storage of large quantities of highly flammable solvent, recycling of large quantities of solvent with an evaporation unit and distillation unit with multiple stages of cooling towers with associated tanks to segregate the sulfoxides and sulfones from the co-extraction of aromatics along with untreated organosulfur compounds. However, the process described herein is selective to extract the oxidized sulfur, and the solvent is recycled and separated from oxidized sulfur. In addition, polishing of oxidant material can be accomplished by flashing water after extraction, which can eliminate acid, peroxide or solvent remaining in treated stream. Therefore, by employing the selective solvent formulations of the process described herein, the total sulfur will be reduced in a shorter time while minimizing the co-extraction of other valuable hydrocarbons.

A further advantage of certain embodiments of the process described herein is the reduction of the oxygen required and a reduction in the oxidation reaction time by promoting formation of sulfoxides rather than increasing the oxidation to the subsequent step of sulfone formation. Sulfoxides can be formed using existing oxidation methods of photo-oxidation, photochemical oxidation, ozonation, ionic liquid oxidation, electro-chemical oxidation, bio-desulfurization, or contacting with hydrogen peroxides, organic peracids, peroxomonophosphoric acid, nitrogen oxides and/or nitric acid. In general, sulfoxides are more easily extracted than sulfones. Sulfoxides alone can be extracted with less solvent formulation. Under oxidation conditions using peroxides as the oxidation agent at mild operating conditions such as temperatures of about 30° C. to about 40° C. both sulfoxides and sulfones are formed.

With appropriate oxidation conditions and/or catalysts, sulfoxide production can be favored. Using certain solvents, the formulation concentration can be increased to extract both sulfoxides and sulfones while minimizing or eliminating co-extraction of untreated organosulfur compounds.

As used herein, the term "sulfoxide products" refers to sulfoxides resulting from oxidation of organosulfur compounds and "sulfoxidation products" refers to the combination of sulfoxides and sulfones resulting from oxidation of organosulfur compounds.

Also as used herein, the term "bulky sulfoxide products" refers to sulfoxides having more than 12 carbon atoms, thiophenes with more than 4 carbon atoms, and sulfoxidation products of polyaromatic organosulfur compounds such as benzothiophenes, napthothiophenes, dibenzothiophenes, naptho-benzo-thiophene and alkyl and dialkyl derivatives of any of the aforementioned aromatic organosulfur compounds.

In addition, as used herein, the term "bulky sulfoxidation products" refers to a combination of sulfoxides and sulfones having more than 12 carbon atoms, thiophenes with more than 4 carbon atoms, and sulfoxidation products of polyaromatic organosulfur compounds such as benzothiophenes, napthothiophenes, dibenzothiophenes, naptho-benzo-thiophene and alkyl and dialkyl derivatives of any of the aforementioned aromatic organosulfur compounds.

Further, as used herein, "non-bulky sulfoxide products" refers to non-aromatic compounds including dimethyl sulfoxide, dibutyl sulfoxide and other sulfoxides having up to about 12 carbon atoms, or sulfoxides having a single ring structure, including thiophene sulfoxide and alkyl and dialkyl derivatives of thiophene sulfoxide with alkyl groups, having 1 to 4 carbon atoms.

Still further, as used herein. "non-bulky sulfoxidation products" refers to non-aromatic compounds including dimethyl sulfoxide, dimethyl sulfone, dibutyl sulfoxide, dibutyl sulfone and other sulfoxides and sulfones having up to about 12 carbon atoms, or sulfoxides having a single ring structure, including thiophene sulfoxide, thiophene sulfone and alkyl and dialkyl derivatives of thiophene sulfoxide and thiophene sulfone with alkyl groups, having 1 to 4 carbon atoms.

BRIEF DESCRIPTION OF THE DRAWINGS

The foregoing summary as well as the following detailed description will be best understood when read in conjunction with the attached drawings. For the purpose of illustrating the invention, there are shown in the drawings embodiments which are presently preferred. It should be understood, however, that the invention is not limited to the precise arrangements and apparatus shown. In the drawings the same numeral is used to refer to the same or similar elements, in which.

DETAILED DESCRIPTION OF THE INVENTION

Process Configuration

Figure 1:
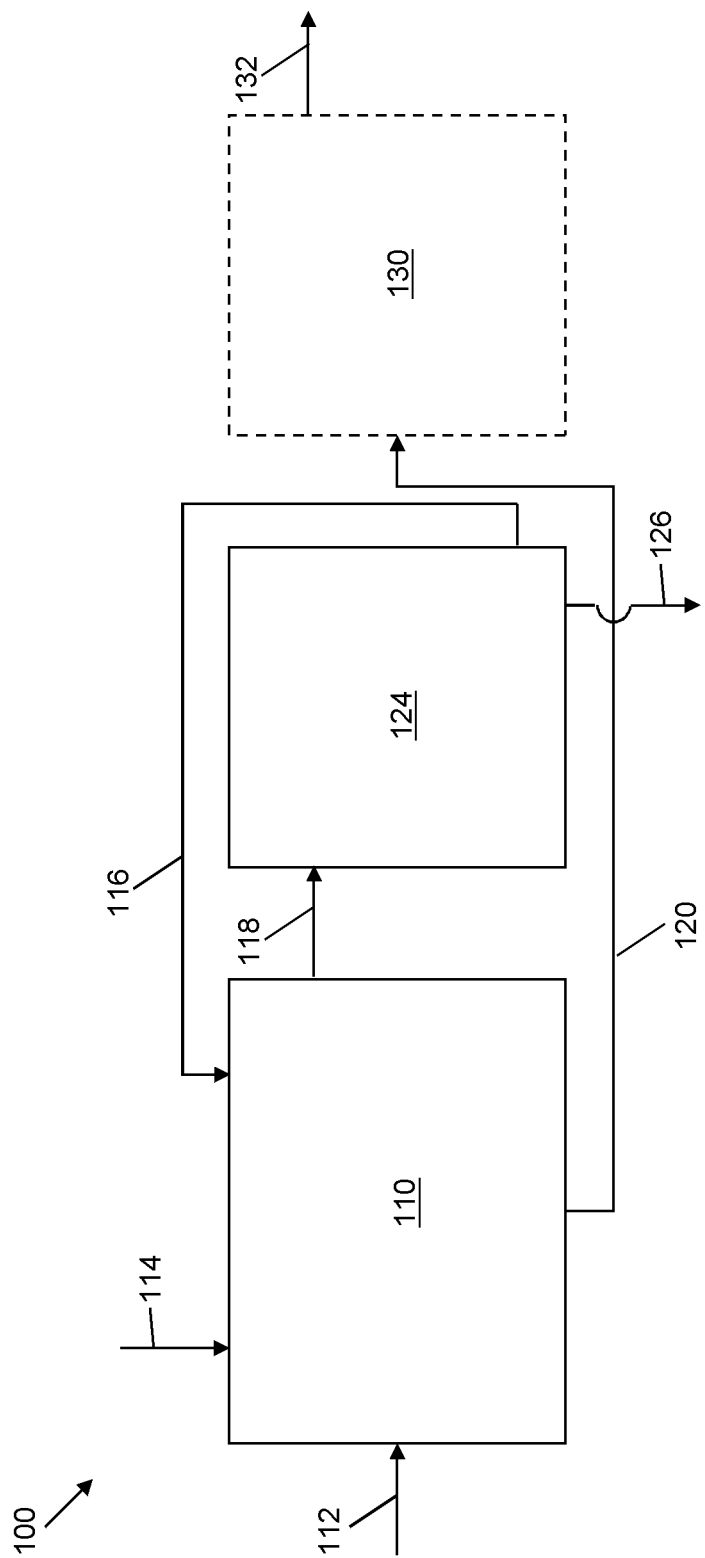
FIG. 1 is a schematic illustration of a system for sulfoxidation of a hydrocarbon stream and solvent extraction of the sulfoxidation products according to one embodiment of the present invention.

Referring now to FIG. 1, a schematic flow diagram of system 100 for oxidation of a hydrocarbon stream and solvent extraction of oxidation products is shown. The concentration and type of sulfur compounds in the feedstream are preferably determined prior to oxidation so as to optimize reaction and to employ suitable selective solvent formulations as described herein. An integrated oxidation/extraction reactor zone 110, e.g., an agitator, a continuously stirred tank reactor, and/or other type of mixing vessel, receives the sulfur-containing hydrocarbon feed via line 112 and an oxidant via line 114. The oxidant can be acetic acid, hydrogen peroxide, or another suitable oxidant, or combination of oxidants, as are known to those of ordinary skill in the art. The ratio of oxidant to the hydrocarbon feed can vary depending on the total sulfur concentration and speciation.

In certain embodiments, a suitable weight ratio of organic sulfur to oxidant is about 1:4, but it will be appreciated by one of ordinary skill in the art that the ratio can vary. In certain embodiments, the temperature and pressure conditions in the integrated oxidation/extraction reactor zone 110 during the oxidation reactions are generally mild, e.g., a temperature in the range of from about 0° C. to about 40° C., in certain embodiments about 30° C. to about 40° C., and a pressure in the range of from about 10 kPa to about 205 kPa. The hydrocarbon and oxidant remain in contact for a period of time sufficient to achieve a desired level of oxidation reactions, e.g., between about 30 minutes and about 180 minutes. Compared to conventional oxidation temperature of about 80° C. to 90° C., these mild conditions result in lower consumption of oxidant and desirably minimize the conversion of olefins, produce a greater proportion of sulfoxides, and minimize or eliminate the likelihood of polymerization. In contrast, higher oxidation temperatures result in a greater proportion of sulfones as the oxidation product. Sulfoxide formation is generally preferred over sulfone formation, as less oxidant is consumed, and as described herein, certain selective solvent formulations can be employed to target sulfoxides while minimizing co-extraction of at least certain sulfones and desired hydrocarbon products.

A predetermined quantity of selective solvent formulation is charged to the integrated oxidation/extraction reactor zone 110. At least a portion of the solvent enters via a recycle line 116 from a solvent recovery zone 124 once the system has achieved a steady-state operating condition. The selective solvent formulation extracts sulfoxides, or a combination of sulfoxides and sulfones, that have been formed during the oxidation of the sulfur-containing hydrocarbon material. The selective solvent formulation can be present in a ratio of solvent-to-hydrocarbon in an amount of about 1:2 to about 3:1 by weight, depending on the sulfur speciation of the hydrocarbon stream, the degree of oxidation, and whether the target oxidation products for extraction include primarily sulfoxides or a combination of sulfoxides and sulfones. For extraction of non-bulky sulfoxide products and/or sulfoxidation products (i.e., combined sulfoxides and sulfones), a ratio toward the lower end, e.g., 1:1, is suitable. For extraction of bulky sulfoxide products and/or sulfoxidation products, a ratio toward the higher end, e.g., about 11 to about 3:1 is suitable.

Hydrocarbon mixtures including the oxidized or partially oxidized hydrocarbon contents are contacted by intimate mixing with the selective solvent formulation for a period of time that is sufficient to extract the sulfoxides, or combination of sulfoxides and sulfones, and solubilize them in the selective solvent formulation, e.g., between about 10 minutes and about 60 minutes. In certain embodiments, the temperature and pressure conditions in the integrated oxidation/extraction reactor zone 110 during the extraction step, are generally mild, e.g., a temperature in the range of from about 0° C. to about 40° C., in certain embodiments between about 15° C. and about 40° C. and a pressure in the range of from about 10 kPa to about 205 kPa, in certain embodiments about 101 kPa (about 1 atmosphere). In certain embodiments, a separate cooling step is not required between the steps of oxidation and extraction.

After the mixing and extraction are completed, the mixture is allowed to settle for a period of time sufficient to result in phase separation between the hydrocarbon phase and the solvent phase, e.g., between about 60 minutes and about 180 minutes.

The solvent phase containing the selective solvent formulation and extracted sulfoxides, or combination of sulfoxides and sulfones, is decanted via line 118 to the solvent recovery zone 124. The recovery zone 124 can be an evaporation operation, in which the contents are heated to a temperature of about 110° C. to evaporate water and solvent at atmospheric pressure for recovery via line 116 to the integrated oxidation/extraction reactor zone 110, and the oxidized organosulfur compounds in liquid form are recovered and evacuated via line 126. Extracted sulfoxides and sulfones can be treated to cleave the sulfur-oxygen bonds by pyrolysis reactions to recover sulfur-free hydrocarbons (not shown).

A reduced sulfur-content hydrocarbon stream is passed via line 120 to an optional polishing zone 130 from which a polished stream is discharged via line 132. The polishing zone 130 can be one or more suitable polishing apparatus capable of removing impurities such as organic acids that can remain after solvent extraction. For instance, an aqueous polishing unit can be used due to the ability to recycle the polishing water stream. Another suitable type of polishing unit is a solid polishing unit based on adsorption of acidic organic molecules that can be carried over with the hydrocarbon stream. In addition, adsorbent material in a solid polishing unit can adsorb any remaining sulfoxides and/or sulfones in the hydrocarbon stream. The adsorbent material can include one or more of clay, alumina oxide, silica gel, molecular sieves, zeolite, a combination thereof, or any other adsorbent material or combination of adsorbent materials known to one of ordinary skill in the art. In additional alternative embodiments (not shown) the hydrocarbon phase transferred via line 120 from the integrated oxidation/extraction reactor zone 110 can be directly discharged and used as a feedstream for further refining operations, or collected as an end product.

Figure 2:
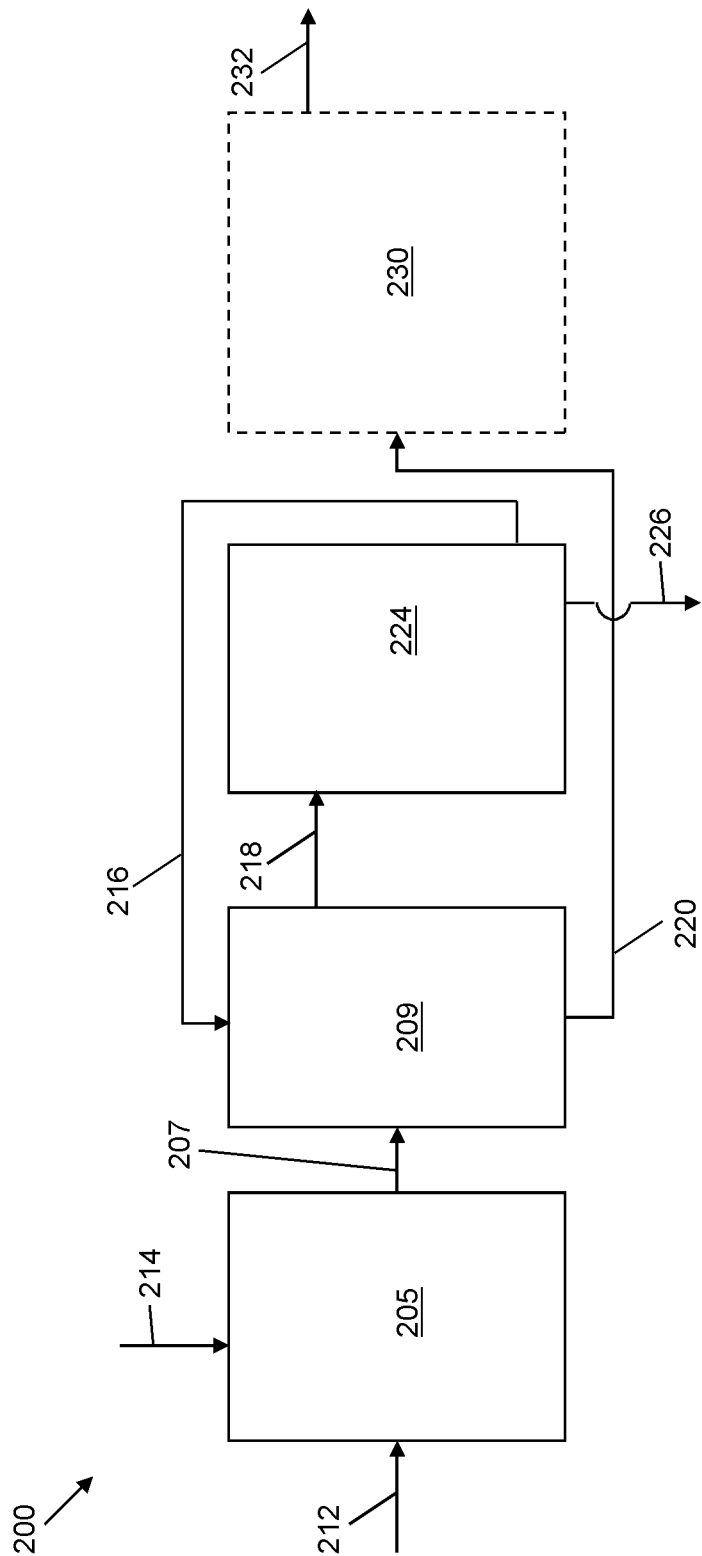
FIG. 2 is a schematic illustration of a system for sulfoxidation of a hydrocarbon stream and solvent extraction of sulfoxidation products according to another embodiment of the present invention.

Referring now to FIG. 2, a schematic flow diagram of a system 200 for oxidation of a hydrocarbon stream and solvent extraction of the oxidation products is shown. The hydrocarbon feed, oxidative materials, process conditions, and other parameters are similar to those of system 100, with the exception that the oxidation reactions occur in a zone separate from the solvent extraction. An oxidation reaction zone 205 receives a sulfur-containing hydrocarbon feed via line 212 and an oxidant via line 214. The oxidation reaction zone 205 is generally a mixing device, such as an agitator or a continuously stirred tank reactor. In certain embodiments, the temperature and pressure conditions in the oxidation reaction zone 205 are generally mild, e.g., a temperature in the range of from about 0° C. to about 40° C., in certain embodiments between about 30° C. and about 40° C. and a pressure in the range of from about 10 kPa to about 205 kPa. The hydrocarbon and oxidant remain in contact in the oxidation reaction zone 205 for a period of time sufficient to achieve a predetermined level of oxidative desulfurization, e.g., between about 30 minutes and about 180 minutes.

The hydrocarbon stream containing the oxidized products is passed via line 207 to a solvent extraction zone 209. A quantity of selective solvent formulation is charged to the solvent extraction zone 209 via recycle line 216 from a solvent recovery zone 224. The selective solvent formulation extracts the sulfoxides, or combination of sulfoxides and sulfones, that are formed during the oxidation of the sulfur-containing hydrocarbon material. In certain embodiments, the temperature and pressure conditions in the solvent extraction zone 209 are generally mild, e.g., a temperature in the range of from about 0° C. to about 40° C., and a pressure in the range of from about 10 kPa to about 205 kPa.

The oxidized or partially oxidized hydrocarbon contents are contacted with the selective solvent formulation by intimate mixing in the solvent extraction zone 209 for a period of time sufficient to extract the sulfoxides, or combination of sulfoxides and sulfones, e.g., between about 10 minutes and about 60 minutes. Mixing is discontinued and the contents are allowed to settle for a period of time sufficient to allow phase separation of the hydrocarbon phase and the solvent phase, e.g., between about 60 minutes and about 180 minutes.

The solvent phase containing the selective solvent formulation and extracted sulfoxides, or combination of sulfoxides and sulfones, is decanted via line 218 to the solvent recovery zone 224, similar to that described with respect to system 100. A reduced sulfur-content hydrocarbon stream is passed via line 220 to an optional polishing unit 230 from which a polished stream is discharged via line 232. In additional alternative embodiments (not shown) the hydrocarbon phase exiting via line 220 from the solvent extraction zone 209 can be directly discharged and used as a feedstream for further refining operations, or collected as an end product.

General

In contrast to known extraction processes, the process described herein employs selective solvent formulations that are less than 100% pure solvent. The solvent concentration is selected to target the sulfur speciation of the hydrocarbon mixture that is subjected to the oxidation reaction(s). Therefore, extraction of the target sulfoxide or sulfoxidation products occurs selectively, with minimal co-extraction of other hydrocarbon constituents such as dodecane ($nC_{12}$), toluene, naphthalene, thiophene, dibenzothiophene and dibutyl sulfides, which would otherwise result in an undesirable decrease in product yield.

In general, the selective solvent formulation is an aqueous solution having a concentration range of about 2.5 weight % (W %) to about 70 W % polar organic solvent in water. The polar organic solvent can be acetone, methanol, acetonitrile, acetic acid or formic acid. The particular concentration within this broad range can be specified based on the particular polar organic solvent employed, the sulfur speciation and whether the target oxidation product includes a full range of molecular weight sulfoxide products or combined sulfoxidation products, bulky sulfoxide products or sulfoxidation products, or non-bulky sulfoxide products or sulfoxidation products.

Combinations of two or more of the polar organic solvents in aqueous solution can also be effective in extracting target oxidation products. For example, mixtures can include acetonitrile, formic acid and water; acetone, acetic acid and water; acetone, formic acid and water; and other mixtures comprising water and two or more polar solvents selected from acetone, methanol, acetonitrile, acetic acid and formic acid.

For hydrocarbon mixtures having bulky sulfoxide products or bulky sulfoxidation products, the selective solvent formulation is provided with a relatively higher concentration of polar organic solvent. For instance, the concentration of the aqueous polar organic solvent solution can be about 30 W % to about 70 W %.

The following descriptions provide the activity coefficients (γ) of various solvent formulations relative to certain hydrocarbon constituents including sulfoxidation products based upon computer-modeled simulations using COSMO-RS (COnductor-like Screening MOdel for Realistic Solvents) software commercially available from Scientific Computing & Modelling NV, Amsterdam, The Netherlands.

As is known to those of ordinary skill in the art, lower values of the activity coefficient represent higher solubility of the particular constituent in the solvent, while higher values of the activity coefficient represent lower solubility of the particular constituent in the solvent.

The modeled γ is based on calculations of sulfoxide and sulfone molecules as solute to be extracted from the mixed hydrocarbon stream. The hydrocarbon stream of non-extracted hydrocarbons is defined as the raffinate. Reference to the values of γ set forth in the following tables allows selection of solvents with minimum co-extraction of other hydrocarbons.

It has been determined that γ values of 0 to about 16.5 correspond to extraction of acceptable levels of the oxidized molecules. However, γ values of about 16.5 or greater indicate extraction rates that are not practical for the oxidation products, but desirable for the non-targeted species, i.e., avoiding solubilization of the non-targeted hydrocarbons and unconverted organosulfur compounds.

Furthermore, a relatively large difference between γ values of the targeted oxidized sulfur compounds and the other non-targeted constituents is preferable, as this large difference indicates minimal co-extraction of the raffinate components. In addition, a large difference increases the selectivity of solvent formulation to extract the targeted oxidized organic sulfur compounds. Therefore, in the practice of the process described herein, the optimum formulation is based on maximizing the difference in the respective γ values.

The value of the activity coefficient of the targeted compounds ($\gamma_T$) is minimized while the value of the activity coefficient of the non-targeted compounds ($\gamma_{NT}$) is maximized. In certain embodiments, the ratio $\gamma_{T\text{-}DBT\text{-}Sulfoxide}$:$\gamma_{NT\text{-}DBT}$ is at a maximum 1:5, wherein $\gamma_{T\text{-}DBT\text{-}Sulfoxide}$ denotes the activity coefficient of targeted compound dibenzothiophene sulfoxide and $\gamma_{NT\text{-}DBT}$ denotes the activity coefficient of non-targeted compound dibenzothiophene. However it has been determined a desirable ratio $\gamma_{T\text{-}DBT\text{-}Sulfoxide}$:$\gamma_{NT\text{-}DBT}$ can be as low as 1:10, 1:20, 1:50, 1:100, 1:500 and, in certain embodiments, as low as 1:1600.

Model Feed Information and Sulfur Speciation

The first model fuel (referred to herein as "model A" with corresponding nomenclature in the activity coefficient tables that follow, i.e., tables 2A, 3A, 4A, 5A, 6A, 7A, 8A and 9A) used as the input to the COSMO-RS software along with the various solvent formulations are based on a straight run diesel sample containing various concentrations of non-sulfur alkane constituents from $C_8$ to $C_{25}$.

The second model fuel used (referred to herein as "model B" with corresponding nomenclature in the activity coefficient tables that follow, i.e., tables 2B, 3B, 4B, 5B and 6B) as the input to the COSMO-RS software along with the various solvent formulations are based on a straight run diesel sample containing the following non-sulfur alkane constituents: $C_8$ (0.4 W %), $C_9$ (1.3 W %), $C_{10}$ (3.1 W %), $C_{11}$ (6.1 W %), $C_{12}$ (8.4 W %), $C_{13}$ (9.9 W %), $C_{14}$ (11.2 W %), $C_{15}$ (11.7 W %), $C_{16}$ (11.7 W %), $C_{17}$ (10.3 W %), $C_{18}$ (8.8 W %), $C_{19}$ (6.7 W %). $C_{20}$ (4.9 W %), $C_{21}$ (2.9 W %), $C_{22}$ (1.6 W %), $C_{23}$ (0.8 W %), $C_{24}$ (0.3 W %), $C_{25}$ (0.1 W %). In addition, the diesel used for model B has an aromatic concentration ranging from 15 W % to 30 W %. The sulfur speciation of the diesel used for the below models is as follows:

TABLE 1

| IUPAC name | Concentration, ppm |
|---|---|
| Benzo[b]thiophene | 8 ± 1 |
| 5-methyl-1-benzo(b)thiophene | 42 ± 8 |
| 4-methyl-1-benzo(b)thiophene | 9 ± 2 |
| 2,6-dimethyl-1-benzo(b)thiophene | 81 ± 15 |
| 2,4-dimethyl-1-benzo(b)thiophene | 179 ± 32 |
| 2,3-dimethyl-1-benzo(b)thiophene | 404 ± 73 |
| 2,3,4-trimethyl-1-benzo(b)thiophene | 189 ± 34 |
| 2,5,6-trimethyl-1-benzo(b)thiophene | 6 ± 1 |
| dibenzothiophene | 387 ± 70 |
| 4-methyldibenzothiophene | 706 ± 127 |
| 2-methyldibenzothiophene and 3-methyldibenzothiophene | 587 ± 106 |
| 1-methyldibenzothiophene | 380 ± 68 |
| 4-ethyldibenzothiophene | 195 ± 35 |
| 4,6-dimethyldibenzothiophene | 350 + 63 |
| 2,4-dimethyldibenzothiophene | 249 ± 45 |
| 2-ethyldibenzothiophene | 69 ± 12 |
| 3,6-dimethyldibenzothiophene | 771 ± 139 |
| 2,8-dimethyldibenzothiophene | 338 ± 61 |
| 1,4-dimethyldibenzothiophene | 615 ± 111 |
| 1,3-dimethyldibenzothiophene | 179 ± 32 |
| 1,2-dimethyldibenzothiophene | 95 ± 17 |
| 2,4,8-trimethyldibenzothiophene | 335 ± 60 |
| 4-ethyl,6-methyldibenzothiophene | 288 ± 52 |
| 4-propyldibenzothiophene | 82 ± 15 |
| 2-propyldibenzothiophene | 256 ± 46 |
| 4-butyldibenzothiophene | 62 ± 11 |
| 2,4,7-trimethyldibenzothiophene and 2,3,8-trimethyldibenzothiophene | 75 ± 13 |
| 2-butyldibenzothiophene | 111 ± 20 |
| 2-pentyldibenzothiophene | 93 ± 17 |
| 1-phenyldibenzothiophene | 11 ± 2 |
| 4-phenyldibenzothiophene | 34 ± 6 |

Acetone Formulations

In one embodiment of the process described herein, the solvent formulation comprises an aqueous solution of acetone. An aqueous solution of acetone having a concentration of about 2.5 W % to about 50 W % is particularly suitable as a selective solvent formulation for extraction of sulfoxide products. The level of extraction and the specific concentration of the acetone selective solvent formulation depend on factors including, but not limited to the sulfur speciation of the feed hydrocarbon mixture and whether the target sulfoxide products to be extracted are non-bulky or bulky. For non-bulky sulfoxide products the concentration of the aqueous acetone solution can be about 2.5 W % to about 20 W %, which will extract the non-bulky sulfoxide products, while minimizing co-extraction of certain sulfones, untreated organosulfur compounds, non-heteroatom aromatics and other hydrocarbons. For bulky sulfoxide products, the concentration of the aqueous acetone solution can be about 20 W % to about 50 W %, which will extract the bulky sulfoxide products, while minimizing, co-extraction of certain sulfones, non-heteroatom aromatics, untreated organosulfur compounds and other hydrocarbons.

In an extractive simulation. COSMO-RS software was used to simulate γ for selective extraction of oxidized model A fuel by solvent formulations of aqueous acetone. Acetone is desirable as a polar organic solvent due to its low boiling point, thereby facilitating its recovery and separation from the sulfoxide products.

Figure 3:
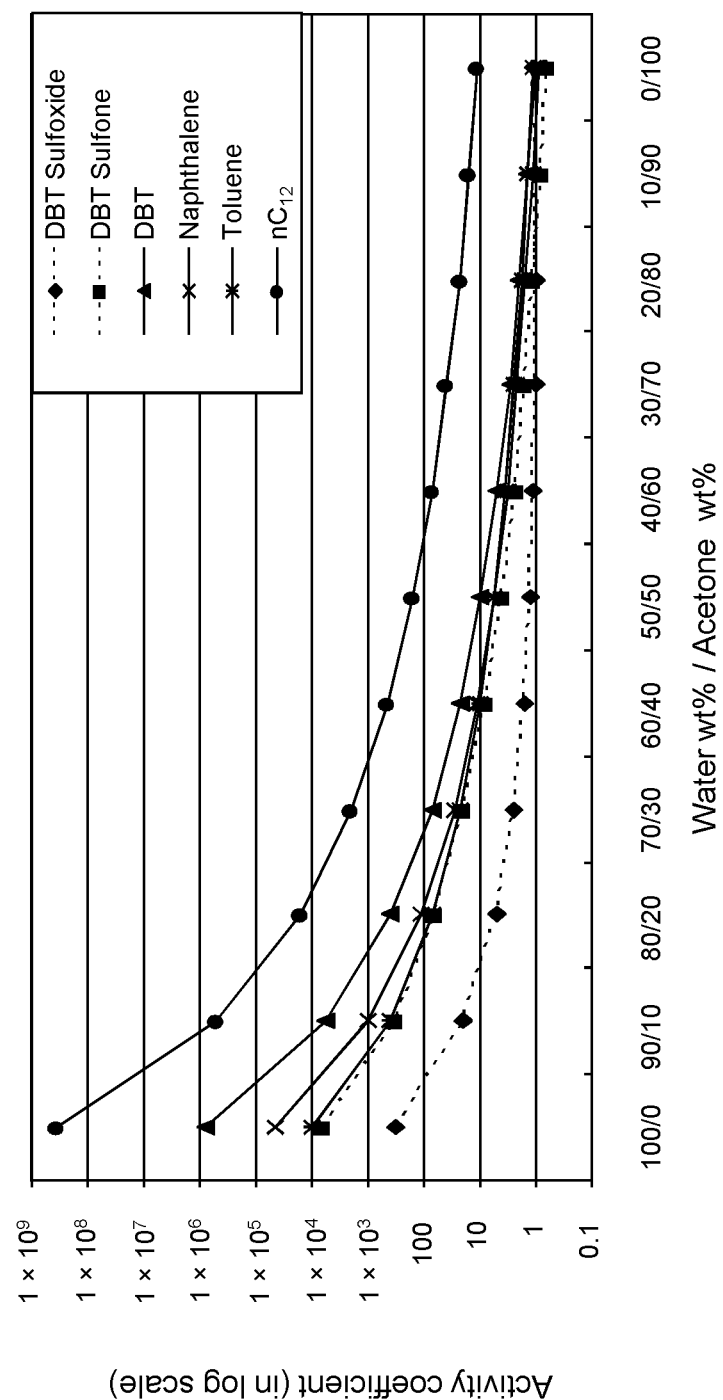
FIGS. 3, 4 and 5 are plots of computational models of the activity coefficient values for a range of concentrations of an acetone solvent formulation for sulfoxidation products of DBT, thiophene and dibutyl sulfide compounds respectively, relative to other components in a hydrocarbon mixture.
Figure 4:
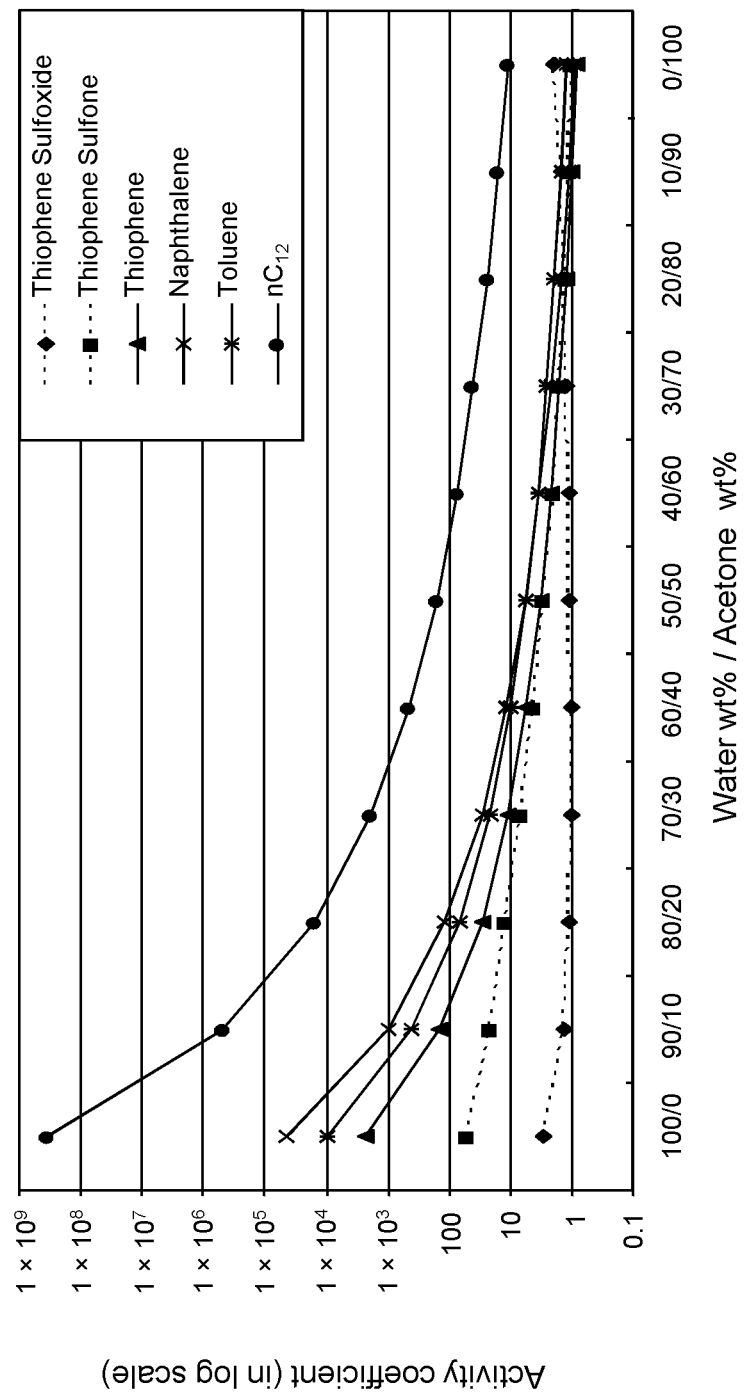
Figure 5:
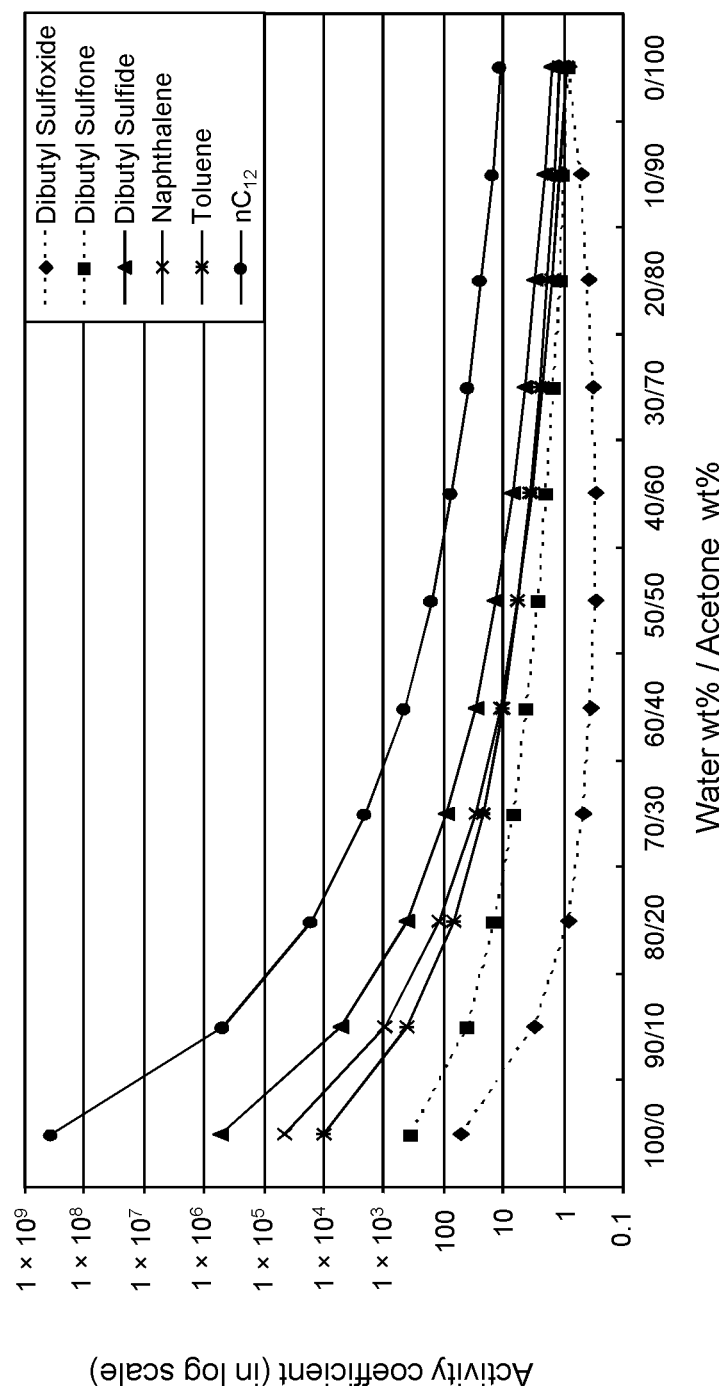

Table 2A illustrates the activity coefficient of different concentrations of aqueous acetone for the compounds listed. Based on the activity coefficient values in Table 2A, a useful aqueous acetone selective solvent formulation has a concentration of about 20 W % to about 30 W % for extraction of DBT sulfoxide, with minimal co-extraction of certain sulfones, untreated organosulfur compounds, aromatics and other hydrocarbons, as shown in FIG. 3. An aqueous acetone selective solvent formulation of about 20 W % to about 30 W % is also useful for extraction of thiophene sulfoxide, thiophene sulfone, dibutyl sulfoxide and dibutyl sulfone. If the target sulfoxidation products are primarily thiophene sulfoxide and dibutyl sulfoxide, a useful selective solvent formulation can be about 5 W % to about 10 W % aqueous acetone, as shown in FIGS. 4 and 5.

In another extraction simulation, COSMO-RS software was used to simulate γ for formulations of aqueous acetone as extraction solvents for oxidized model B fuel. The results are shown in Table 2B. Activity coefficient values as shown in Table 2B indicate that certain formulations of aqueous acetone will selectively extract bulky sulfoxide products while minimizing co-extraction of their corresponding sulfones and underlying organosulfur compounds. Based on the activity coefficient values in Table 2B, a useful aqueous acetone selective solvent formulation has a concentration of about 10 W % to about 30 W % for selective extraction of bulky sulfoxidation products including alkyl and dialkyl derivatives of benzothiophenes and dibenzothiophenes.

In Table 2B, activity coefficients for targeted sulfoxides for which extraction is favored are marked with an asterisk ("*"), activity coefficients for non-targeted corresponding sulfones and the underlying organosulfur compounds for which co-extraction is minimized are marked with a pound symbol ("#").

TABLE 2A

| Compound | Solvent (Acetone W %/Water W %) | | | | | | | | | | |
|---|---|---|---|---|---|---|---|---|---|---|---|
| | 0/100 | 10/90 | 20/80 | 30/70 | 40/60 | 50/50 | 60/40 | 70/30 | 80/20 | 90/10 | 100/0 |
| | Activity Coefficient | | | | | | | | | | |
| dibenzothiophene 5-oxide (DBT sulfoxide) | 320.54 | 18.92 | 5.21 | 2.56 | 1.65 | 1.27 | 1.07 | 0.99 | 0.96 | 1.01 | 1.16 |
| dibenzothiophene 5,5-dioxide (DBT sulfone) | 6063.24 | 330.30 | 61.56 | 19.11 | 7.92 | 4.01 | 2.34 | 1.51 | 1.06 | 0.79 | 0.63 |
| dibenzothiophene (DBT) | 7.90E+05 | 5825.50 | 399.41 | 72.97 | 22.65 | 9.49 | 4.90 | 2.92 | 1.92 | 1.35 | 1.01 |
| 1-butylsulfinyl-butane (Dibutyl Sulfoxide) | 51.42 | 2.86 | 0.83 | 0.45 | 0.33 | 0.30 | 0.29 | 0.31 | 0.37 | 0.48 | 0.81 |
| 1-butylsulfonyl-butane (Dibutyl Sulfone) | 336.97 | 38.86 | 13.20 | 6.49 | 3.82 | 2.51 | 1.80 | 1.38 | 1.11 | 0.92 | 0.81 |
| 1-butylsulfanyl-butane (Dibutyl Sulfide) | 5.04E+05 | 4964.16 | 411.58 | 86.49 | 29.08 | 13.07 | 7.03 | 4.35 | 2.92 | 2.10 | 1.58 |
| Thiophene Sulfoxide | 2.83 | 1.38 | 1.09 | 1.02 | 1.02 | 1.05 | 1.11 | 1.20 | 1.32 | 1.52 | 1.86 |
| Thiophene Sulfone | 49.40 | 21.98 | 11.47 | 6.49 | 4.06 | 2.75 | 1.99 | 1.54 | 1.25 | 1.05 | 0.95 |
| Thiophene | 2208.35 | 138.38 | 29.37 | 10.80 | 5.37 | 3.19 | 2.14 | 1.57 | 1.21 | 0.98 | 0.82 |
| Naphthalene | 4.44E+04 | 953.37 | 114.43 | 29.37 | 11.36 | 5.64 | 3.29 | 2.16 | 1.52 | 1.14 | 0.90 |
| Toluene | 9798.65 | 395.44 | 67.36 | 21.76 | 9.87 | 5.53 | 3.53 | 2.48 | 1.86 | 1.45 | 1.19 |
| $nC_{12}$ | 3.52E+08 | 4.99E+05 | 1.60E+04 | 1939.14 | 459.44 | 162.39 | 72.97 | 39.25 | 23.57 | 15.49 | 10.80 |

TABLE 2B

| Compound | | Solvent (Acetone W %/Water W %) | | | | | | | | | | |
|---|---|---|---|---|---|---|---|---|---|---|---|---|
| Common Name | IUPAC | 0/100 | 10/90 | 20/80 | 30/70 | 40/60 | 50/50 | 60/40 | 70/30 | 80/20 | 90/10 | 100/0 |
| | | Activity Coefficient | | | | | | | | | | |
| 6-Methylbenzo-thiophene oxide | 6-methyl-1-benzo(b)thiophene 1-oxide | 47.00 | 4.57* | 1.77* | 1.10 | 0.84 | 0.73 | 0.68 | 0.67 | 0.70 | 0.77 | 0.93 |
| 6-Methylbenzo-thiophene sulfone | 6-methyl-1-benzo(b)thiophene 1,1-dioxide | 988.00 | 95.58# | 25.91# | 10.23 | 5.07 | 2.93 | 1.89 | 1.33 | 1.00 | 0.78 | 0.65 |
| 6-Methylbenzo-thiophene | 6-methyl-1-benzo(b)thiophene | 1.20E+05 | 1455.35# | 140.47# | 32.46 | 11.90 | 5.74 | 3.29 | 2.13 | 1.49 | 1.12 | 0.87 |
| 2,6-Dimethyl-benzothiophene oxide | 2,6-dimethyl-1-benzo(b)thiophene 1-oxide | 88.00 | 5.64* | 1.82* | 1.03 | 0.75 | 0.63 | 0.59 | 0.58 | 0.61 | 0.68 | 0.86 |
| 2,6-Dimethyl-benzothiophene sulfone | 2,6-dimethyl-1-benzo(b)thiophene 1,1-dioxide | 1967.00 | 133.00# | 31.30# | 11.50 | 5.45 | 3.05 | 1.93 | 1.33 | 0.98 | 0.77 | 0.62 |
| 2,6-Dimethyl-benzothiophene | 2,6-dimethyl-1-benzo(b)thiophene | 3.87E+05 | 2958.44# | 228.30# | 46.29 | 15.58 | 7.07 | 3.88 | 2.42 | 1.66 | 1.21 | 0.93 |
| 2,3,6-Trimethyl-benzothiophene oxide | 2,3,6-trimethyl-1-benzo(b)thiophene 1-oxide | 313.00 | 12.29* | 3.13* | 1.53 | 1.01 | 0.79 | 0.69 | 0.65 | 0.65 | 0.70 | 0.86 |
| 2,3,6-Trimethyl-benzothiophene sulfone | 2,3,6-trimethyl-1-benzo(b)thiophene 1,1-dioxide | 5917.00 | 250.17# | 47.36# | 15.43 | 6.78 | 3.62 | 2.20 | 1.48 | 1.07 | 0.82 | 0.65 |
| 2,3,6-Trimethyl-benzothiophene | 2,3,6-trimethyl-1-benzo(b)thiophene | 1.17E+06 | 5943.06# | 377.69# | 68.46 | 21.43 | 9.24 | 4.89 | 2.97 | 1.98 | 1.42 | 1.07 |
| Dibenzothiophene oxide | dibenzothiophene 5-oxide | 251.00 | 12.25* | 3.38* | 1.70 | 1.14 | 0.90 | 0.78 | 0.73 | 0.73 | 0.78 | 0.91 |
| Dibenzothiophene sulfone | dibenzothiophene 5,5-dioxide | 6267.00 | 270.83# | 48.57# | 14.85 | 6.18 | 3.16 | 1.86 | 1.22 | 0.86 | 0.65 | 0.52 |

TABLE 2B-continued

| Compound | | Solvent (Acetone W %/Water W %) | | | | | | | | | | |
|---|---|---|---|---|---|---|---|---|---|---|---|---|
| | | 0/100 | 10/90 | 20/80 | 30/70 | 40/60 | 50/50 | 60/40 | 70/30 | 80/20 | 90/10 | 100/0 |
| Common Name | IUPAC | Activity Coefficient | | | | | | | | | | |
| Dibenzothiophene | dibenzothiophene | 6.67E+05 | 3900.52[#] | 259.38[#] | 47.64 | 14.96 | 6.45 | 3.41 | 2.07 | 1.38 | 0.99 | 0.75 |
| 4-Methyldibenzo-thiophene oxide | 4-methyldibenzo-thiophene 5-oxide | 1542.00 | 30.51 | 5.51[*] | 2.18[*] | 1.26 | 0.90 | 0.73 | 0.65 | 0.63 | 0.66 | 0.79 |
| 4-Methyldibenzo-thiophene sulfone | 4-methyldibenzo-thiophene 5,5-dioxide | 3.90E+04 | 726.05 | 90.35[#] | 22.74[#] | 8.41 | 3.96 | 2.21 | 1.38 | 0.94 | 0.69 | 0.53 |
| 4-Methyldibenzo-thiophene | 4-methyldibenzo-thiophene | 6.02E+06 | 1.48E+04 | 654.23[#] | 94.69[#] | 25.47 | 9.86 | 4.81 | 2.74 | 1.74 | 1.20 | 0.87 |
| 3,6-Dimethyldi-benzothiophene oxide | 3,6-dimethyldibenzo-thiophene 5-oxide | 718.00 | 22.31 | 4.91[*] | 2.15[*] | 1.31 | 0.96 | 0.80 | 0.72 | 0.69 | 0.72 | 0.83 |
| 3,6-Dimethyldi-benzothiophene sulfone | 3,6-dimethyldibenzo-thiophene 5,5-dioxide | 1.79E+04 | 476.99 | 69.03[#] | 18.84[#] | 7.33 | 3.58 | 2.05 | 1.31 | 0.91 | 0.67 | 0.53 |
| 3,6-Dimethyldi-benzothiophene | 3,6-dimethyldibenzo-thiophene | 1.84E+06 | 7258.60 | 401.16[#] | 66.27[#] | 19.43 | 7.99 | 4.08 | 2.41 | 1.57 | 1.11 | 0.82 |
| 4,6-Dimethyldi-benzothiophene oxide | 4,6-dimethyldibenzo-thiophene 5-oxide | 1664.00 | 33.22 | 6.00[*] | 2.37[*] | 1.35 | 0.96 | 0.77 | 0.69 | 0.66 | 0.68 | 0.79 |
| 4,6-Dimethyldi-benzothiophene sulfone | 4,6-dimethyldibenzo-thiophene 5,5-dioxide | 4.41E+04 | 793.55 | 96.69[#] | 24.02[#] | 8.80 | 4.12 | 2.28 | 1.43 | 0.97 | 0.71 | 0.55 |
| 4,6-Dimethyldi-benzothiophene | 4,6-dimethyldibenzo-thiophene | 5.81E+06 | 1.47E+04 | 652.00[#] | 94.87[#] | 25.60 | 9.93 | 4.85 | 2.77 | 1.76 | 1.21 | 0.89 |
| 2,4-Dimethyldi-benzothiophene oxide | 2,4-dimethyldibenzo-thiophene 5-oxide | 2.47E+03 | 47.35 | 8.19[*] | 3.09[*] | 1.70 | 1.15 | 0.90 | 0.77 | 0.71 | 0.72 | 0.80 |
| 2,4-Dimethyldi-benzothiophene sulfone | 2,4-dimethyldibenzo-thiophene 5,5-dioxide | 3.74E+04 | 709.28 | 90.18[#] | 23.21[#] | 8.75 | 4.20 | 2.37 | 1.50 | 1.03 | 0.76 | 0.59 |
| 2,4-Dimethyldi-benzothiophene | 2,4-dimethyldibenzo-thiophene | 5.04E+06 | 1.36E+04 | 626.15[#] | 93.30[#] | 25.60 | 10.05 | 4.96 | 2.85 | 1.82 | 1.26 | 0.92 |
| 2,4,7-Trimethyldi-benzothiophene oxide | 2,4,7-trimethyldibenzo-thiophene 5-oxide | 4095.00 | 52.04 | 7.68[*] | 2.72[*] | 1.46 | 0.99 | 0.78 | 0.68 | 0.64 | 0.67 | 0.79 |
| 2,4,7-Trimethyldi-benzothiophene sulfone | 2,4,7-trimethyldibenzo-thiophene 5,5-dioxide | 9.72E+04 | 1228.80 | 129.67[#] | 29.82[#] | 10.41 | 4.71 | 2.54 | 1.56 | 1.04 | 0.75 | 0.57 |
| 2,4,7-Trimethyldi-benzothiophene | 2,4,7-trimethyldibenzo-thiophene | 2.05E+07 | 3.17E+04 | 1120.10[#] | 142.36[#] | 35.18 | 12.83 | 5.99 | 3.30 | 2.04 | 1.37 | 0.98 |
| 4-Ethyldibenzo-thiophene oxide | 4-ethyldibenzo-thiophene 5-oxide | 1706.00 | 34.51 | 6.24[*] | 2.46[*] | 1.40 | 0.98 | 0.79 | 0.69 | 0.66 | 0.67 | 0.76 |
| 4-Ethyldibenzo-thiophene sulfone | 4-ethyldibenzo-thiophene 5,5-dioxide | 5.43E+04 | 869.35 | 97.65[#] | 22.99[#] | 8.13 | 3.72 | 2.03 | 1.25 | 0.84 | 0.61 | 0.47 |
| 4-Ethyldibenzo-thiophene | 4-ethyldibenzo-thiophene | 5.28E+06 | 1.35E+04 | 608.55[#] | 89.38[#] | 24.28 | 9.47 | 4.65 | 2.66 | 1.70 | 1.17 | 0.86 |
| 4-Propyldibenzo-thiophene oxide | 4-propyldibenzo-thiophene 5-oxide | 4103.00 | 52.77 | 7.74[*] | 2.71[*] | 1.44 | 0.96 | 0.75 | 0.65 | 0.61 | 0.62 | 0.71 |
| 4-Propyldibenzo-thiophene sulfone | 4-propyldibenzo-thiophene 5,5-dioxide | 1.60E+05 | 1587.37 | 141.28[#] | 28.98[#] | 9.36 | 4.02 | 2.09 | 1.24 | 0.81 | 0.57 | 0.43 |
| 4-Propyldibenzo-thiophene | 4-propyldibenzo-thiophene | 1.72E+07 | 2.70E+04 | 958.28[#] | 122.09[#] | 30.20 | 11.02 | 5.15 | 2.84 | 1.76 | 1.18 | 0.85 |
| 2-Butyldibenzo-thiophene oxide | 2-butyldibenzo-thiophene 5-oxide | 1.43E+04 | 102.03 | 11.28[*] | 3.36[*] | 1.61 | 1.01 | 0.75 | 0.63 | 0.57 | 0.57 | 0.65 |
| 2-Butyldibenzo-thiophene sulfone | 2-butyldibenzo-thiophene 5,5-dioxide | 3.38E+05 | 2365.51 | 180.45[#] | 33.61[#] | 10.13 | 4.12 | 2.05 | 1.18 | 0.75 | 0.52 | 0.38 |
| 2-Butyldibenzo-thiophene | 2-butyldibenzo-thiophene | 7.58E+07 | 6.46E+04 | 1684.53[#] | 177.85[#] | 38.80 | 12.95 | 5.65 | 2.96 | 1.76 | 1.15 | 0.80 |
| 2-Pentyldibenzo-thiophene oxide | 2-pentyldibenzo-thiophene 5-oxide | 5.25E+04 | 227.33 | 19.57 | 5.00[*] | 2.15 | 1.25 | 0.87 | 0.69 | 0.60 | 0.58 | 0.63 |
| 2-Pentyldibenzo-thiophene sulfone | 2-pentyldibenzo-thiophene 5,5-dioxide | 1.07E+06 | 4590.61 | 274.96 | 44.35[#] | 12.15 | 4.62 | 2.19 | 1.21 | 0.75 | 0.51 | 0.37 |

TABLE 2B-continued

| Compound | | Solvent (Acetone W %/Water W %) | | | | | | | | | | |
|---|---|---|---|---|---|---|---|---|---|---|---|---|
| | | 0/100 | 10/90 | 20/80 | 30/70 | 40/60 | 50/50 | 60/40 | 70/30 | 80/20 | 90/10 | 100/0 |
| Common Name | IUPAC | Activity Coefficient | | | | | | | | | | |
| 2-Pentyldibenzo-thiophene | 2-pentyldibenzo-thiophene | 2.67E+08 | 1.38E+05 | 2815.56 | 256.93# | 50.91 | 15.87 | 6.59 | 3.31 | 1.91 | 1.21 | 0.83 |
| 1-Phenyldibenzo-thiophene oxide | 1-phenyldibenzo-thiophene 5-oxide | 1.17E+04 | 101.62 | 12.02* | 3.68* | 1.78 | 1.12 | 0.83 | 0.69 | 0.63 | 0.62 | 0.69 |
| 1-Phenyldibenzo-thiophene sulfone | 1-phenyldibenzo-thiophene 5,5-dioxide | 3.46E+05 | 2600.07 | 198.66# | 36.59# | 10.91 | 4.40 | 2.18 | 1.24 | 0.79 | 0.55 | 0.40 |
| 1-Phenyldibenzo-thiophene | 1-phenyldibenzo-thiophene | 4.77E+07 | 4.84E+04 | 1349.88# | 147.29# | 32.74 | 11.06 | 4.87 | 2.56 | 1.53 | 1.00 | 0.70 |
| 4-Phenyldibenzo-thiophene oxide | 4-phenyldibenzo-thiophene 5-oxide | 6.25E+04 | 373.87 | 33.44 | 8.20* | 3.32 | 1.80 | 1.17 | 0.86 | 0.70 | 0.62 | 0.61 |
| 4-Phenyldibenzo-thiophene sulfone | 4-phenyldibenzo-thiophene 5,5-dioxide | 3.59E+05 | 2629.76 | 194.47 | 35.14# | 10.37 | 4.16 | 2.05 | 1.17 | 0.74 | 0.51 | 0.38 |
| 4-Phenyldibenzo-thiophene | 4-phenyldibenzo-thiophene | 5.26E+07 | 5.09E+04 | 1359.61 | 143.33# | 31.03 | 10.27 | 4.45 | 2.31 | 1.37 | 0.89 | 0.62 |
| Dodecane | Dodecane | 6.02E+08 | 4.55E+05 | 1.28E+04 | 1495.10 | 355.60 | 127.10 | 58.60 | 32.00 | 19.70 | 13.20 | 9.40 |
| Naphthalene | bicyclo[4.4.0]deca-1,3,5,7,9-pentene | 5.55E+04 | 897.40 | 100.30 | 25.30 | 9.80 | 4.90 | 2.90 | 1.90 | 1.40 | 1.00 | 0.80 |
| Dibutyl sulfoxide | 1-butylsulfinyl-butane | 49.90 | 2.30* | 0.70 | 0.40 | 0.30 | 0.30 | 0.30 | 0.30 | 0.40 | 0.50 | 0.90 |
| Dibutyl sulfone | 1-butylsulfonyl-butane | 324.80 | 32.00# | 11.00 | 5.50 | 3.30 | 2.20 | 1.60 | 1.20 | 1.00 | 0.90 | 0.80 |
| Dibutyl sulfide | 1-butylsulfanyl-butane | 5.23E+05 | 4250.30# | 364.60 | 79.70 | 28.20 | 13.20 | 7.40 | 4.70 | 3.20 | 2.40 | 1.80 |
| Thiophene sulfide | tetrahydro-thiophene 1-oxide | 250.10 | 12.20 | 3.40 | 1.70 | 1.10 | 0.90 | 0.80 | 0.70 | 0.70 | 0.80 | 0.90 |
| Thiophene sulfone | tetrahydro-thiophene 1,1-dioxide | 6248.60 | 270.60 | 48.60 | 14.80 | 6.20 | 3.20 | 1.90 | 1.20 | 0.90 | 0.60 | 0.50 |
| Thiophene | Thiophene | 6.64E+05 | 3892.30 | 258.70 | 47.50 | 14.90 | 6.40 | 3.40 | 2.10 | 1.40 | 1.00 | 0.70 |
| Toluene | Methylbenzene | 2.00 | 1.00 | 0.80 | 0.80 | 0.80 | 0.90 | 0.90 | 1.00 | 1.10 | 1.30 | 1.60 |

Methanol Formulations

In another embodiment of the process described herein, the solvent formulation comprises an aqueous solution of methanol. An aqueous solution of methanol having a concentration of about 10 W % to about 70 W % is particularly useful as a selective solvent formulation for extraction of sulfoxide products. The level of extraction and the specific concentration of the methanol selective solvent formulation depend on factors including but not limited to the sulfur speciation of the feed hydrocarbon mixture and whether the target sulfoxide products to be extracted are non-bulky or bulky. For non-bulky sulfoxide products, the concentration of the aqueous methanol solution can be about 10 W % to about 30 W %, which will extract the non-bulky sulfoxide products, while minimizing co-extraction of certain sulfones, untreated organosulfur corn pounds, non-heteroatom aromatics and other hydrocarbons. For bulky sulfoxide products, the concentration of the aqueous methanol solution can be about 30 W % to about 70 W %, which will extract the bulky sulfoxide products, while minimizing co-extraction of certain sulfones, non-heteroatom aromatics, untreated organosulfur compounds and other hydrocarbons.

In an extractive simulation, COSMO-RS software was used to simulate γ for selective extraction of oxidized model A fuel by solvent formulations of aqueous methanol. Methanol is desirable as a polar organic solvent due to its low boiling point, thereby facilitating recovery and separation from the sulfoxide products.

Figure 6:
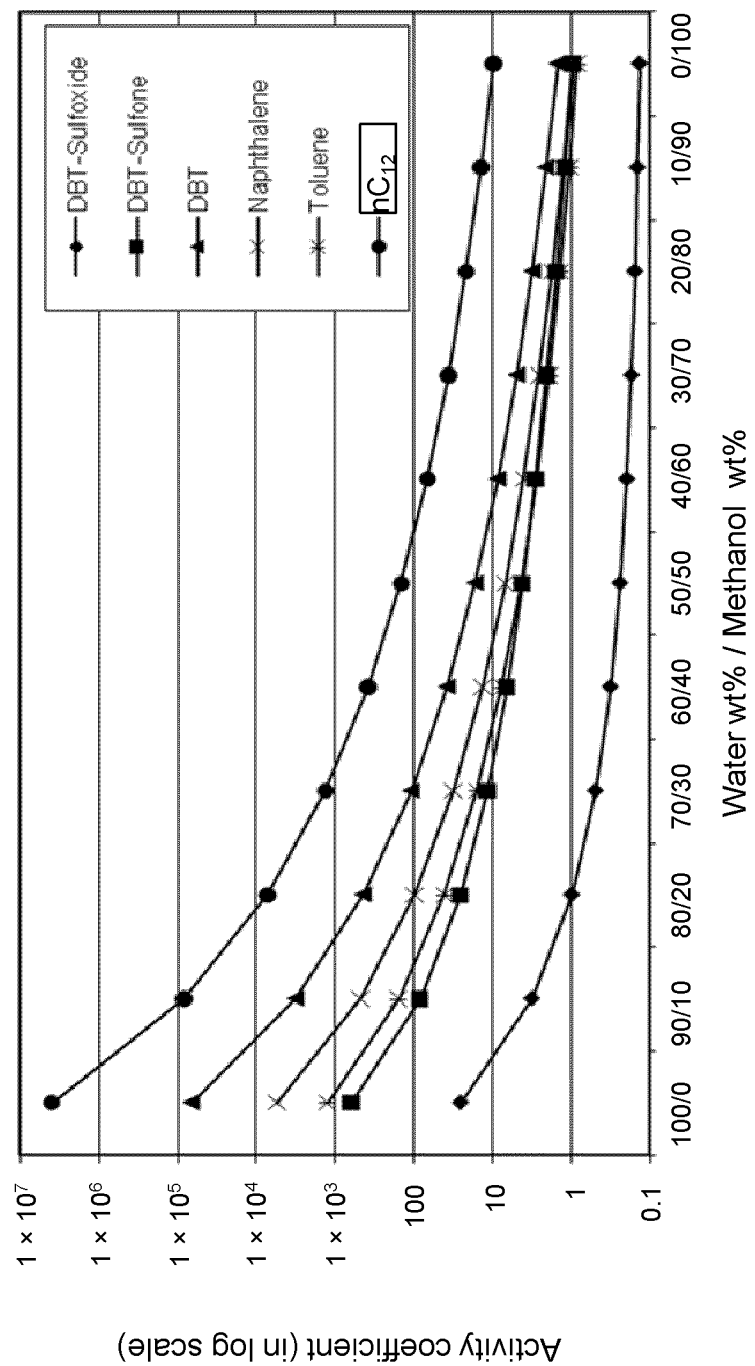
FIGS. 6, 7 and 8 are plots of computational models of the activity coefficient values for a range of concentrations of a methanol solvent formulation relative to sulfoxides of DBT, thiophene and dibutyl sulfide compounds, respectively, relative to other components in a hydrocarbon mixture.
Figure 7:
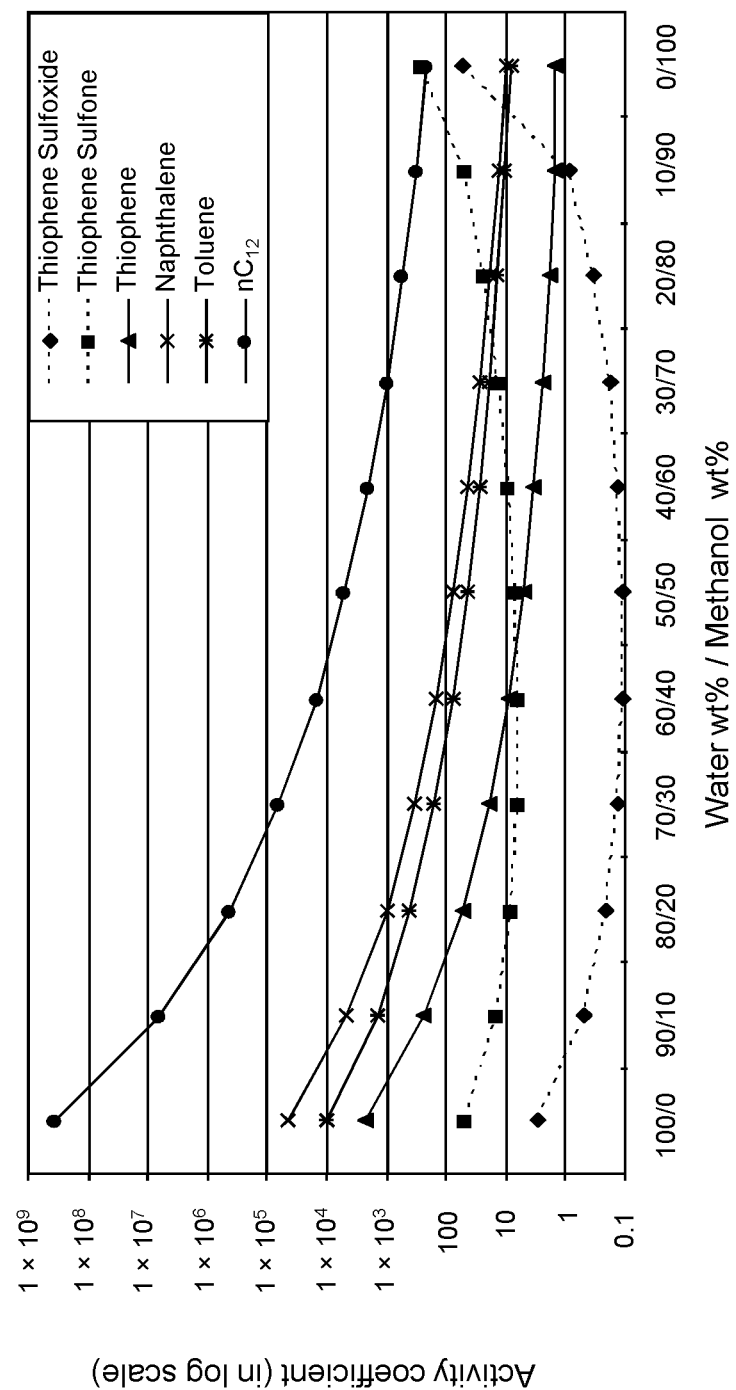
Figure 8:
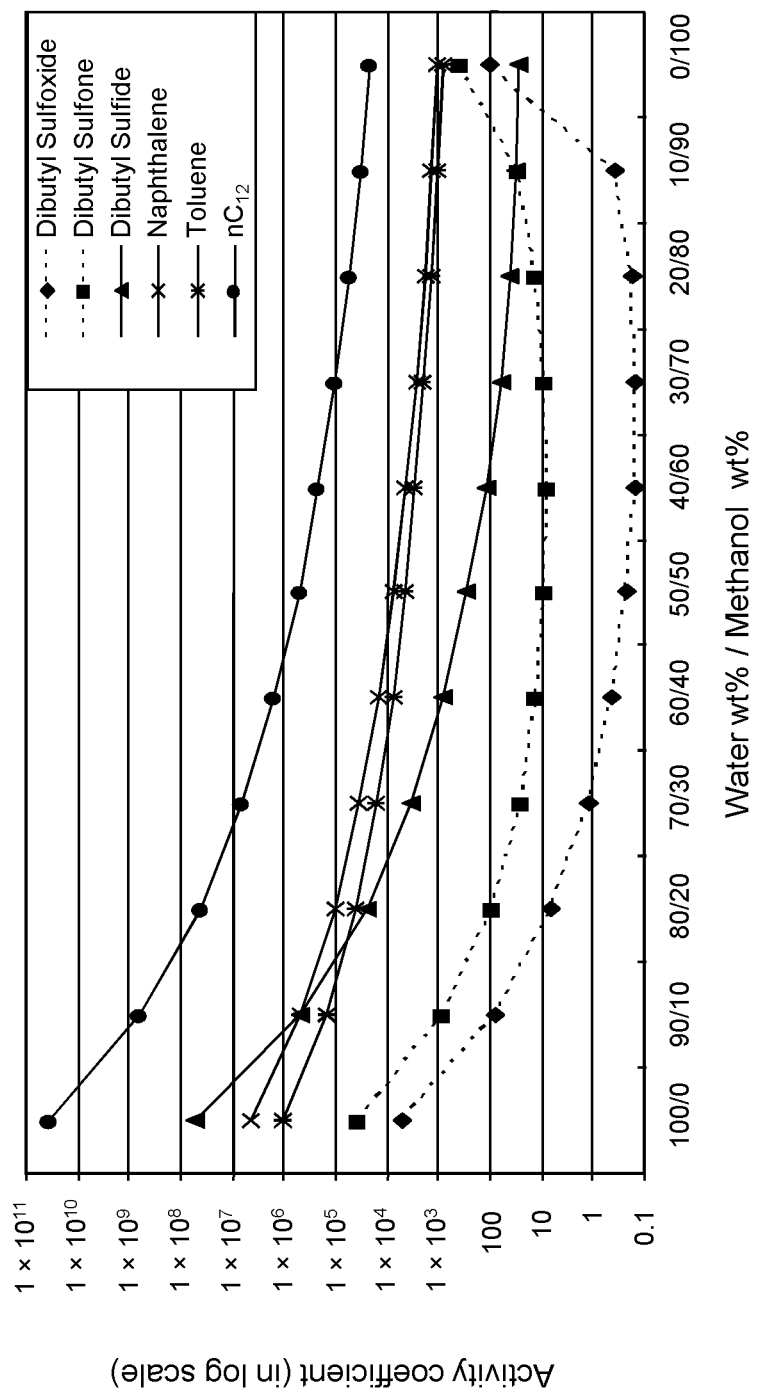

Table 3A illustrates the activity coefficient of different concentrations of aqueous methanol for the compounds listed. Based on the activity coefficient values in Table 3A, a useful aqueous methanol selective solvent formulation has a concentration of about 30 W % to about 70 W % for extraction of DBT sulfoxide with minimal co-extraction of certain sulfones, untreated organosulfur compounds, aromatics and other hydrocarbons, as shown in FIG. 6. An aqueous methanol selective solvent formulation of about 30 W % to about 70 W % is also useful for extraction of thiophene sulfoxide, thiophene sulfone, dibutyl sulfoxide and dibutyl sulfone. If the target sulfoxidation products are primarily thiophene sulfoxide and dibutyl sulfoxide, a suitable selective solvent formulation can be about 10 W % to about 30 W % aqueous methanol, as shown in FIGS. 7 and 8.

In another extraction simulation, COSMO-RS software was used to simulate γ for formulations of aqueous methanol as extraction solvents for oxidized model B fuel. The results are shown in Table 3B. Activity coefficient values as shown in Table 3B indicate that certain formulations of aqueous methanol will selectively extract bulky sulfoxide products while minimizing co-extraction of their corresponding sulfones and underlying organosulfur compounds. Based on the activity coefficient values in Table 3B, a useful methanol selective solvent formulation has a concentration of about 20 W % to about 60 W % for selective extraction of bulky sulfoxide products including alkyl and dialkyl derivatives of benzothiophenes and dibenzothiophenes.

In Table 3B, activity coefficients for targeted sulfoxides for which extraction is favored are marked with an asterisk ("*"), activity coefficients for non-targeted corresponding sulfones and the underlying organosulfur compounds for which co-extraction is minimized are marked with a pound symbol ("#").

Note that for extraction of certain bulky sulfoxide products, such as 6-methylbenzothiophene oxide and 2,6-dimethylbenzothiophene oxide, selective solvent formulations can contain as little as 10 W % methanol, but selective extraction of other bulky sulfoxide products will be very limited.

It is noted that although the activity coefficient values for certain high concentration methanol formulations indicate favorable extraction of certain bulky or non-bulky sulfoxidation products (including sulfoxides and sulfones), these high concentration methanol formulations (e.g., greater than 70 W %) also extract untargeted species and therefore are not particularly desirable for selective extraction of a broad array of organosulfur oxidation products.

TABLE 3A

| Compound | Solvent (Methanol W %/Water W %) | | | | | | | | | | |
|---|---|---|---|---|---|---|---|---|---|---|---|
| | 0/100 | 10/90 | 20/80 | 30/70 | 40/60 | 50/50 | 60/40 | 70/30 | 80/20 | 90/10 | 100/0 |
| | Activity Coefficient | | | | | | | | | | |
| dibenzothiophene 5-oxide (DBT sulfoxide) | 250.10 | 31.30 | 9.80 | 4.90 | 3.20 | 2.40 | 1.90 | 1.70 | 1.50 | 1.40 | 1.30 |
| dibenzothiophene 5,5-dioxide (DBT sulfone) | 6248.00 | 835.50 | 256.10 | 116.90 | 65.80 | 41.70 | 28.60 | 20.60 | 15.40 | 11.90 | 9.40 |
| dibenzothiophene (DBT) | 6.64E+05 | 3.15E+04 | 4355.00 | 1074.00 | 375.20 | 164.60 | 84.70 | 48.90 | 30.80 | 20.70 | 14.70 |
| 1-butylsulfinyl-butane (Dibutyl Sulfoxide) | 49.90 | 5.40 | 1.50 | 0.70 | 0.50 | 0.30 | 0.30 | 0.30 | 0.20 | 0.20 | 0.20 |
| 1-butylsulfonyl-butane (Dibutyl Sulfone) | 324.80 | 56.50 | 22.30 | 13.10 | 9.40 | 7.40 | 6.30 | 5.50 | 4.80 | 4.30 | 3.90 |
| 1-butylsulfanyl-butane (Dibutyl Sulfide) | 5.23E+05 | 2.49E+04 | 3611.00 | 956.20 | 359.40 | 168.90 | 92.40 | 56.40 | 37.20 | 26.20 | 19.30 |
| Thiophene Sulfoxide | 122.40 | 44.00 | 23.80 | 15.70 | 11.50 | 8.90 | 7.20 | 6.00 | 5.10 | 4.40 | 3.80 |
| Thiophene Sulfone | 42.80 | 25.60 | 19.70 | 16.60 | 14.30 | 12.50 | 10.90 | 9.50 | 8.20 | 7.20 | 6.30 |
| Thiophene | 1819.00 | 358.70 | 122.10 | 56.20 | 31.20 | 19.50 | 13.30 | 9.60 | 7.30 | 5.80 | 4.70 |
| Naphthalene | 5552.00 | 4789.10 | 974.70 | 315.50 | 134.90 | 69.20 | 40.40 | 25.80 | 17.70 | 12.80 | 9.70 |
| Toluene | 1.26E+04 | 1574.10 | 407.80 | 157.00 | 76.60 | 43.70 | 27.70 | 19.00 | 13.90 | 10.60 | 8.40 |
| $nC_{12}$ | 3.99E+07 | 8.42E+05 | 7.25E+04 | 1.33E+04 | 3798.00 | 1451.00 | 675.00 | 363.00 | 216.60 | 140.20 | 96.70 |

TABLE 3B

| Compound | | Solvent (Methanol W %/Water W %) | | | | | |
|---|---|---|---|---|---|---|---|
| Common Name | IUPAC | 0/100 | 10/90 | 20/80 | 30/70 | 40/60 | 50/50 |
| | | Activity Coefficient | | | | | |
| 6-Methylbenzothiophene oxide | 6-methyl-1-benzo(b)thiophene 1-oxide | 47.00 | 8.64* | 3.42* | 2.01* | 1.47* | 1.21* |
| 6-Methylbenzothiophene sulfone | 6-methyl-1-benzo(b)thiophene 1,1-dioxide | 988.00 | 206.02# | 83.59# | 46.52# | 30.42# | 21.77# |
| 6-Methylbenzothiophene | 6-methyl-1-benzo(b)thiophene | 1.20E+05 | 8531.02# | 1523.93# | 450.32# | 180.31# | 88.16# |
| 2,6-Dimethylbenzothiophene oxide | 2,6-dimethyl-1-benzo(b)thiophene 1-oxide | 88.00 | 12.15* | 4.03* | 2.11* | 1.42* | 1.11* |
| 2,6-Dimethylbenzothiophene sulfone | 2,6-dimethyl-1-benzo(b)thiophene 1,1-dioxide | 1967.00 | 313.60# | 108.81# | 55.00# | 33.79# | 23.18# |
| 2,6-Dimethylbenzothiophene | 2,6-dimethyl-1-benzo(b)thiophene | 3.87E+05 | 2.04E+04# | 3008.12# | 780.51# | 284.45# | 129.55# |
| 2,3,6-Trimethylbenzothiophene-oxide | 2,3,6-trimethyl-1-benzo(b)thiophene 1-oxide | 313.00 | 31.43 | 8.53* | 3.89* | 2.36* | 1.70* |
| 2,3,6-Trimethylbenzothiophene sulfone | 2,3,6-trimethyl-1-benzo(b)thiophene 1,1-dioxide | 5917.00 | 689.22 | 195.80# | 86.31# | 48.04# | 30.62# |
| 2,3,6-Trimethylbenzothiophene | 2,3,6-trimethyl-1-benzo(b)thiophene | 1.17E+06 | 4.70E+04 | 5852.93# | 1353.94# | 454.44# | 194.61# |
| Dibenzothiophene oxide | dibenzothiophene 5-oxide | 251.00 | 31.30 | 9.80* | 4.90* | 3.20* | 2.40* |
| Dibenzothiophene sulfone | dibenzothiophene 5,5-dioxide | 6267.00 | 835.50 | 256.10# | 116.90# | 65.80# | 41.70# |
| Dibenzothiophene | dibenzothiophene | 6.67E+05 | 3.15E+04 | 4355.30# | 1074.00# | 375.20# | 164.60# |
| 4-Methyldibenzothiophene oxide | 4-methyldibenzothiophene 5-oxide | 718.00 | 65.39 | 16.66 | 7.22* | 4.20* | 2.91* |
| 4-Methyldibenzothiophene sulfone | 4-methyldibenzothiophene 5,5-dioxide | 1.79E+04 | 1683.15 | 412.99 | 162.14# | 82.02# | 48.22# |
| 4-Methyldibenzothiophene | 4-methyldibenzothiophene | 1.84E+06 | 6.58E+04 | 7615.56 | 1668.71# | 536.41# | 221.64# |
| 3,6-Dimethyldibenzothiophene oxide | 3,6-dimethyldibenzothiophene 5-oxide | 1664.00 | 103.44 | 21.82 | 8.36* | 4.46* | 2.91* |

TABLE 3B-continued

| Common Name | IUPAC | | | | | |
|---|---|---|---|---|---|---|
| 3,6-Dimethyldibenzothiophene sulfone | 3,6-dimethyldibenzothiophene 5,5-dioxide | 4.41E+04 | 2826.41 | 593.29 | 211.11[#] | 99.99[#] | 56.15[#] |
| 3,6-Dimethyldibenzothiophene | 3,6-dimethyldibenzothiophene | 5.81E+06 | 1.58E+05 | 1.51E+04 | 2905.71[#] | 849.28[#] | 326.62[#] |
| 4,6-Dimethyldibenzothiophene oxide | 4,6-dimethyldibenzothiophene 5-oxide | 2468.00 | 112.28 | 23.74 | 9.09[*] | 4.85[*] | 3.16[*] |
| 4,6-Dimethyldibenzothiophene sulfone | 4,6-dimethyldibenzothiophene 5,5-dioxide | 3.74E+04 | 3138.83 | 649.28 | 228.27[#] | 107.06[#] | 59.63[#] |
| 4,6-Dimethyldibenzothiophene | 4,6-dimethyldibenzothiophene | 5.04E+06 | 1.55E+05 | 1.49E+04 | 2875.57[#] | 843.51[#] | 325.30[#] |
| 2,4-Dimethyldibenzothiophene oxide | 2,4-dimethyldibenzothiophene 5-oxide | 1542.00 | 165.30 | 34.52 | 13.01[*] | 6.81[*] | 4.34[*] |
| 2,4-Dimethyldibenzothiophene sulfone | 2,4-dimethyldibenzothiophene 5,5-dioxide | 3.90E+04 | 2732.76 | 575.32 | 204.94[#] | 97.20[#] | 54.71[#] |
| 2,4-Dimethyldibenzothiophene | 2,4-dimethyldibenzothiophene | 6.02E+06 | 1.39E+05 | 1.37E+04 | 2702.30[#] | 804.33[#] | 313.82[#] |
| 2,4,7-Trimethyldibenzothiophene oxide | 2,4,7-trimethyldibenzothiophene 5-oxide | 4095.00 | 203.36 | 35.61 | 12.04[*] | 5.89[*] | 3.60[*] |
| 2,4,7-Trimethyldibenzothiophene sulfone | 2,4,7-trimethyldibenzothiophene 5,5-dioxide | 9.72E+04 | 5321.64 | 945.96 | 302.83[#] | 133.56[#] | 71.32[#] |
| 2,4,7-Trimethyldibenzothiophene | 2,4,7-trimethyldibenzothiophene | 2.05E+07 | 3.98E+05 | 3.14E+04 | 5291.32[#] | 1407.93[#] | 504.49[#] |
| 4-Ethyldibenzothiophene oxide | 4-ethyldibenzothiophene 5-oxide | 1706.00 | 117.52 | 25.17 | 9.71[*] | 5.20[*] | 3.39[*] |
| 4-Ethyldibenzothiophene sulfone | 4-ethyldibenzothiophene 5,5-dioxide | 5.43E+04 | 3744.51 | 749.52 | 254.85[#] | 115.83[#] | 62.73[#] |
| 4-Ethyldibenzothiophene | 4-ethyldibenzothiophene | 5.28E+06 | 1.42E+05 | 1.38E+04 | 2690.48[#] | 794.24[#] | 307.85[#] |
| 4-Propyldibenzothiophene oxide | 4-propyldibenzothiophene 5-oxide | 4103.00 | 210.79 | 37.63 | 12.85[*] | 6.31[*] | 3.86[*] |
| 4-Propyldibenzothiophene sulfone | 4-propyldibenzothiophene 5,5-dioxide | 1.60E+05 | 8114.04 | 1338.67 | 398.99[#] | 164.81[#] | 83.04[#] |
| 4-Propyldibenzothiophene | 4-propyldibenzothiophene | 1.72E+07 | 3.40E+05 | 2.72E+04 | 4625.07[#] | 1237.88[#] | 445.33[#] |
| 2-Butyldibenzothiophene oxide | 2-butyldibenzothiophene 5-oxide | 1.43E+04 | 502.20 | 70.76 | 20.60 | 9.03[*] | 5.07[*] |
| 2-Butyldibenzothiophene sulfone | 2-butyldibenzothiophene 5,5-dioxide | 3.38E+05 | 1.33E+04 | 1900.63 | 520.80 | 203.69[#] | 98.74[#] |
| 2-Butyldibenzothiophene | 2-butyldibenzothiophene | 7.58E+07 | 1.03E+06 | 6.45E+04 | 9267.92 | 2188.34[#] | 714.84[#] |
| 2-Pentyldibenzothiophene oxide | 2-pentyldibenzothiophene 5-oxide | 5.25E+04 | 1344.27 | 155.01 | 39.28 | 15.55[*] | 8.07[*] |
| 2-Pentyldibenzothiophene sulfone | 2-pentyldibenzothiophene 5,5-dioxide | 1.07E+06 | 3.08E+04 | 3626.00 | 867.33 | 307.18[#] | 138.09[#] |
| 2-Pentyldibenzothiophene | 2-pentyldibenzothiophene | 2.67E+08 | 2.64E+06 | 1.35E+05 | 1.70E+04 | 3619.77[#] | 1095.31[#] |
| 1-Phenyldibenzothiophene oxide | 1-phenyldibenzothiophene 5-oxide | 1.17E+04 | 482.62 | 74.97 | 23.24 | 10.62[*] | 6.14[*] |
| 1-Phenyldibenzothiophene sulfone | 1-phenyldibenzothiophene 5,5-dioxide | 3.46E+05 | 1.48E+04 | 2231.04 | 626.34 | 247.84[#] | 120.69[#] |
| 1-Phenyldibenzothiophene | 1-phenyldibenzothiophene | 4.77E+07 | 7.44E+05 | 5.11E+04 | 7787.89 | 1917.06[#] | 645.22[#] |
| 4-Phenyldibenzothiophene oxide | 4-phenyldibenzothiophene 5-oxide | 6.25E+04 | 2209.02 | 300.54 | 82.49 | 33.71 | 17.59 |
| 4-Phenyldibenzothiophene sulfone | 4-phenyldibenzothiophene 5,5-dioxide | 3.59E+05 | 1.57E+04 | 2341.14 | 649.49 | 253.73 | 122.13 |
| 4-Phenyldibenzothiophene | 4-phenyldibenzothiophene | 5.26E+07 | 8.09E+05 | 5.48E+04 | 8252.85 | 2006.56 | 667.57 |
| Dodecane | Dodecane | 6.02E+08 | 8.42E+05 | 7.25E+04 | 13274.20 | 3798.80 | 1451.10 |
| Naphthalene | bicyclo[4.4.0]deca-1,3,5,7,9-pentene | 5.55E+04 | 4789.10 | 974.70 | 315.50 | 134.90 | 69.20 |
| Dibutyl sulfoxide | 1-butylsulfinyl-butane | 49.90 | 5.40[#] | 1.50[#] | 0.70 | 0.50 | 0.30 |
| Dibutyl sulfone | 1-butylsulfonyl-butane | 324.80 | 56.50[*] | 22.30[*] | 13.10 | 9.40 | 7.40 |
| Dibutyl sulfide | 1-butylsulfanyl-butane | 5.23E+05 | 24853.60[*] | 3611.60[*] | 956.20 | 359.40 | 168.90 |
| Thiophene sulfide | tetrahydrothiophene 1-oxide | 2.00 | 44.00 | 23.80 | 15.70[#] | 11.50 | 8.90 |
| Thiophene sulfone | tetrahydrothiophene 1,1-dioxide | 43.10 | 25.60 | 19.70 | 16.60[*] | 14.30 | 12.50 |
| Thiophene | Thiophene | 1819.20 | 358.70 | 122.10 | 56.20[*] | 31.20 | 19.50 |
| Toluene | Methylbenzene | 1.26E+04 | 1574.10 | 407.80 | 157.00 | 76.60 | 43.70 |

| | | Solvent (Methanol W %/Water W %) | | | | |
|---|---|---|---|---|---|---|
| Compound | | 60/40 | 70/30 | 80/20 | 90/10 | 100/0 |
| Common Name | IUPAC | Activity Coefficient | | | | |
| 6-Methylbenzothiophene oxide | 6-methyl-1-benzo(b)thiophene 1-oxide | 1.07[*] | 0.99 | 0.95 | 0.92 | 0.90 |
| 6-Methylbenzothiophene sulfone | 6-methyl-1-benzo(b)thiophene 1,1-dioxide | 16.45[#] | 12.89 | 10.37 | 8.52 | 7.12 |
| 6-Methylbenzothiophene | 6-methyl-1-benzo(b)thiophene | 49.48[#] | 30.71 | 20.56 | 14.60 | 10.88 |

TABLE 3B-continued

| | | | | | | |
|---|---|---|---|---|---|---|
| 2,6-Dimethylbenzothiophene oxide | 2,6-dimethyl-1-benzo(b)thiophene 1-oxide | 0.94* | 0.85 | 0.79 | 0.75 | 0.73 |
| 2,6-Dimethylbenzothiophene sulfone | 2,6-dimethyl-1-benzo(b)thiophene 1,1-dioxide | 17.00# | 13.04 | 10.32 | 8.37 | 6.92 |
| 2,6-Dimethylbenzothiophene | 2,6-dimethyl-1-benzo(b)thiophene | 68.79# | 40.84 | 26.38 | 18.17 | 13.20 |
| 2,3,6-Trimethylbenzothiophene-oxide | 2,3,6-trimethyl-1-benzo(b)thiophene 1-oxide | 1.35* | 1.15 | 1.03 | 0.95 | 0.89 |
| 2,3,6-Trimethylbenzothiophene sulfone | 2,3,6-trimethyl-1-benzo(b)thiophene 1,1-dioxide | 21.24# | 15.59 | 11.93 | 9.40 | 7.61 |
| 2,3,6-Trimethylbenzothiophene | 2,3,6-trimethyl-1-benzo(b)thiophene | 98.51# | 56.32 | 35.27 | 23.69 | 16.85 |
| Dibenzothiophene oxide | dibenzothiophene 5-oxide | 1.90* | 1.70* | 1.50 | 1.40 | 1.30 |
| Dibenzothiophene sulfone | dibenzothiophene 5,5-dioxide | 28.60# | 20.60# | 15.40 | 11.90 | 9.40 |
| Dibenzothiophene | dibenzothiophene | 84.70# | 48.90# | 30.80 | 20.70 | 14.70 |
| 4-Methyldibenzothiophene oxide | 4-methyldibenzothiophene 5-oxide | 2.25* | 1.86* | 1.62 | 1.45 | 1.33 |
| 4-Methyldibenzothiophene sulfone | 4-methyldibenzothiophene 5,5-dioxide | 31.21# | 21.59# | 15.69 | 11.83 | 9.20 |
| 4-Methyldibenzothiophene | 4-methyldibenzothiophene | 108.84# | 60.61# | 37.09 | 24.41 | 17.06 |
| 3,6-Dimethyldibenzothiophene oxide | 3,6-dimethyldibenzothiophene 5-oxide | 2.15* | 1.72* | 1.46* | 1.28 | 1.16 |
| 3,6-Dimethyldibenzothiophene sulfone | 3,6-dimethyldibenzothiophene 5,5-dioxide | 35.15# | 23.71# | 16.89# | 12.54 | 9.64 |
| 3,6-Dimethyldibenzothiophene | 3,6-dimethyldibenzothiophene | 151.65# | 80.75# | 47.65# | 30.42 | 20.73 |
| 4,6-Dimethyldibenzothiophene oxide | 4,6-dimethyldibenzothiophene 5-oxide | 2.33* | 1.86* | 1.57* | 1.38 | 1.24 |
| 4,6-Dimethyldibenzothiophene sulfone | 4,6-dimethyldibenzothiophene 5,5-dioxide | 37.08# | 24.88# | 17.64# | 13.05 | 10.00 |
| 4,6-Dimethyldibenzothiophene | 4,6-dimethyldibenzothiophene | 151.37# | 80.75# | 47.72# | 30.51 | 20.81 |
| 2,4-Dimethyldibenzothiophene oxide | 2,4-dimethyldibenzothiophene 5-oxide | 3.14* | 2.46* | 2.04* | 1.76 | 1.56 |
| 2,4-Dimethyldibenzothiophene sulfone | 2,4-dimethyldibenzothiophene 5,5-dioxide | 34.36# | 23.27# | 16.65# | 12.42 | 9.60 |
| 2,4-Dimethyldibenzothiophene | 2,4-dimethyldibenzothiophene | 147.43# | 79.28# | 47.17# | 30.34 | 20.79 |
| 2,4,7-Trimethyldibenzothiophene oxide | 2,4,7-trimethyldibenzothiophene 5-oxide | 2.53* | 1.95* | 1.60* | 1.38 | 1.22 |
| 2,4,7-Trimethyldibenzothiophene sulfone | 2,4,7-trimethyldibenzothiophene 5,5-dioxide | 43.02# | 28.21# | 19.66# | 14.34 | 10.86 |
| 2,4,7-Trimethyldibenzothiophene | 2,4,7-trimethyldibenzothiophene | 221.66# | 112.94# | 64.29# | 39.85 | 26.48 |
| 4-Ethyldibenzothiophene oxide | 4-ethyldibenzothiophene 5-oxide | 2.50* | 2.00* | 1.69* | 1.48 | 1.33 |
| 4-Ethyldibenzothiophene sulfone | 4-ethyldibenzothiophene 5,5-dioxide | 38.06# | 24.99# | 17.40# | 12.66 | 9.57 |
| 4-Ethyldibenzothiophene | 4-ethyldibenzothiophene | 143.83# | 76.98# | 45.61# | 29.23 | 19.97 |
| 4-Propyldibenzothiophene oxide | 4-propyldibenzothiophene 5-oxide | 2.71* | 2.09* | 1.71* | 1.46 | 1.29 |
| 4-Propyldibenzothiophene sulfone | 4-propyldibenzothiophene 5,5-dioxide | 47.59# | 29.86# | 20.02# | 14.12 | 10.40 |
| 4-Propyldibenzothiophene | 4-propyldibenzothiophene | 196.19# | 100.14# | 57.07# | 35.40 | 23.54 |
| 2-Butyldibenzothiophene oxide | 2-butyldibenzothiophene 5-oxide | 3.34* | 2.44* | 1.92* | 1.59 | 1.36 |
| 2-Butyldibenzothiophene sulfone | 2-butyldibenzothiophene 5,5-dioxide | 54.95# | 33.66# | 22.11# | 15.32 | 11.09 |
| 2-Butyldibenzothiophene | 2-butyldibenzothiophene | 291.61# | 139.81# | 75.64# | 44.91 | 28.77 |
| 2-Pentyldibenzothiophene oxide | 2-pentyldibenzothiophene 5-oxide | 4.99* | 3.46* | 2.61* | 2.08* | 1.73 |
| 2-Pentyldibenzothiophene sulfone | 2-pentyldibenzothiophene 5,5-dioxide | 72.41# | 42.27# | 26.70# | 17.89# | 12.61 |
| 2-Pentyldibenzothiophene | 2-pentyldibenzothiophene | 420.66# | 192.10# | 99.86# | 57.33# | 35.70 |
| 1-Phenyldibenzothiophene oxide | 1-phenyldibenzothiophene 5-oxide | 4.13* | 3.06* | 2.43* | 2.02* | 1.74 |
| 1-Phenyldibenzothiophene sulfone | 1-phenyldibenzothiophene 5,5-dioxide | 67.23# | 41.14# | 26.97# | 18.64# | 13.47 |
| 1-Phenyldibenzothiophene | 1-phenyldibenzothiophene | 269.16# | 131.25# | 71.95# | 43.16# | 27.87 |
| 4-Phenyldibenzothiophene oxide | 4-phenyldibenzothiophene 5-oxide | 10.75* | 7.31* | 5.37* | 4.16* | 3.36 |
| 4-Phenyldibenzothiophene sulfone | 4-phenyldibenzothiophene 5,5-dioxide | 67.37# | 40.89# | 26.63# | 18.31# | 13.17 |
| 4-Phenyldibenzothiophene | 4-phenyldibenzothiophene | 275.51# | 133.03# | 72.27# | 42.99# | 27.55 |
| Dodecane | Dodecane | 675.90 | 363.00 | 216.60 | 140.20 | 96.70 |

TABLE 3B-continued

| | | | | | | |
|---|---|---|---|---|---|---|
| Naphthalene | bicyclo[4.4.0]deca-1,3,5,7,9-pentene | 40.40 | 25.80 | 17.70 | 12.80 | 9.70 |
| Dibutyl sulfoxide | 1-butylsulfinyl-butane | 0.30 | 0.30 | 0.20 | 0.20 | 0.20 |
| Dibutyl sulfone | 1-butylsulfonyl-butane | 6.30 | 5.50 | 4.80 | 4.30 | 3.90 |
| Dibutyl sulfide | 1-butylsulfanyl-butane | 92.40 | 56.40 | 37.20 | 26.20 | 19.30 |
| Thiophene sulfide | tetrahydrothiophene 1-oxide | 7.20 | 6.00 | 5.10 | 4.40 | 3.80 |
| Thiophene sulfone | tetrahydrothiophene 1,1-dioxide | 10.90 | 9.50 | 8.20 | 7.20 | 6.30 |
| Thiophene | Thiophene | 13.30 | 9.60 | 7.30 | 5.80 | 4.70 |
| Toluene | Methylbenzene | 27.70 | 19.00 | 13.90 | 10.60 | 8.40 |

Acetonitrile Formulations

In still another embodiment of the present invention, the solvent formulation comprises an aqueous solution of acetonitrile. An aqueous solution of acetonitrile having a concentration of about 2.5 W % to about 40 W % is particularly useful as a selective solvent formulation for extraction of sulfoxide products, and an aqueous solution of acetonitrile having a concentration of about 40 W % to about 60 W % is particularly useful for extraction of bulky sulfoxidation products, i.e., sulfoxides and sulfones. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. For non-bulky sulfoxide products, the concentration of the aqueous acetonitrile solution can be about 2.5 W % to about 30 W %, which will extract the non-bulky sulfoxides and also thiophene sulfone, while minimizing co-extraction of other sulfones, untreated organosulfur compounds, non-heteroatom aromatics and other hydrocarbons. For bulky sulfoxide products and/or bulky sulfoxidation products, the concentration of the aqueous acetonitrile solution can be about 30 W % to about 60 W %, which will extract the bulky sulfoxide products and/or bulky sulfoxidation products, while minimizing co-extraction of non-heteroatom aromatics, untreated organosulfur compounds and other hydrocarbons.

In an extractive simulation, COSMO-RS software was used to simulate γ for selective extraction of oxidized model A fuel by solvent formulations of aqueous acetonitrile. Acetonitrile is desirable as a polar organic solvent due to its low boiling point, thereby facilitating recovery and separation from the sulfoxide products or the sulfoxidation products.

Figure 9:
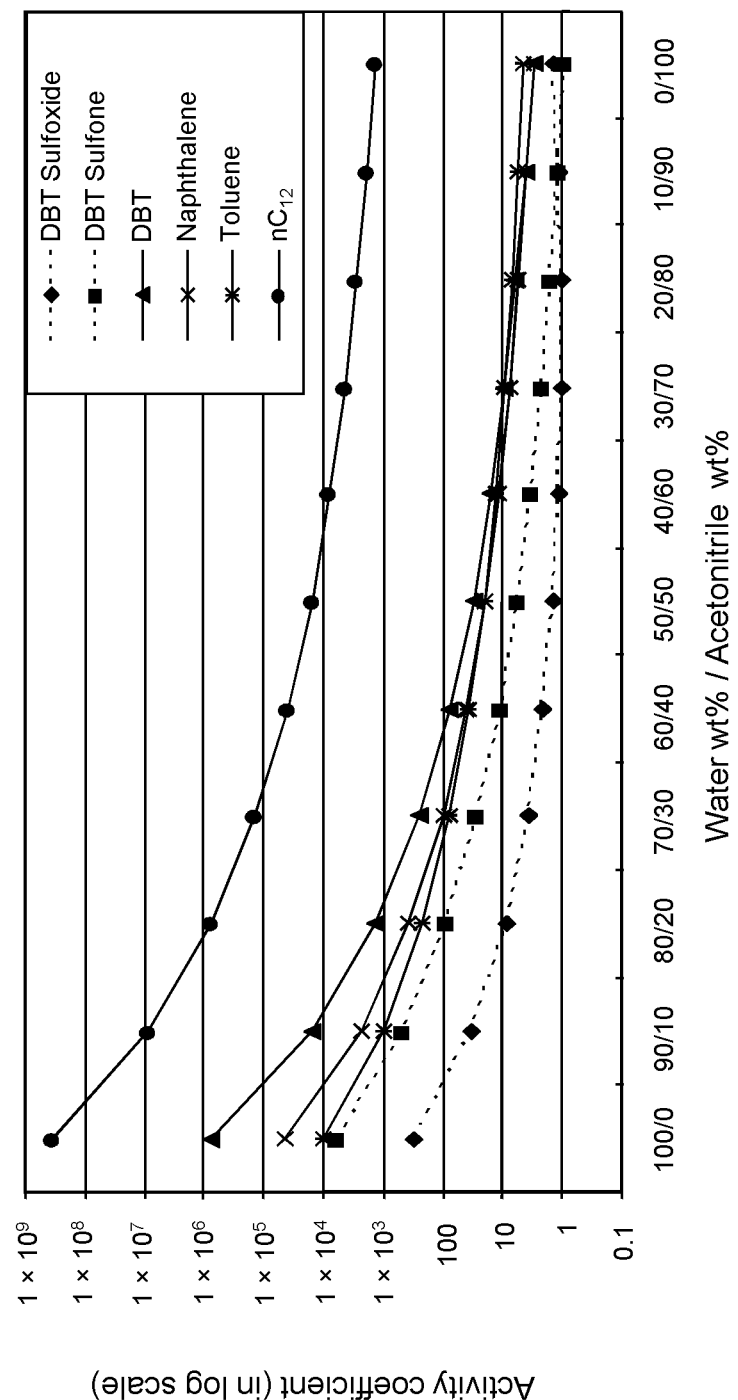
FIGS. 9, 10 and 11 are plots of computational models of the activity coefficient values for a range of concentrations of an acetonitrile solvent formulation for sulfoxidation products of DBT, thiophene and dibutyl sulfide compounds, respectively, relative to other components in a hydrocarbon mixture.
Figure 10:
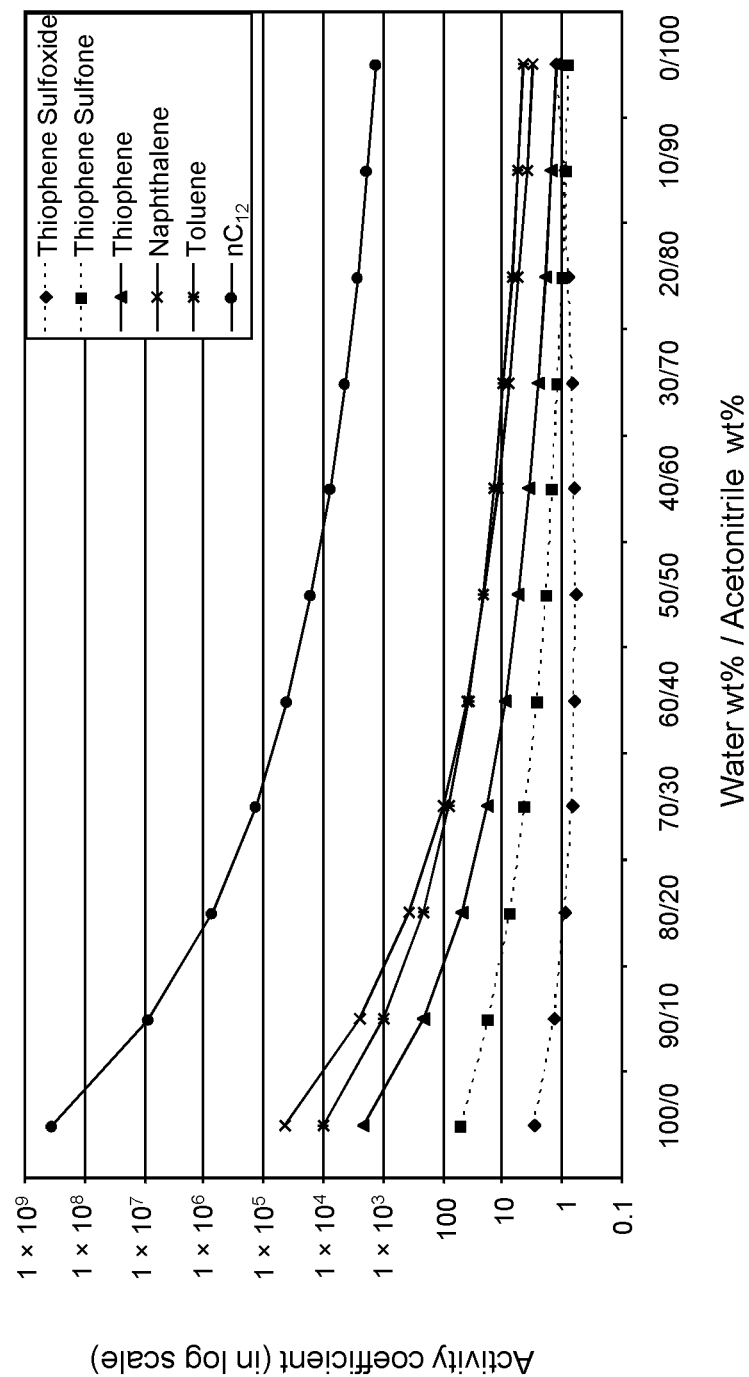
Figure 11:
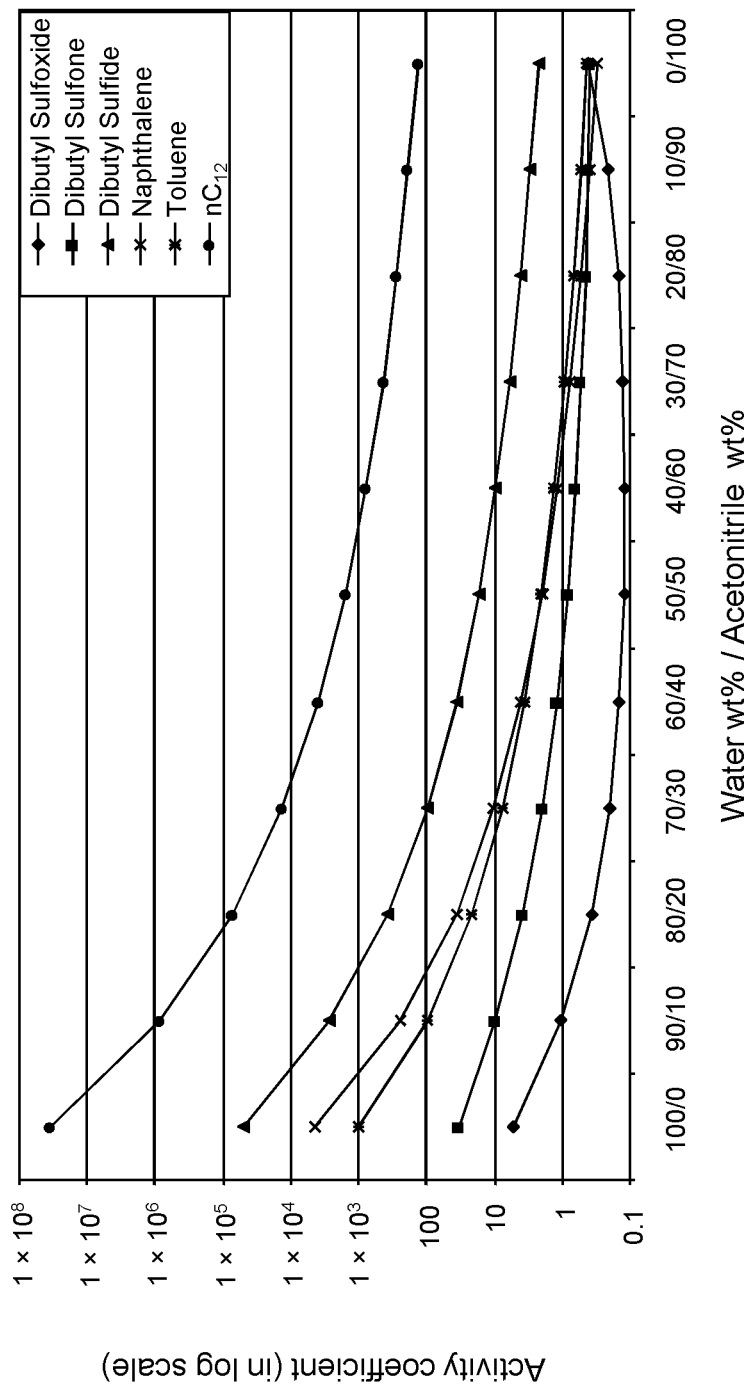

Table 4A illustrates the activity coefficient of different concentrations of aqueous acetonitrile. Based on the activity coefficient values in Table 4A, a useful aqueous acetonitrile selective solvent formulation has a concentration of about 20 W % to about 40 W % for extraction of DBT sulfoxide, with minimal co-extraction of certain sulfones, untreated organosulfur compounds, aromatics and other hydrocarbons, as shown in FIG. 9. It is also apparent from FIG. 9 and the data in Table 4A that a suitable concentration of acetonitrile is about 40 W % to about 60 W % for extraction of DBT sulfoxide combined with DBT sulfone, with minimal co-extraction of aromatics, untreated organosulfur compounds and other hydrocarbons. An aqueous acetonitrile selective solvent formulation of about 40 W % to about 60 W % is also useful for extraction of thiophene sulfoxide, thiophene sulfone, dibutyl sulfoxide and dibutyl sulfone. If the target species are primarily non-bulky sulfoxide products such as thiophene sulfoxide and dibutyl sulfoxide, and also thiophene sulfone, a suitable selective solvent formulation can be about 5 W % to about 20 W % aqueous acetonitrile, as shown in FIGS. 10 and 11.

In another extraction simulation, COSMO-RS software was used to simulate γ for formulations of aqueous acetonitrile as extraction solvents for oxidized model B fuel. The results are shown in Table 4B. Activity coefficient values as shown in Table 4B indicate that certain formulations of aqueous acetonitrile will selectively extract bulky sulfoxide products while minimizing co-extraction of their corresponding sulfones and underlying organosulfur compounds. In addition, activity coefficient values as shown in Table 4B indicate that certain formulations of aqueous acetonitrile will selectively extract bulky sulfoxidation products, including sulfoxides and sulfones, with minimal co-extraction of aromatics, untreated organosulfur compounds and other hydrocarbons. Based on the activity coefficient values in Table 4B, a useful acetonitrile selective solvent formulation has a concentration of about 10 W % to about 40 W % for selective extraction of bulky sulfoxide products including alkyl and dialkyl derivatives of benzothiophenes and dibenzothiophenes. In addition, aqueous acetonitrile selective solvent formulations of about 40 W %) to about 60 W % are also useful for extraction of bulky sulfoxidation products including sulfoxides and sulfones with minimal co-extraction of aromatics, untreated organosulfur compounds and other hydrocarbons.

In Table 4B, activity coefficients for targeted sulfoxides for which extraction is favored are marked with an asterisk ("*"), activity coefficients for non-targeted underlying organosulfur compounds and in certain cases corresponding sulfones for which co-extraction is minimized are marked with a pound symbol ("#"), Furthermore, activity coefficients for targeted sulfones for which extraction is favored (i.e., in combination with corresponding sulfoxides) are marked with a letter "C".

It is noted that although the activity coefficient values for certain high concentration acetonitrile formulations indicate favorable extraction of certain bulky or non-bulky sulfoxidation products (including sulfoxides and sulfones), such as products of 2-butyldibenzothiophene, 2-pentyldibenzothiophene and dibutyl sulfide, these high concentration acetonitrile formulations (e.g., greater than 60 W %) also extract untargeted species and therefore are not particularly desirable for selective extraction of a broad array of organosulfur oxidation products.

TABLE 4A

| Compound | Solvent (Acetonitrile W %/Water W %) | | | | | | | | | | |
|---|---|---|---|---|---|---|---|---|---|---|---|
| | 0/100 | 10/90 | 20/80 | 30/70 | 40/60 | 50/50 | 60/40 | 70/30 | 80/20 | 90/10 | 100/0 |
| | Activity Coefficient | | | | | | | | | | |
| dibenzothiophene 5-oxide (DBT sulfoxide) | 321.00 | 34.10 | 8.41 | 3.56 | 2.08 | 1.46 | 1.19 | 1.07 | 1.05 | 1.14 | 1.48 |
| dibenzothiophene 5,5-dioxide (DBT sulfone) | 6063.00 | 492.70 | 87.40 | 26.00 | 10.70 | 5.47 | 3.25 | 2.14 | 1.52 | 1.16 | 0.93 |
| dibenzothiophene (DBT) | 7.90E+05 | 1.57E+04 | 1300.00 | 247.00 | 75.90 | 31.50 | 16.00 | 9.21 | 5.93 | 4.10 | 2.97 |
| 1-butylsulfinyl-butane (Dibutyl Sulfoxide) | 51.40 | 10.40 | 3.71 | 2.03 | 1.45 | 1.22 | 1.17 | 1.26 | 1.49 | 2.05 | 4.10 |
| 1-butylsulfonyl-butane (Dibutyl Sulfone) | 337.00 | 99.50 | 38.50 | 19.70 | 12.10 | 8.41 | 6.42 | 5.26 | 4.53 | 4.06 | 3.90 |
| 1-butylsulfanyl-butane (Dibutyl Sulfide) | 5.04E+05 | 2.72E+04 | 3752.00 | 963.00 | 358.00 | 1701.00 | 94.60 | 59.70 | 40.80 | 29.40 | 22.40 |
| Thiophene Sulfoxide | 2.83 | 1.35 | 0.86 | 0.68 | 0.61 | 0.59 | 0.61 | 0.66 | 0.76 | 0.90 | 1.25 |
| Thiophene Sulfone | 49.40 | 16.90 | 7.46 | 4.10 | 2.61 | 1.84 | 1.40 | 1.13 | 0.95 | 0.84 | 0.77 |
| Thiophene | 2208.00 | 217.00 | 49.40 | 18.34 | 9.12 | 5.37 | 3.53 | 2.53 | 1.93 | 1.54 | 1.27 |
| Naphthalene | 4.44E+04 | 2392.00 | 361.00 | 100.00 | 40.00 | 20.10 | 11.70 | 7.54 | 5.31 | 3.94 | 3.06 |
| Toluene | 9799.00 | 973.00 | 215.00 | 76.70 | 36.20 | 20.70 | 13.30 | 9.39 | 6.96 | 5.47 | 4.44 |
| nC$_{12}$ | 3.52E+08 | 8.71E+06 | 7.29E+05 | 1.33E+05 | 3.93E+04 | 1.58E+04 | 7708.00 | 4359.00 | 2724.00 | 1845.00 | 1313.00 |

TABLE 4B

| Compound | | Solvent (Acetonitrile W %/Water W %) | | | | | |
|---|---|---|---|---|---|---|---|
| Common Name | IUPAC | 0/100 | 10/90 | 20/80 | 30/70 | 40/60 | 50/50 |
| | | Activity Coefficient | | | | | |
| 6-Methylbenzothiophene oxide | 6-methyl-1-benzo(b)thiophene 1-oxide | 47.00 | 8.53* | 2.95* | 1.55* | 1.04* | 0.82 |
| 6-Methylbenzothiophene sulfone | 6-methyl-1-benzo(b)thiophene 1,1-dioxide | 988.00 | 144.56# | 36.35# | 13.57 C | 6.55 C | 3.75 |
| 6-Methylbenzothiophene | 6-methyl-1-benzo(b)thiophene | 1.20E+05 | 4071.70# | 471.23# | 111.26# | 39.85# | 18.52 |
| 2,6-Dimethylbenzothiophene oxide | 2,6-dimethyl-1-benzo(b)thiophene 1-oxide | 88.00 | 13.06* | 3.96* | 1.91* | 1.22* | 0.93* |
| 2,6-Dimethylbenzothiophene sulfone | 2,6-dimethyl-1-benzo(b)thiophene 1,1-dioxide | 1967.00 | 248.62# | 56.58# | 19.79# | 9.13 C | 5.06 C |
| 2,6-Dimethylbenzothiophene | 2,6-dimethyl-1-benzo(b)thiophene | 3.87E+05 | 10273.20# | 1008.46# | 213.25# | 70.66# | 31.00# |
| 2,3,6-Trimethylbenzothiophene-oxide | 2,3,6-trimethyl-1-benzo(b)thiophene 1-oxide | 313.00 | 35.58 | 9.09* | 3.90* | 2.28* | 1.63* |
| 2,3,6-Trimethylbenzothiophene sulfone | 2,3,6-trimethyl-1-benzo(b)thiophene 1,1-dioxide | 5917.00 | 591.69 | 115.79# | 36.68# | 15.79 C | 8.32 C |
| 2,3,6-Trimethylbenzothiophene | 2,3,6-trimethyl-1-benzo(b)thiophene | 1.17E+06 | 2.51E+04 | 2141.44# | 412.38# | 127.96# | 53.49# |
| Dibenzothiophene oxide | dibenzothiophene 5-oxide | 251.00 | 25.17 | 6.16* | 2.60* | 1.51* | 1.07* |
| Dibenzothiophene sulfone | dibenzothiophene 5,5-dioxide | 6267.00 | 472.09 | 80.07# | 23.20# | 9.39 C | 4.73 C |
| Dibenzothiophene | dibenzothiophene | 6.67E+05 | 1.20E+04 | 959.31# | 178.53# | 54.28# | 22.40# |
| 4-Methyldibenzothiophene oxide | 4-methyldibenzothiophene 5-oxide | 718.00 | 56.44 | 11.74* | 4.43* | 2.37* | 1.57* |
| 4-Methyldibenzothiophene sulfone | 4-methyldibenzothiophene 5,5-dioxide | 1.79E+04 | 1060.44 | 155.12# | 40.89# | 15.51 C | 7.46 C |
| 4-Methyldibenzothiophene | 4-methyldibenzothiophene | 1.84E+06 | 2.72E+04 | 1896.52 | 322.84# | 92.18# | 36.31# |
| 3,6-Dimethyldibenzothiophene oxide | 3,6-dimethyldibenzothiophene 5-oxide | 1664.00 | 96.24 | 17.31 | 5.96* | 3.00* | 1.93* |
| 3,6-Dimethyldibenzothiophene sulfone | 3,6-dimethyldibenzothiophene 5,5-dioxide | 4.41E+04 | 1977.55 | 259.57 | 63.67# | 22.97# | 10.64 C |
| 3,6-Dimethyldibenzothiophene | 3,6-dimethyldibenzothiophene | 5.81E+06 | 6.88E+04 | 4062.65 | 618.10# | 163.05# | 60.56# |
| 4,6-Dimethyldibenzothiophene oxide | 4,6-dimethyldibenzothiophene 5-oxide | 2468.00 | 104.82 | 18.87 | 6.48* | 3.26* | 2.08* |
| 4,6- | 4,6- | 3.74E+04 | 2182.14 | 281.61 | 68.24# | 24.40# | 11.23 C |

TABLE 4B-continued

| Common Name | IUPAC | | | | | | |
|---|---|---|---|---|---|---|---|
| Dimethyldibenzothiophene sulfone | dimethyldibenzothiophene 5,5-dioxide | | | | | | |
| 4,6-Dimethyldibenzothiophene | 4,6-dimethyldibenzothiophene | 5.04E+06 | 6.75E+04 | 4015.90 | 613.49# | 162.24# | 60.36# |
| 2,4-Dimethyldibenzothiophene oxide | 2,4-dimethyldibenzothiophene 5-oxide | 1542.00 | 148.80 | 26.01 | 8.69* | 4.24* | 2.63* |
| 2,4-Dimethyldibenzothiophene sulfone | 2,4-dimethyldibenzothiophene 5,5-dioxide | 3.90E+04 | 1968.12 | 267.19 | 67.31# | 24.80# | 11.69 C |
| 2,4-Dimethyldibenzothiophene | 2,4-dimethyldibenzothiophene | 6.02E+06 | 6.13E+04 | 3762.60 | 587.60# | 157.89# | 59.46# |
| 2,4,7-Trimethyldibenzothiophene oxide | 2,4,7-trimethyldibenzothiophene 5-oxide | 4095.00 | 204.56 | 31.72 | 9.90* | 4.66* | 2.84* |
| 2,4,7-Trimethyldibenzothiophene sulfone | 2,4,7-trimethyldibenzothiophene 5,5-dioxide | 9.72E+04 | 4114.13 | 477.44 | 107.82# | 36.70# | 16.29 C |
| 2,4,7-Trimethyldibenzothiophene | 2,4,7-trimethyldibenzothiophene | 2.05E+07 | 1.82E+05 | 9081.97 | 1236.03# | 301.37# | 105.61# |
| 4-Ethyldibenzothiophene oxide | 4-ethyldibenzothiophene 5-oxide | 1706.00 | 106.31 | 19.14 | 6.59* | 3.31* | 2.11* |
| 4-Ethyldibenzothiophene sulfone | 4-ethyldibenzothiophene 5,5-dioxide | 5.43E+04 | 2379.14 | 288.13 | 67.17# | 23.41# | 10.58 C |
| 4-Ethyldibenzothiophene | 4-ethyldibenzothiophene | 5.28E+06 | 6.19E+04 | 3733.25 | 577.43# | 154.25# | 57.86# |
| 4-Propyldibenzothiophene oxide | 4-propyldibenzothiophene 5-oxide | 4103.00 | 197.90 | 30.36 | 9.43* | 4.42* | 2.69* |
| 4-Propyldibenzothiophene sulfone | 4-propyldibenzothiophene 5,5-dioxide | 1.60E+05 | 5353.77 | 543.31 | 112.57# | 36.10# | 15.34 C |
| 4-Propyldibenzothiophene | 4-propyldibenzothiophene | 1.72E+07 | 1.52E+05 | 7603.31 | 1040.43# | 254.96# | 89.74# |
| 2-Butyldibenzothiophene oxide | 2-butyldibenzothiophene 5-oxide | 1.43E+04 | 491.67 | 60.43 | 16.23* | 6.90* | 3.91 |
| 2-Butyldibenzothiophene sulfone | 2-butyldibenzothiophene 5,5-dioxide | 3.38E+05 | 9483.96 | 845.18 | 159.73# | 47.89# | 19.34 |
| 2-Butyldibenzothiophene | 2-butyldibenzothiophene | 7.58E+07 | 4.62E+05 | 1.82E+04 | 2114.09# | 461.46# | 149.06 |
| 2-Pentyldibenzothiophene oxide | 2-pentyldibenzothiophene 5-oxide | 5.25E+04 | 1353.65 | 137.54 | 32.46 | 12.56* | 6.62* |
| 2-Pentyldibenzothiophene sulfone | 2-pentyldibenzothiophene 5,5-dioxide | 1.07E+06 | 2.27E+04 | 1683.13 | 281.50 | 77.44# | 29.35# |
| 2-Pentyldibenzothiophene | 2-pentyldibenzothiophene | 2.67E+08 | 1.22E+06 | 3.99E+04 | 4096.46 | 819.52# | 248.23# |
| 1-Phenyldibenzothiophene oxide | 1-phenyldibenzothiophene 5-oxide | 1.17E+04 | 346.79 | 40.02 | 10.38* | 4.31* | 2.40* |
| 1-Phenyldibenzothiophene sulfone | 1-phenyldibenzothiophene 5,5-dioxide | 3.46E+05 | 7700.99 | 613.74 | 108.62# | 31.20# | 12.23 C |
| 1-Phenyldibenzothiophene | 1-phenyldibenzothiophene | 4.77E+07 | 2.47E+05 | 9114.87 | 1026.24# | 219.98# | 70.27 |
| 4-Phenyldibenzothiophene oxide | 4-phenyldibenzothiophene 5-oxide | 6.25E+04 | 1308.50 | 119.33 | 25.85 | 9.26* | 4.54* |
| 4-Phenyldibenzothiophene sulfone | 4-phenyldibenzothiophene 5,5-dioxide | 3.59E+05 | 7511.03 | 578.80 | 100.47 | 28.52# | 11.09 C |
| 4-Phenyldibenzothiophene | 4-phenyldibenzothiophene | 5.26E+07 | 2.51E+05 | 8771.03 | 949.21 | 197.54 | 61.68 |
| Dodecane | Dodecane | 6.02E+08 | 8.57E+06 | 5.46E+05 | 8.65E+04 | 2.34E+04 | 8817.80 |
| Naphthalene | bicyclo[4.4.0]deca-1,3,5,7,9-pentene | 5.55E+04 | 2395.70 | 324.00 | 84.70 | 32.60 | 15.90 |
| Dibutyl sulfoxide | 1-butylsulfinyl-butane | 49.90 | 8.50* | 2.80* | 1.50* | 1.00* | 0.80* |
| Dibutyl sulfone | 1-butylsulfonyl-butane | 324.80 | 81.70# | 28.50# | 13.50 C | 7.90 C | 5.30 C |
| Dibutyl sulfide | 1-butylsulfanyl-butane | 5.23E+05 | 2.50E+04# | 3243.50# | 804.00# | 294.70# | 138.60# |
| Thiophene sulfide | tetrahydrothiophene 1-oxide | 2.00 | 1.10* | 0.70* | 0.60 | 0.50 | 0.50 |
| Thiophene sulfone | tetrahydrothiophene 1,1-dioxide | 43.10 | 16.00# | 7.30 C | 4.00 | 2.60 | 1.80 |
| Thiophene | Thiophene | 1819.20 | 187.00# | 43.60# | 16.40 | 8.10 | 4.80 |
| Toluene | Methylbenzene | 1.26E+04 | 1029.20 | 204.20 | 68.60 | 31.40 | 17.50 |

| | | Solvent (Acetonitrile W %/Water W %) | | | | |
|---|---|---|---|---|---|---|
| | | 60/40 | 70/30 | 80/20 | 90/10 | 100/0 |
| Compound Common Name | IUPAC | Activity Coefficient | | | | |
| 6-Methylbenzothiophene oxide | 6-methyl-1-benzo(b)thiophene 1-oxide | 0.72 | 0.69 | 0.71 | 0.80 | 1.06 |
| 6-Methylbenzothiophene sulfone | 6-methyl-1-benzo(b)thiophene 1,1-dioxide | 2.42 | 1.70 | 1.28 | 1.01 | 0.84 |
| 6-Methylbenzothiophene | 6-methyl-1-benzo(b)thiophene | 10.22 | 6.36 | 4.31 | 3.11 | 2.36 |
| 2,6-Dimethylbenzothiophene oxide | 2,6-dimethyl-1-benzo(b)thiophene 1-oxide | 0.80 | 0.76 | 0.79 | 0.90 | 1.26 |

TABLE 4B-continued

| | | | | | | |
|---|---|---|---|---|---|---|
| 2,6-Dimethylbenzothiophene sulfone | 2,6-dimethyl-1-benzo(b)thiophene 1,1-dioxide | 3.18 | 2.20 | 1.62 | 1.27 | 1.05 |
| 2,6-Dimethylbenzothiophene | 2,6-dimethyl-1-benzo(b)thiophene | 16.37 | 9.84 | 6.48 | 4.57 | 3.39 |
| 2,3,6-Trimethylbenzothiophene-oxide | 2,3,6-trimethyl-1-benzo(b)thiophene 1-oxide | 1.33* | 1.20 | 1.19 | 1.31 | 1.76 |
| 2,3,6-Trimethylbenzothiophene sulfone | 2,3,6-trimethyl-1-benzo(b)thiophene 1,1-dioxide | 5.04 $^C$ | 3.37 | 2.43 | 1.86 | 1.50 |
| 2,3,6-Trimethylbenzothiophene | 2,3,6-trimethyl-1-benzo(b)thiophene | 27.23# | 15.89 | 10.23 | 7.07 | 5.16 |
| Dibenzothiophene oxide | dibenzothiophene 5-oxide | 0.87 | 0.79 | 0.77 | 0.84 | 1.08 |
| Dibenzothiophene sulfone | dibenzothiophene 5,5-dioxide | 2.77 | 1.81 | 1.28 | 0.96 | 0.77 |
| Dibenzothiophene | dibenzothiophene | 11.30 | 6.55 | 4.20 | 2.90 | 2.11 |
| 4-Methyldibenzothiophene oxide | 4-methyldibenzothiophene 5-oxide | 1.22* | 1.05 | 1.00 | 1.05 | 1.32 |
| 4-Methyldibenzothiophene sulfone | 4-methyldibenzothiophene 5,5-dioxide | 4.21 $^C$ | 2.67 | 1.84 | 1.36 | 1.07 |
| 4-Methyldibenzothiophene | 4-methyldibenzothiophene | 17.68# | 9.97 | 6.24 | 4.23 | 3.03 |
| 3,6-Dimethyldibenzothiophene oxide | 3,6-dimethyldibenzothiophene 5-oxide | 1.45* | 1.24 | 1.17 | 1.25 | 1.64 |
| 3,6-Dimethyldibenzothiophene sulfone | 3,6-dimethyldibenzothiophene 5,5-dioxide | 5.85 $^C$ | 3.63 | 2.46 | 1.79 | 1.38 |
| 3,6-Dimethyldibenzothiophene | 3,6-dimethyldibenzothiophene | 28.20# | 15.34 | 9.33 | 6.17 | 4.33 |
| 4,6-Dimethyldibenzothiophene oxide | 4,6-dimethyldibenzothiophene 5-oxide | 1.56* | 1.32 | 1.23 | 1.29 | 1.66 |
| 4,6-Dimethyldibenzothiophene sulfone | 4,6-dimethyldibenzothiophene 5,5-dioxide | 6.13 $^C$ | 3.79 | 2.56 | 1.85 | 1.43 |
| 4,6-Dimethyldibenzothiophene | 4,6-dimethyldibenzothiophene | 28.13# | 15.32 | 9.33 | 6.17 | 4.33 |
| 2,4-Dimethyldibenzothiophene oxide | 2,4-dimethyldibenzothiophene 5-oxide | 1.92* | 1.58 | 1.43 | 1.45 | 1.77 |
| 2,4-Dimethyldibenzothiophene sulfone | 2,4-dimethyldibenzothiophene 5,5-dioxide | 6.51 $^C$ | 4.08 | 2.79 | 2.05 | 1.59 |
| 2,4-Dimethyldibenzothiophene | 2,4-dimethyldibenzothiophene | 27.98# | 15.35 | 9.40 | 6.25 | 4.41 |
| 2,4,7-Trimethyldibenzothiophene oxide | 2,4,7-trimethyldibenzothiophene 5-oxide | 2.07* | 1.72* | 1.59 | 1.66 | 2.17 |
| 2,4,7-Trimethyldibenzothiophene sulfone | 2,4,7-trimethyldibenzothiophene 5,5-dioxide | 8.66 $^C$ | 5.23 $^C$ | 3.47 | 2.48 | 1.89 |
| 2,4,7-Trimethyldibenzothiophene | 2,4,7-trimethyldibenzothiophene | 47.01# | 24.69# | 14.59 | 9.41 | 6.47 |
| 4-Ethyldibenzothiophene oxide | 4-ethyldibenzothiophene 5-oxide | 1.58* | 1.33 | 1.24 | 1.28 | 1.60 |
| 4-Ethyldibenzothiophene sulfone | 4-ethyldibenzothiophene 5,5-dioxide | 5.70 $^C$ | 3.48 | 2.33 | 1.68 | 1.29 |
| 4-Ethyldibenzothiophene | 4-ethyldibenzothiophene | 27.15# | 14.87 | 9.10 | 6.04 | 4.26 |
| 4-Propyldibenzothiophene oxide | 4-propyldibenzothiophene 5-oxide | 1.95* | 1.61* | 1.48 | 1.52 | 1.93 |
| 4-Propyldibenzothiophene sulfone | 4-propyldibenzothiophene 5,5-dioxide | 7.89 $^C$ | 4.64 $^C$ | 3.02 | 2.12 | 1.59 |
| 4-Propyldibenzothiophene | 4-propyldibenzothiophene | 40.11# | 21.14# | 12.53 | 8.11 | 5.59 |
| 2-Butyldibenzothiophene oxide | 2-butyldibenzothiophene 5-oxide | 2.70* | 2.15* | 1.92* | 1.95 | 2.45 |
| 2-Butyldibenzothiophene sulfone | 2-butyldibenzothiophene 5,5-dioxide | 9.56 $^C$ | 5.45 $^C$ | 3.46 $^C$ | 2.38 | 1.76 |
| 2-Butyldibenzothiophene | 2-butyldibenzothiophene | 62.35# | 31.19# | 17.72# | 11.06 | 7.40 |
| 2-Pentyldibenzothiophene oxide | 2-pentyldibenzothiophene 5-oxide | 4.31* | 3.26* | 2.80* | 2.71 | 3.23 |
| 2-Pentyldibenzothiophene sulfone | 2-pentyldibenzothiophene 5,5-dioxide | 13.82 $^C$ | 7.59 $^C$ | 4.67 $^C$ | 3.13 | 2.27 |
| 2-Pentyldibenzothiophene | 2-pentyldibenzothiophene | 98.85# | 47.55# | 26.18# | 15.92 | 10.42 |
| 1-Phenyldibenzothiophene oxide | 1-phenyldibenzothiophene 5-oxide | 1.63* | 1.28 | 1.13 | 1.13 | 1.39 |
| 1-Phenyldibenzothiophene sulfone | 1-phenyldibenzothiophene 5,5-dioxide | 5.91 $^C$ | 3.32 | 2.07 | 1.41 | 1.03 |
| 1-Phenyldibenzothiophene | 1-phenyldibenzothiophene | 29.19 | 14.53 | 8.23 | 5.13 | 3.44 |

TABLE 4B-continued

| | | | | | | |
|---|---|---|---|---|---|---|
| 4-Phenyldibenzothiophene oxide | 4-phenyldibenzothiophene 5-oxide | 2.74* | 1.93 | 1.53 | 1.36 | 1.42 |
| 4-Phenyldibenzothiophene sulfone | 4-phenyldibenzothiophene 5,5-dioxide | 5.33 $^C$ | 2.98 | 1.86 | 1.26 | 0.92 |
| 4-Phenyldibenzothiophene | 4-phenyldibenzothiophene | 25.16 | 12.34 | 6.91 | 4.26 | 2.83 |
| Dodecane | Dodecane | 4151.50 | 2277.40 | 1393.70 | 923.70 | 647.10 |
| Naphthalene | bicyclo[4.4.0]deca-1,3,5,7,9-pentene | 9.20 | 5.90 | 4.10 | 3.00 | 2.30 |
| Dibutyl sulfoxide | 1-butylsulfinyl-butane | 0.80* | 0.80* | 1.00* | 1.40* | 2.80* |
| Dibutyl sulfone | 1-butylsulfonyl-butane | 3.90 $^C$ | 3.10 $^C$ | 2.50 $^C$ | 2.20 $^C$ | 2.10 $^C$ |
| Dibutyl sulfide | 1-butylsulfanyl-butane | 77.00[#] | 48.10[#] | 32.70[#] | 23.70[#] | 18.00[#] |
| Thiophene sulfide | tetrahydrothiophene 1-oxide | 0.50 | 0.60 | 0.70 | 0.80 | 1.10 |
| Thiophene sulfone | tetrahydrothiophene 1,1-dioxide | 1.40 | 1.10 | 0.90 | 0.80 | 0.70 |
| Thiophene | Thiophene | 3.20 | 2.30 | 1.70 | 1.40 | 1.10 |
| Toluene | Methylbenzene | 11.00 | 7.70 | 5.70 | 4.40 | 3.50 |

Acetic Acid Formulations

In a further embodiment of the present invention, the solvent formulation comprises an aqueous solution of acetic acid. An aqueous solution of acetic acid having a concentration of about 2.5 W % to about 60 W % is particularly useful as a selective solvent formulation for extraction of sulfoxide products, and an aqueous solution of acetic acid having a concentration of about 30 W % to about 70 W % is particularly useful for extraction of a sulfoxidation products, i.e., sulfoxides and sulfones. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. For non-bulky sulfoxide products, the concentration of the aqueous acetic acid solution can be about 2.5 W % to about 20 W %, which will extract the non-bulky sulfoxide products, while minimizing co-extraction of certain sulfones, untreated organosulfur compounds, non-heteroatom aromatics and other hydrocarbons. For bulky sulfoxide products and/or bulky sulfoxidation products, the concentration of the aqueous acetic acid solution can be about 30 W % to about 70 W %, which will extract the bulky sulfoxide and/or sulfoxidation products, while minimizing co-extraction of non-heteroatom aromatics, untreated organosulfur compounds and other hydrocarbons.

In an extractive simulation. COSMO-RS software was used to simulate γ for selective extraction of oxidized model A fuel by solvent formulations of aqueous acetic acid. Acetic acid is desirable as a polar organic solvent due to its relatively low boiling point, thereby facilitating recovery and separation from the sulfoxide products or the sulfoxidation products.

Figure 12:
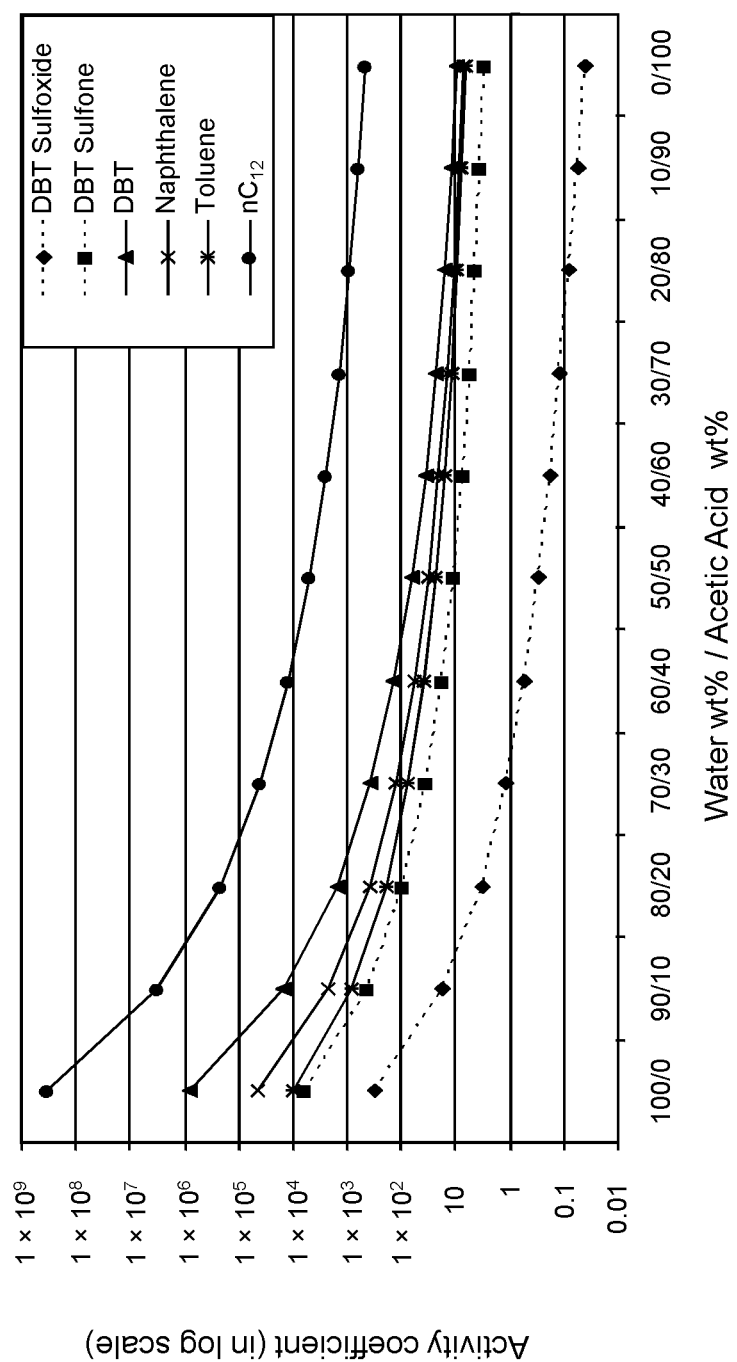
FIGS. 12, 13 and 14 are plots of computational models of the activity coefficient values for a range of concentrations of an acetic acid solvent formulation for sulfoxidation products of DBT, thiophene and dibutyl sulfide compounds, respectively, relative to other components in a hydrocarbon mixture.
Figure 13:
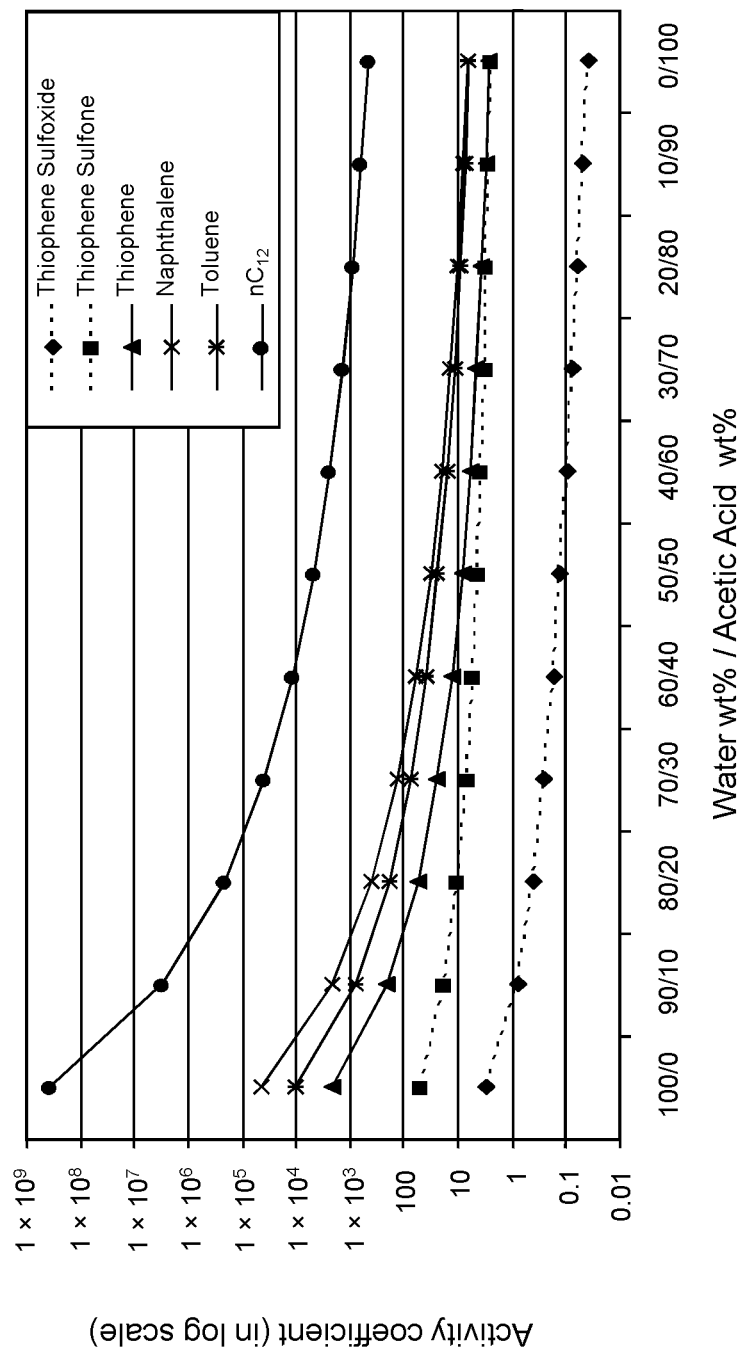
Figure 14:
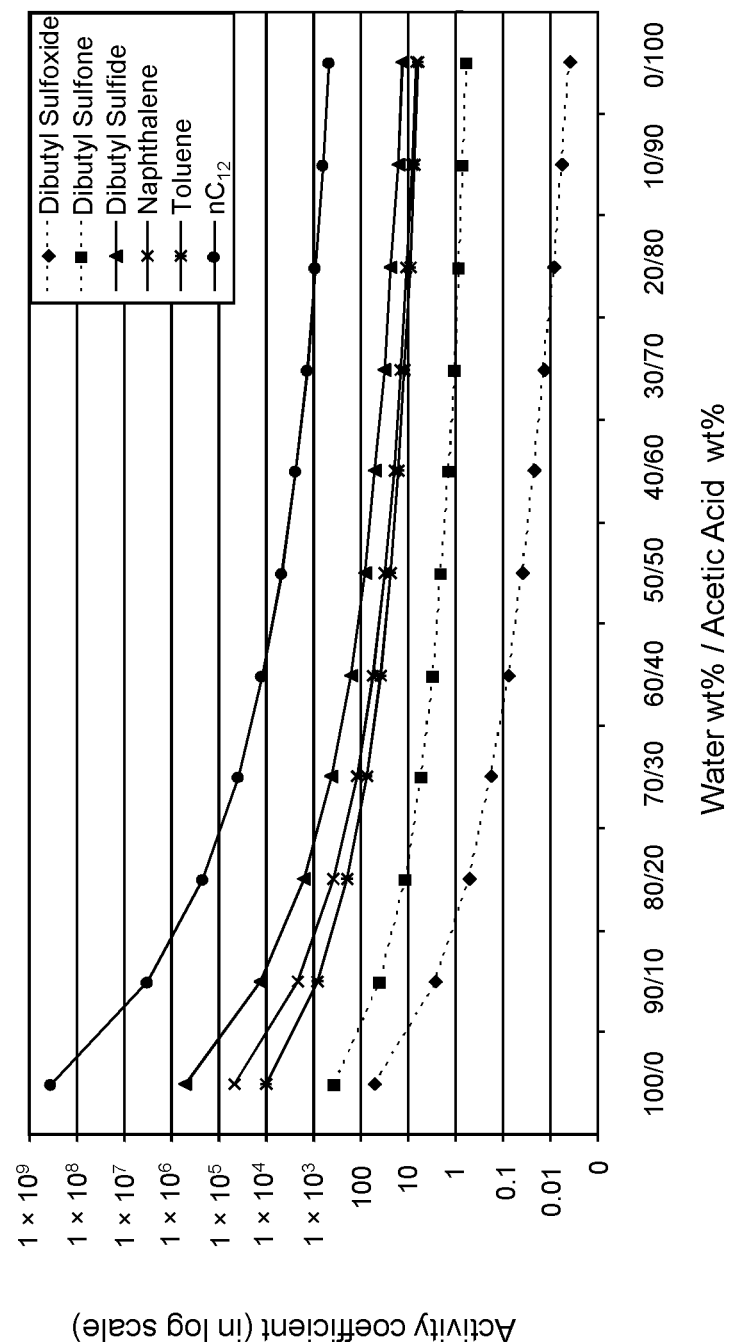

Table 5A illustrates the activity coefficient of different concentrations of aqueous acetic acid. Based on the activity coefficient values in Table 5A, a useful aqueous acetic acid selective solvent formulation has a concentration of about 20 W % to about 40 W % for extraction of DBT sulfoxide, with minimal co-extraction of certain sulfones, untreated organosulfur compounds, aromatics and other hydrocarbons, as shown in FIG. 12. It is also apparent from FIG. 12 and the data in Table 5A that a useful concentration of acetic acid is about 40 W % to about 60 W % for extraction of DBT sulfoxide combined with DBT sulfone, with minimal co-extraction of aromatics, certain untreated organosulfur compounds and other hydrocarbons. A concentration of acetic acid of about 40 W % to about 50 W % is also suitable for extraction of thiophene sulfoxide, thiophene sulfone, dibutyl sulfoxide and dibutyl sulfone. If the target sulfoxidation products are primarily thiophene sulfoxide and dibutyl sulfoxide, a useful selective solvent formulation will have about 5 W % to about 20 W % aqueous acetic acid, as shown in FIGS. 13 and 14. These extractions occur selectively with minimum co-extraction of other hydrocarbon constituents such as dodecane ($nC_{12}$), toluene, naphthalene, thiophene, dibenzothiophene and dibutyl sulfides.

In another extraction simulation. COSMO-RS software was used to simulate γ for formulations of aqueous acetic acid as extraction solvents for oxidized model B fuel. Activity coefficient values as shown in Table 5B indicate that certain formulations of aqueous acetic acid will selectively extract bulky sulfoxide products while minimizing co-extraction of their corresponding sulfones and underlying organosulfur compounds. In addition, activity coefficient values as shown in Table 5B indicate that certain formulations of aqueous acetonitrile will selectively extract bulky sulfoxidation products, including sulfoxides and sulfones, with minimal co-extraction of aromatics, untreated organosulfur compounds and other hydrocarbons. Based on the activity coefficient values in Table 5B, a useful acetic acid selective solvent formulation has a concentration of about 20 W % to about 70 W % for selective extraction of bulky sulfoxidation products including alkyl and dialkyl derivatives of benzothiophenes and dibenzothiophenes. In addition, aqueous acetic acid selective solvent formulations of about 10 W % to about 50 W % are also useful for extraction of bulky sulfoxide products including with minimal co-extraction of certain sulfones, aromatics, untreated organosulfur compounds and other hydrocarbons.

Figure 15:
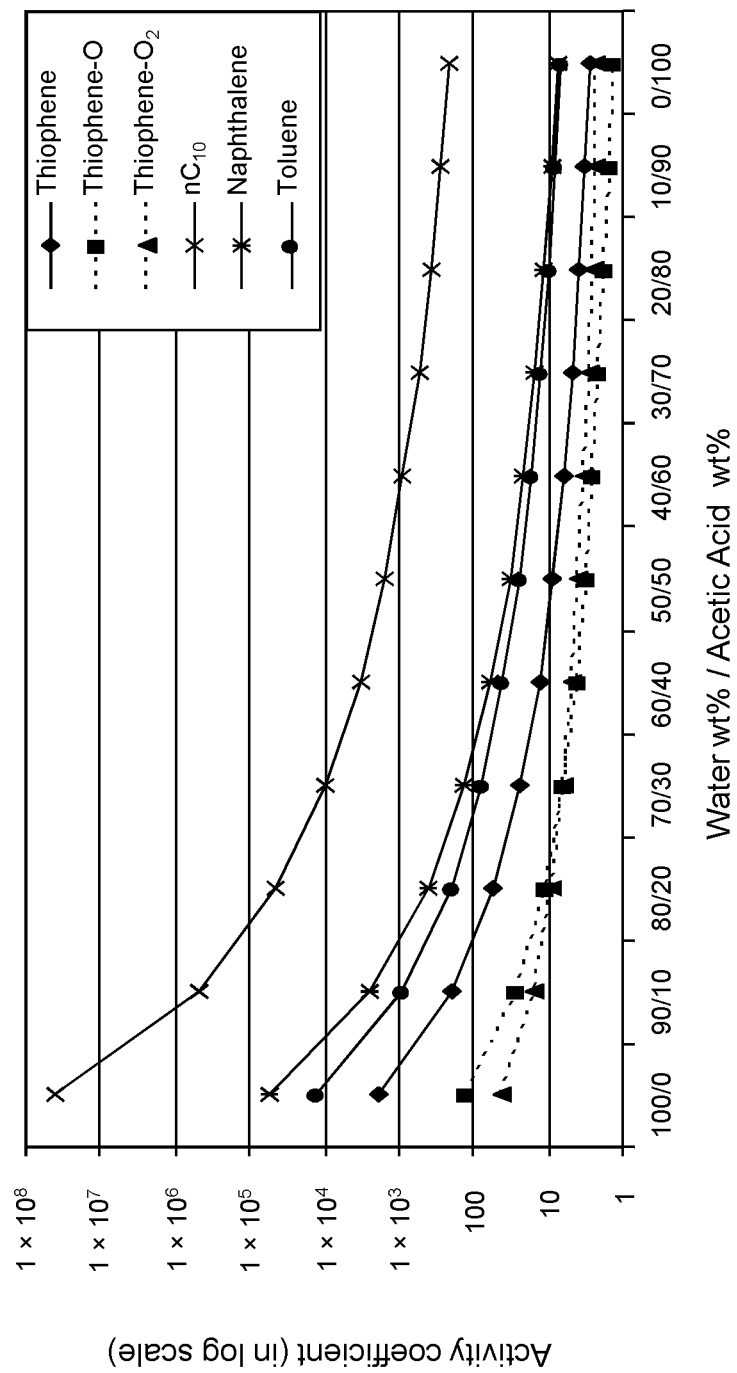
FIGS. 15, 16 and 17 are plots of computational models of the activity coefficient values for a range of concentrations of an acetic acid solvent formulation for sulfoxidation products of thiophene, methylthiophene, and dimethylthiophene, respectively, relative to other components in a hydrocarbon mixture.
Figure 16:
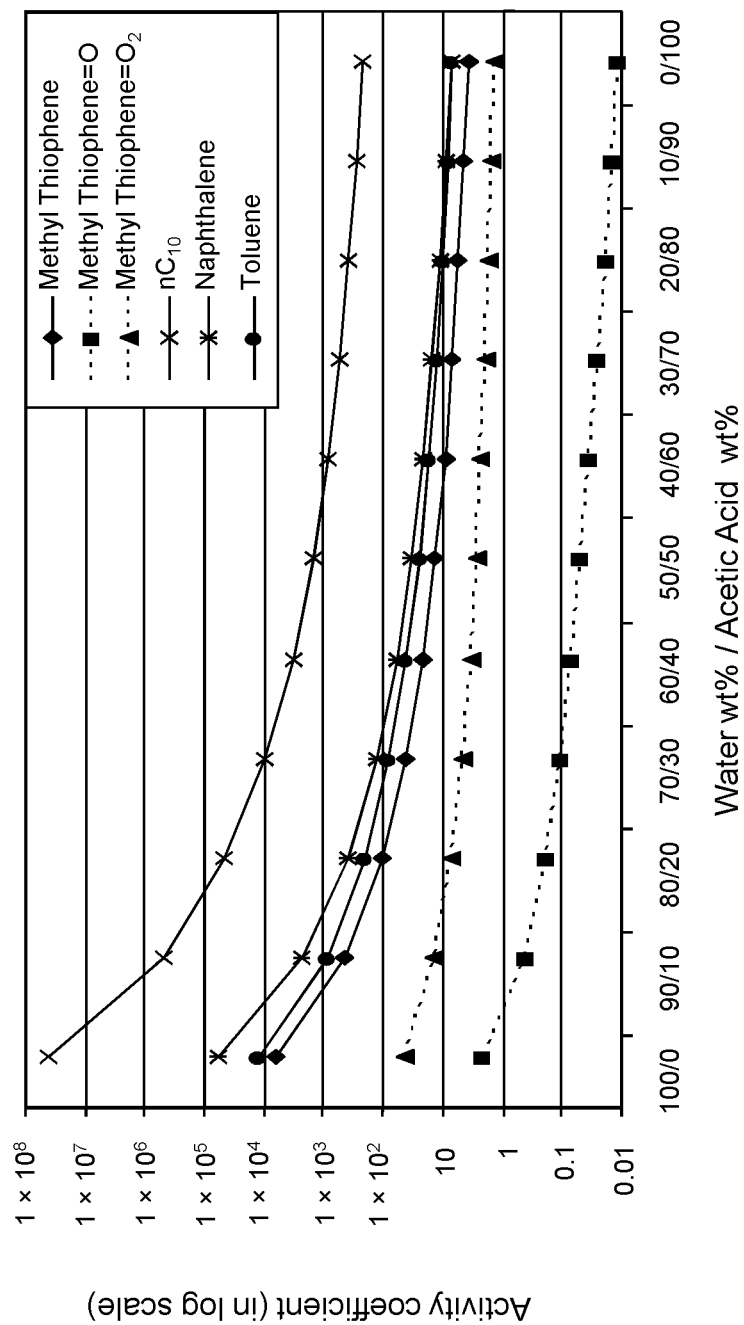
Figure 17:
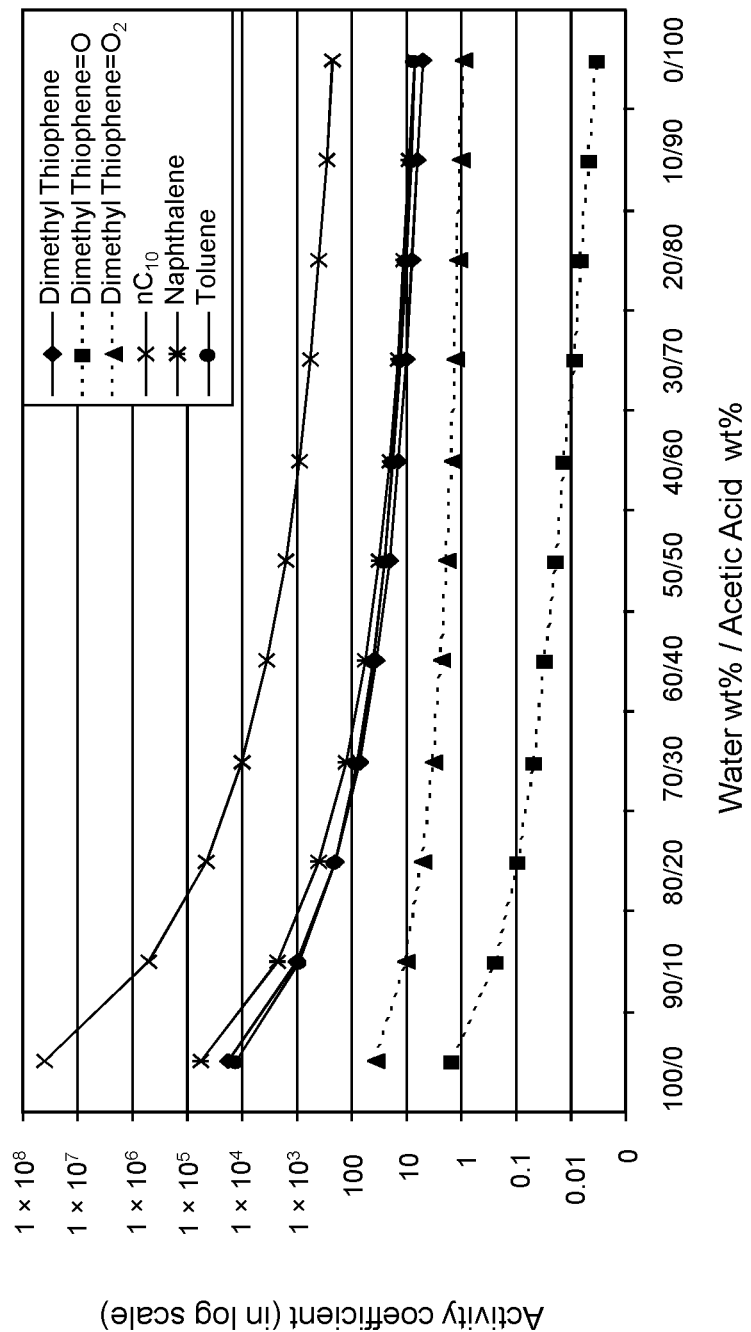

Furthermore, Table 5B and FIGS. 15-17 show the efficacy of the selective solvent formulation, particularly in the range of about 30 W % to about 70 W % aqueous acetic acid, for selective extraction of bulky sulfoxidation products including sulfoxides and sulfones of thiophenes and various alkylated thiophenes.

In Table 5B, activity coefficients for targeted sulfoxides for which extraction is favored are marked with an asterisk ("*"), activity coefficients for non-targeted underlying organosulfur compounds and in certain cases corresponding sulfones for which co-extraction is minimized are marked with a pound symbol ("#"). Furthermore, activity coefficients for targeted sulfones for which extraction is favored (i.e., in combination with corresponding sulfoxides) are marked with a letter "C".

It is noted that although the activity coefficient values for certain high concentration acetic acid formulations indicate favorable extraction of certain bulky or non-bulky sulfoxidation products (including sulfoxides and sulfones), these high concentration acetic acid formulations greater than 70 W %) also extract untargeted species and therefore are not particularly desirable for extraction of a broad array of organosulfur oxidation products.

TABLE 5A

| Compound | Solvent (Acetic Acid W %/Water W %) | | | | | | | | | | |
|---|---|---|---|---|---|---|---|---|---|---|---|
| | 0/100 | 10/90 | 20/80 | 30/70 | 40/60 | 50/50 | 60/40 | 70/30 | 80/20 | 90/10 | 100/0 |
| | Activity Coefficient | | | | | | | | | | |
| dibenzothiophene 5-oxide (DBT sulfoxide) | 321.00 | 16.40 | 3.25 | 1.15 | 0.54 | 0.30 | 0.18 | 0.12 | 0.08 | 0.06 | 0.04 |
| dibenzothiophene 5,5-dioxide (DBT sulfone) | 6063.00 | 416.00 | 92.80 | 35.20 | 17.60 | 10.70 | 7.24 | 5.37 | 4.18 | 3.39 | 2.86 |
| dibenzothiophene (DBT) | 7.90E+05 | 1.45E+04 | 1541.00 | 365.00 | 133.00 | 63.40 | 35.90 | 22.90 | 16.00 | 11.80 | 9.21 |
| 1-butylsulfinyl-butane (Dibutyl Sulfoxide) | 51.40 | 2.69 | 0.52 | 0.17 | 0.08 | 0.04 | 0.02 | 0.01 | 0.01 | 0.01 | 0.00 |
| 1-butylsulfonyl-butane (Dibutyl Sulfone) | 337.00 | 37.30 | 11.00 | 5.05 | 2.89 | 1.90 | 1.35 | 1.02 | 0.80 | 0.65 | 0.54 |
| 1-butylsulfanyl-butane (Dibutyl Sulfide) | 5.04E+05 | 1.31E+04 | 1652.00 | 433.00 | 169.00 | 83.90 | 48.90 | 31.80 | 22.60 | 16.90 | 13.20 |
| Thiophene Sulfoxide | 2.83 | 0.77 | 0.38 | 0.24 | 0.17 | 0.13 | 0.10 | 0.08 | 0.06 | 0.05 | 0.04 |
| Thiophene Sulfone | 49.40 | 18.20 | 10.20 | 6.82 | 5.16 | 4.18 | 3.56 | 3.13 | 2.80 | 2.56 | 2.36 |
| Thiophene | 2208.00 | 213.00 | 56.80 | 24.00 | 13.20 | 8.41 | 5.99 | 4.53 | 3.60 | 3.00 | 2.56 |
| Naphthalene | 4.44E+04 | 2186.00 | 392.00 | 126.00 | 57.40 | 31.80 | 20.30 | 14.10 | 10.60 | 8.33 | 6.82 |
| Toluene | 9799.00 | 812.00 | 192.00 | 75.20 | 38.90 | 23.60 | 16.10 | 11.90 | 9.30 | 7.61 | 6.42 |
| $nC_{12}$ | 3.52E+08 | 3.14E+06 | 2.18E+05 | 3.89E+04 | 1.16E+04 | 4770.00 | 2392.00 | 1394.00 | 898.00 | 626.00 | 464.00 |

TABLE 5B

| Compound | | Solvent (Acetic Acid W %/Water W %) | | | | | |
|---|---|---|---|---|---|---|---|
| Common Name | IUPAC | 0/100 | 10/90 | 20/80 | 30/70 | 40/60 | 50/50 |
| | | Activity Coefficient | | | | | |
| 6-Methylbenzothiophene oxide | 6-methyl-1-benzo(b)thiophene 1-oxide | 47.00 | 3.88* | 1.02* | 0.43* | 0.23* | 0.14* |
| 6-Methylbenzothiophene sulfone | 6-methyl-1-benzo(b)thiophene 1,1-dioxide | 988.00 | 111.41# | 33.42# | 15.36 C | 8.92 C | 5.98 C |
| 6-Methylbenzothiophene | 6-methyl-1-benzo(b)thiophene | 1.20E+05 | 3753.75# | 545.27# | 159.53# | 67.98# | 36.43# |
| 2,6-Dimethylbenzothiophene oxide | 2,6-dimethyl-1-benzo(b)thiophene 1-oxide | 88.00 | 5.22* | 1.15* | 0.43* | 0.21* | 0.12* |
| 2,6-Dimethylbenzothiophene sulfone | 2,6-dimethyl-1-benzo(b)thiophene 1,1-dioxide | 1967.00 | 165.47# | 42.91# | 18.08# | 9.91 C | 6.37 C |
| 2,6-Dimethylbenzothiophene | 2,6-dimethyl-1-benzo(b)thiophene | 3.87E+05 | 8718.11# | 1060.17# | 277.85# | 109.85# | 55.80# |
| 2,3,6-Trimethylbenzothiophene-oxide | 2,3,6-trimethyl-1-benzo(b)thiophene 1-oxide | 313.00 | 13.49* | 2.52* | 0.86* | 0.39* | 0.21* |
| 2,3,6-Trimethylbenzothiophene sulfone | 2,3,6-trimethyl-1-benzo(b)thiophene 1,1-dioxide | 5917.00 | 362.34# | 79.34# | 30.11# | 15.37 C | 9.38 C |
| 2,3,6-Trimethylbenzothiophene | 2,3,6-trimethyl-1-benzo(b)thiophene | 1.17E+06 | 1.98E+04# | 2068.98# | 493.69# | 183.21# | 88.94# |
| Dibenzothiophene oxide | dibenzothiophene 5-oxide | 251.00 | 12.00* | 2.37* | 0.83* | 0.39* | 0.22* |
| Dibenzothiophene sulfone | dibenzothiophene 5,5-dioxide | 6267.00 | 390.07# | 85.32# | 32.30# | 16.46# | 10.05 C |
| Dibenzothiophene | dibenzothiophene | 6.67E+05 | 1.20E+04# | 1294.98# | 315.39# | 118.72# | 58.27# |
| 4-Methyldibenzothiophene oxide | 4-methyldibenzothiophene 5-oxide | 718.00 | 25.56 | 4.30* | 1.38* | 0.61* | 0.32* |
| 4-Methyldibenzothiophene sulfone | 4-methyldibenzothiophene 5,5-dioxide | 1.79E+04 | 803.06 | 147.88# | 50.35# | 23.87# | 13.84 C |
| 4-Methyldibenzothiophene | 4-methyldibenzothiophene | 1.84E+06 | 2.51E+04 | 2336.12# | 519.57# | 183.93# | 86.39# |
| 3,6-Dimethyldibenzothiophene oxide | 3,6-dimethyldibenzothiophene 5-oxide | 1664.00 | 42.34 | 5.96* | 1.70* | 0.69* | 0.35* |
| 3,6-Dimethyldibenzothiophene sulfone | 3,6-dimethyldibenzothiophene 5,5-dioxide | 4.41E+04 | 1460.32 | 229.56# | 70.98# | 31.54# | 17.45# |
| 3,6-Dimethyldibenzothiophene | 3,6-dimethyldibenzothiophene | 5.81E+06 | 5.74E+04 | 4486.68# | 895.55# | 294.51# | 131.18# |
| 4,6-Dimethyldibenzothiophene oxide | 4,6-dimethyldibenzothiophene 5-oxide | 2468.00 | 64.61 | 9.24* | 2.67* | 1.10* | 0.56* |

TABLE 5B-continued

| Common Name | IUPAC | | | | | | |
|---|---|---|---|---|---|---|---|
| 4,6-Dimethyldibenzothiophene sulfone | 4,6-dimethyldibenzothiophene 5,5-dioxide | 3.74E+04 | 1317.07 | 214.87# | 68.09# | 30.78# | 17.23# |
| 4,6-Dimethyldibenzothiophene | 4,6-dimethyldibenzothiophene | 5.04E+06 | 5.26E+04 | 4244.75# | 864.88# | 288.56# | 129.90# |
| 2,4-Dimethyldibenzothiophene oxide | 2,4-dimethyldibenzothiophene 5-oxide | 1542.00 | 38.69 | 5.40* | 1.53* | 0.62* | 0.31* |
| 2,4-Dimethyldibenzothiophene sulfone | 2,4-dimethyldibenzothiophene 5,5-dioxide | 3.90E+04 | 1315.83 | 209.43# | 65.32# | 29.20# | 16.22# |
| 2,4-Dimethyldibenzothiophene | 2,4-dimethyldibenzothiophene | 6.02E+06 | 5.87E+04 | 4561.91# | 907.53# | 297.80# | 132.45# |
| 2,4,7-Trimethyldibenzothiophene oxide | 2,4,7-trimethyldibenzothiophene 5-oxide | 4095.00 | 73.74 | 8.64* | 2.20* | 0.83* | 0.39* |
| 2,4,7-Trimethyldibenzothiophene sulfone | 2,4,7-trimethyldibenzothiophene 5,5-dioxide | 9.72E+04 | 2405.49 | 327.16# | 92.76# | 38.89# | 20.63# |
| 2,4,7-Trimethyldibenzothiophene | 2,4,7-trimethyldibenzothiophene | 2.05E+07 | 1.43E+05 | 9262.17# | 1648.89# | 501.70# | 211.35# |
| 4-Ethyldibenzothiophene oxide | 4-ethyldibenzothiophene 5-oxide | 1706.00 | 44.80 | 6.42* | 1.86* | 0.77* | 0.39* |
| 4-Ethyldibenzothiophene sulfone | 4-ethyldibenzothiophene 5,5-dioxide | 5.43E+04 | 1742.29 | 266.57# | 80.89# | 35.46# | 19.43# |
| 4-Ethyldibenzothiophene | 4-ethyldibenzothiophene | 5.28E+06 | 5.35E+04 | 4261.07# | 861.29# | 285.83# | 128.21# |
| 4-Propyldibenzothiophene oxide | 4-propyldibenzothiophene 5-oxide | 4103.00 | 77.28 | 9.25* | 2.39* | 0.91* | 0.43* |
| 4-Propyldibenzothiophene sulfone | 4-propyldibenzothiophene 5,5-dioxide | 1.60E+05 | 3664.87 | 467.12# | 126.57# | 51.37# | 26.63# |
| 4-Propyldibenzothiophene | 4-propyldibenzothiophene | 1.72E+07 | 1.23E+05 | 8147.27# | 1466.21# | 449.52# | 190.48# |
| 2-Butyldibenzothiophene oxide | 2-butyldibenzothiophene 5-oxide | 1.43E+04 | 171.12 | 15.99* | 3.53* | 1.21* | 0.53* |
| 2-Butyldibenzothiophene sulfone | 2-butyldibenzothiophene 5,5-dioxide | 3.38E+05 | 5622.88 | 609.83# | 149.84# | 56.93# | 28.15# |
| 2-Butyldibenzothiophene | 2-butyldibenzothiophene | 7.58E+07 | 3.50E+05 | 1.81E+04 | 2797.58# | 771.74# | 302.98# |
| 2-Pentyldibenzothiophene oxide | 2-pentyldibenzothiophene 5-oxide | 5.25E+04 | 446.27 | 34.69 | 6.86* | 2.17* | 0.90* |
| 2-Pentyldibenzothiophene sulfone | 2-pentyldibenzothiophene 5,5-dioxide | 1.07E+06 | 1.26E+04 | 1135.90 | 248.30# | 87.10# | 40.67# |
| 2-Pentyldibenzothiophene | 2-pentyldibenzothiophene | 2.67E+08 | 8.69E+05 | 3.72E+04 | 5094.73# | 1296.30# | 480.22# |
| 1-Phenyldibenzothiophene oxide | 1-phenyldibenzothiophene 5-oxide | 1.17E+04 | 153.04 | 15.05 | 3.44* | 1.21* | 0.54* |
| 1-Phenyldibenzothiophene sulfone | 1-phenyldibenzothiophene 5,5-dioxide | 3.46E+05 | 5816.08 | 633.65 | 156.05# | 59.46# | 29.50# |
| 1-Phenyldibenzothiophene | 1-phenyldibenzothiophene | 4.77E+07 | 2.34E+05 | 1.26E+04 | 1995.65# | 561.69# | 224.04# |
| 4-Phenyldibenzothiophene oxide | 4-phenyldibenzothiophene 5-oxide | 6.25E+04 | 701.76 | 62.52 | 13.49* | 4.58* | 2.02* |
| 4-Phenyldibenzothiophene sulfone | 4-phenyldibenzothiophene 5,5-dioxide | 3.59E+05 | 5992.57 | 641.92 | 155.98# | 58.82# | 28.95# |
| 4-Phenyldibenzothiophene | 4-phenyldibenzothiophene | 5.26E+07 | 2.47E+05 | 1.28E+04 | 1984.53# | 548.22# | 215.60# |
| Dodecane | Dodecane | 6.02E+08 | 3.70E+06 | 2.27E+05 | 3.89E+04 | 1.16E+04 | 4772.90 |
| Naphthalene | bicyclo[4.4.0]deca-1,3,5,7,9-pentene | 5.55E+04 | 2371.10 | 403.00 | 129.10 | 58.60 | 32.80 |
| Dibutyl sulfoxide | 1-butylsulfinyl-butane | 49.90 | 2.30* | 0.43* | 0.14* | 0.06* | 0.03* |
| Dibutyl sulfone | 1-butylsulfonyl-butane | 324.80 | 31.70# | 9.20 C | 4.20 C | 2.40 C | 1.60 C |
| Dibutyl sulfide | 1-butylsulfanyl-butane | 5.23E+05 | 1.30E+04# | 1701.80# | 464.30# | 188.70# | 97.50# |
| Thiophene sulfide | tetrahydrothiophene 1-oxide | 2.00 | 0.58* | 0.29* | 0.19* | 0.13 | 0.10 |
| Thiophene sulfone | tetrahydrothiophene 1,1-dioxide | 43.10 | 15.90# | 9.00 C | 6.10 C | 4.70 | 3.80 |
| Thiophene | Thiophene | 1819.20 | 190.90# | 53.50# | 23.50# | 13.20 | 8.70 |
| Toluene | Methylbenzene | 1.26E+04 | 909.90 | 207.30 | 80.00 | 41.10 | 25.20 |

| Compound | | Solvent (Acetic Acid W %/Water W %) | | | | |
|---|---|---|---|---|---|---|
| Common Name | IUPAC | 60/40 | 70/30 | 80/20 | 90/10 | 100/0 |
| | | Activity Coefficient | | | | |
| 6-Methylbenzothiophene oxide | 6-methyl-1-benzo(b)thiophene 1-oxide | 0.09* | 0.06 | 0.04 | 0.03 | 0.02 |
| 6-Methylbenzothiophene sulfone | 6-methyl-1-benzo(b)thiophene 1,1-dioxide | 4.40 C | 3.45 | 2.84 | 2.41 | 2.10 |
| 6-Methylbenzothiophene | 6-methyl-1-benzo(b)thiophene | 22.65# | 15.57 | 11.51 | 8.97 | 7.27 |

TABLE 5B-continued

| | | | | | | |
|---|---|---|---|---|---|---|
| 2,6-Dimethylbenzothiophene oxide | 2,6-dimethyl-1-benzo(b)thiophene 1-oxide | 0.07* | 0.05* | 0.03 | 0.02 | 0.02 |
| 2,6-Dimethylbenzothiophene sulfone | 2,6-dimethyl-1-benzo(b)thiophene 1,1-dioxide | 4.54 C | 3.48 C | 2.80 | 2.34 | 2.01 |
| 2,6-Dimethylbenzothiophene | 2,6-dimethyl-1-benzo(b)thiophene | 33.31# | 22.20# | 16.00 | 12.22 | 9.74 |
| 2,3,6-Trimethylbenzothiophene-oxide | 2,3,6-trimethyl-1-benzo(b)thiophene 1-oxide | 0.13* | 0.08* | 0.06* | 0.04* | 0.03 |
| 2,3,6-Trimethylbenzothiophene sulfone | 2,3,6-trimethyl-1-benzo(b)thiophene 1,1-dioxide | 6.44 C | 4.78 C | 3.76 C | 3.08 C | 2.61 |
| 2,3,6-Trimethylbenzothiophene | 2,3,6-trimethyl-1-benzo(b)thiophene | 51.33# | 33.32# | 23.53# | 17.67# | 13.89 |
| Dibenzothiophene oxide | dibenzothiophene 5-oxide | 0.13* | 0.09* | 0.06 | 0.04 | 0.03 |
| Dibenzothiophene sulfone | dibenzothiophene 5,5-dioxide | 6.91 C | 5.15 C | 4.06 | 3.34 | 2.84 |
| Dibenzothiophene | dibenzothiophene | 33.92# | 22.18# | 15.75 | 11.89 | 9.39 |
| 4-Methyldibenzothiophene oxide | 4-methyldibenzothiophene 5-oxide | 0.19* | 0.12* | 0.08* | 0.06 | 0.04 |
| 4-Methyldibenzothiophene sulfone | 4-methyldibenzothiophene 5,5-dioxide | 9.15 C | 6.61 C | 5.09 C | 4.11 | 3.43 |
| 4-Methyldibenzothiophene | 4-methyldibenzothiophene | 48.66# | 31.02# | 21.59# | 16.03 | 12.49 |
| 3,6-Dimethyldibenzothiophene oxide | 3,6-dimethyldibenzothiophene 5-oxide | 0.19* | 0.12* | 0.08* | 0.05* | 0.04 |
| 3,6-Dimethyldibenzothiophene sulfone | 3,6-dimethyldibenzothiophene 5,5-dioxide | 11.13 C | 7.82 C | 5.89 C | 4.67 C | 3.84 |
| 3,6-Dimethyldibenzothiophene | 3,6-dimethyldibenzothiophene | 71.01# | 43.89# | 29.81# | 21.69# | 16.63 |
| 4,6-Dimethyldibenzothiophene oxide | 4,6-dimethyldibenzothiophene 5-oxide | 0.32* | 0.20* | 0.13* | 0.09* | 0.07 |
| 4,6-Dimethyldibenzothiophene sulfone | 4,6-dimethyldibenzothiophene 5,5-dioxide | 11.10 C | 7.85 C | 5.94 C | 4.72 C | 3.89 |
| 4,6-Dimethyldibenzothiophene | 4,6-dimethyldibenzothiophene | 70.89# | 44.10# | 30.10# | 22.00# | 16.92 |
| 2,4-Dimethyldibenzothiophene oxide | 2,4-dimethyldibenzothiophene 5-oxide | 0.17* | 0.11* | 0.07* | 0.05* | 0.03* |
| 2,4-Dimethyldibenzothiophene sulfone | 2,4-dimethyldibenzothiophene 5,5-dioxide | 10.39 C | 7.32 C | 5.52 C | 4.38 C | 3.60 C |
| 2,4-Dimethyldibenzothiophene | 2,4-dimethyldibenzothiophene | 71.62# | 44.23# | 30.02# | 21.83# | 16.73# |
| 2,4,7-Trimethyldibenzothiophene oxide | 2,4,7-trimethyldibenzothiophene 5-oxide | 0.21* | 0.12* | 0.08* | 0.05* | 0.04* |
| 2,4,7-Trimethyldibenzothiophene sulfone | 2,4,7-trimethyldibenzothiophene 5,5-dioxide | 12.75 C | 8.74 C | 6.45 C | 5.02 C | 4.07 C |
| 2,4,7-Trimethyldibenzothiophene | 2,4,7-trimethyldibenzothiophene | 109.72# | 65.64# | 43.45# | 30.96# | 23.32# |
| 4-Ethyldibenzothiophene oxide | 4-ethyldibenzothiophene 5-oxide | 0.22* | 0.14* | 0.09* | 0.06* | 0.04* |
| 4-Ethyldibenzothiophene sulfone | 4-ethyldibenzothiophene 5,5-dioxide | 12.32 C | 8.62 C | 6.47 C | 5.11 C | 4.19 C |
| 4-Ethyldibenzothiophene | 4-ethyldibenzothiophene | 69.78# | 43.31# | 29.52# | 21.55# | 16.56# |
| 4-Propyldibenzothiophene oxide | 4-propyldibenzothiophene 5-oxide | 0.24* | 0.14* | 0.09* | 0.06* | 0.04* |
| 4-Propyldibenzothiophene sulfone | 4-propyldibenzothiophene 5,5-dioxide | 16.20# | 10.97 C | 8.03 C | 6.21 C | 5.01 C |
| 4-Propyldibenzothiophene | 4-propyldibenzothiophene | 99.34# | 59.66# | 39.61# | 28.30# | 21.36# |
| 2-Butyldibenzothiophene oxide | 2-butyldibenzothiophene 5-oxide | 0.27* | 0.15* | 0.09* | 0.06* | 0.04* |
| 2-Butyldibenzothiophene sulfone | 2-butyldibenzothiophene 5,5-dioxide | 16.51# | 10.87 C | 7.77 C | 5.90 C | 4.68 C |
| 2-Butyldibenzothiophene | 2-butyldibenzothiophene | 149.17# | 85.65# | 54.86# | 38.07# | 28.05# |
| 2-Pentyldibenzothiophene oxide | 2-pentyldibenzothiophene 5-oxide | 0.44* | 0.24* | 0.15* | 0.09* | 0.06* |
| 2-Pentyldibenzothiophene sulfone | 2-pentyldibenzothiophene 5,5-dioxide | 22.85# | 14.55 C | 10.13 C | 7.53 C | 5.87 C |
| 2-Pentyldibenzothiophene | 2-pentyldibenzothiophene | 226.35# | 125.64# | 78.35# | 53.20# | 38.49# |
| 1-Phenyldibenzothiophene oxide | 1-phenyldibenzothiophene 5-oxide | 0.28* | 0.16* | 0.10* | 0.07* | 0.05* |

TABLE 5B-continued

| | | | | | | |
|---|---|---|---|---|---|---|
| 1-Phenyldibenzothiophene sulfone | 1-phenyldibenzothiophene 5,5-dioxide | 17.37# | 11.49 C | 8.25 C | 6.29 C | 5.01 C |
| 1-Phenyldibenzothiophene | 1-phenyldibenzothiophene | 111.74# | 64.86# | 41.93# | 29.33# | 21.76# |
| 4-Phenyldibenzothiophene oxide | 4-phenyldibenzothiophene 5-oxide | 1.05* | 0.61* | 0.39* | 0.26* | 0.18* |
| 4-Phenyldibenzothiophene sulfone | 4-phenyldibenzothiophene 5,5-dioxide | 16.94# | 11.14 C | 7.97 C | 6.05 C | 4.81 C |
| 4-Phenyldibenzothiophene | 4-phenyldibenzothiophene | 106.36# | 61.21# | 39.29# | 27.33# | 20.18# |
| Dodecane | Dodecane | 2437.20 | 1437.60 | 939.70 | 662.20 | 493.80 |
| Naphthalene | bicyclo[4.4.0]deca-1,3,5,7,9-pentene | 21.10 | 14.90 | 11.20 | 8.90 | 7.30 |
| Dibutyl sulfoxide | 1-butylsulfinyl-butane | 0.02* | 0.01* | 0.01* | 0.00* | 0.00* |
| Dibutyl sulfone | 1-butylsulfonyl-butane | 1.10 C | 0.90 C | 0.70 C | 0.60 C | 0.50 C |
| Dibutyl sulfide | 1-butylsulfanyl-butane | 58.80# | 39.50# | 28.50# | 21.80# | 17.40# |
| Thiophene sulfide | tetrahydrothiophene 1-oxide | 0.08 | 0.06 | 0.05 | 0.04 | 0.03 |
| Thiophene sulfone | tetrahydrothiophene 1,1-dioxide | 3.20 | 2.90 | 2.60 | 2.40 | 2.20 |
| Thiophene | Thiophene | 6.30 | 4.80 | 3.90 | 3.30 | 2.80 |
| Toluene | Methylbenzene | 17.30 | 12.90 | 10.10 | 8.30 | 7.00 |

Formic Acid Formulations

In yet another embodiment of the process described herein, the solvent formulation comprises an aqueous solution of formic acid. An aqueous solution of formic acid having a concentration of about 2.5 W % to about 50 W % is particularly useful as a selective solvent formulation for extraction of sulfoxide products, and an aqueous solution of formic acid having a concentration of about 50 W % to about 70 W % is particularly suitable for extraction of bulky sulfoxidation products, i.e., sulfoxides and sulfones. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. For non-bulky sulfoxide products, the concentration of the aqueous formic acid solution can be about 2.5 W % to about 30 W %, which will extract the non-bulky sulfoxidation products, while minimizing co-extraction of certain sulfones, untreated organosulfur compounds, non-heteroatom aromatics and other hydrocarbons. For bulky sulfoxide products and/or bulky sulfoxidation products, the concentration of the aqueous formic acid solution can be about 30 W % to about 70 W %, which will desirably extract the bulky sulfoxide products and/or bulky sulfoxidation products, while minimizing co-extraction of non-heteroatom aromatics and other hydrocarbons.

In an extractive simulation, COSMO-RS software was used to simulate γ for selective extraction of oxidized model A fuel by solvent formulations of aqueous formic acid. Formic acid is desirable as a polar organic solvent due to its relatively low boiling point, thereby and separation from the sulfoxide products or the sulfoxidation products.

Figure 18:
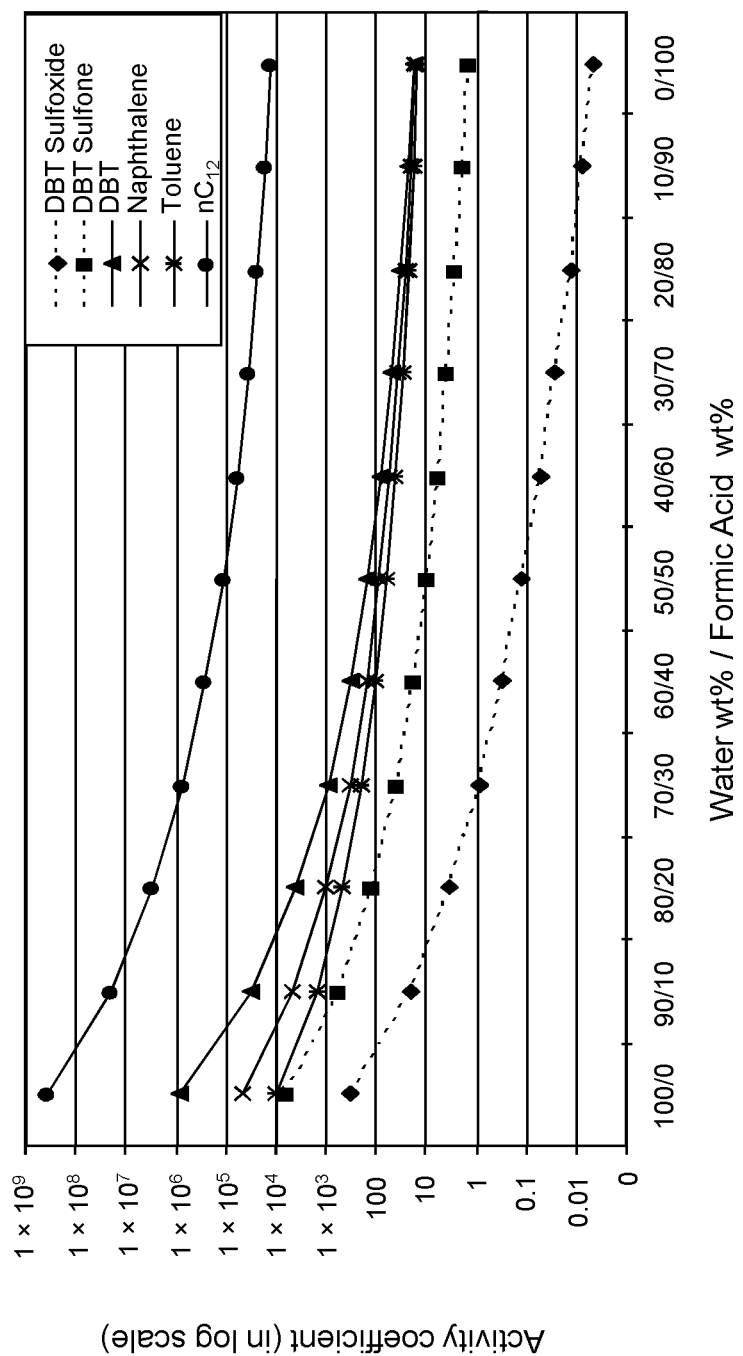
FIGS. 18, 19 and 20 are plots of computational models of the activity coefficient values for a range of concentrations of a formic acid solvent formulation for sulfoxidation products of DBT, thiophene and dibutyl sulfide compounds, respectively, relative to other components in a hydrocarbon mixture.
Figure 19:
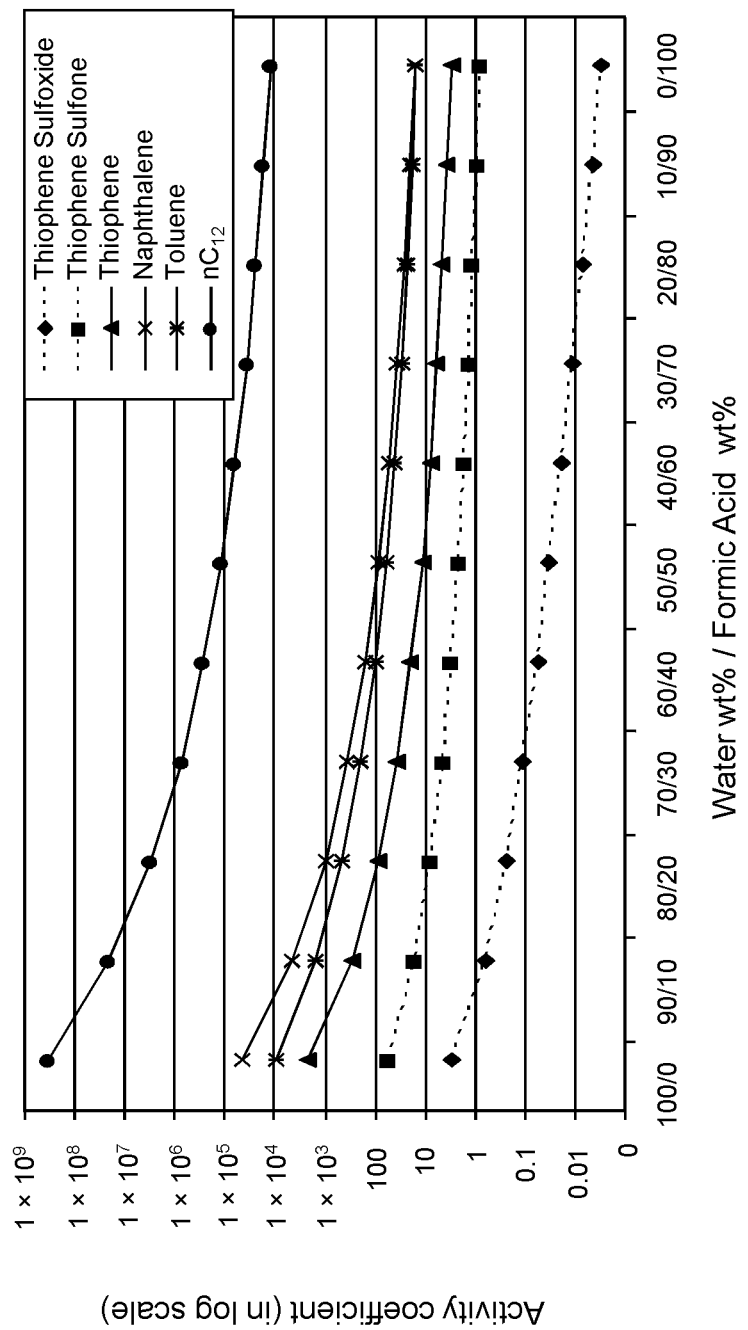
Figure 20:
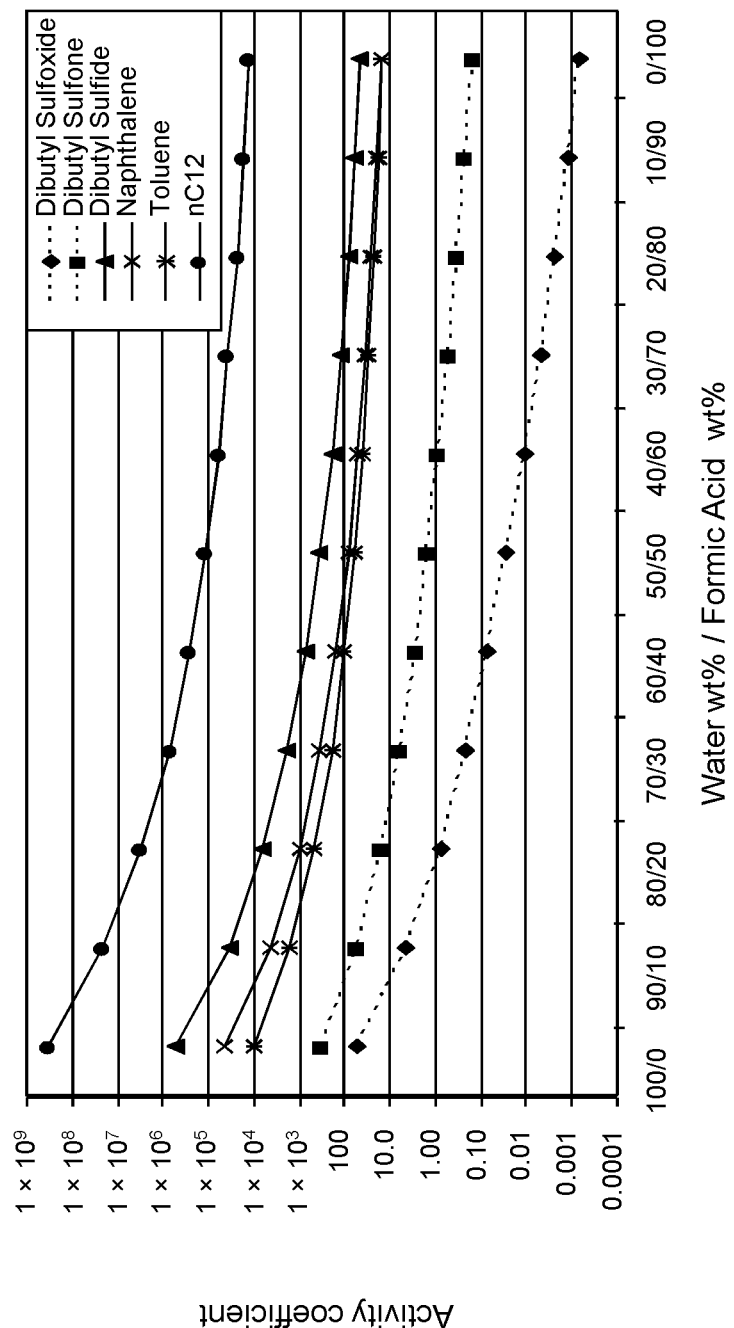

Table 6A illustrates the activity coefficient of different concentrations of aqueous formic acid. Based on the activity coefficient values in Table 6A, a useful aqueous formic acid selective solvent formulation has a concentration of about 30 W % to about 40 W % for extraction of DBT sulfoxide, with minimal co-extraction of certain sulfones, untreated organosulfur compounds, aromatics and other hydrocarbons, as shown in FIG. 18. It is also apparent from FIG. 18 and the data in Table 6A that a suitable concentration of formic acid is about 50 W % to about 70 W % for extraction of DBT sulfoxide combined with DBT sulfone, with minimal co-extraction of aromatics and other hydrocarbons. A concentration of formic acid of about 50 W % to about 70 W % is also useful for extraction of thiophene sulfoxide, thiophene sulfone, dibutyl sulfoxide and dibutyl sulfone. If the target sulfoxidation products are primarily non-bulky sulfoxidation products such as thiophene sulfoxide and dibutyl sulfoxide, a suitable selective solvent formulation will have about 5 W % to about 20 W % aqueous formic acid, as shown in FIGS. 19 and 20. Sulfones of thiophene and dibutyl can be extracted using about 30 W % to about 40 W % aqueous formic acid.

In another extraction simulation, COSMO-RS software was used to simulate γ for formulations of aqueous formic acid as extraction solvents for oxidized model B fuel. The results are shown in Table 6B. Activity coefficient values as shown in Table 6B indicate that certain formulations of aqueous formic acid will selectively extract bulky sulfoxide products while minimizing co-extraction of their corresponding sulfones and underlying organosulfur compounds. In addition, activity coefficient values as shown in Table 6B indicate that certain formulations of aqueous formic acid will selectively extract bulky sulfoxidation products, including sulfoxides and sulfones, with minimal co-extraction of aromatics, untreated organosulfur compounds and other hydrocarbons. Based on the activity coefficient values in Table 6B, a useful formic acid selective solvent formulation has a concentration of about 20 W % to about 60 W % for selective extraction of bulky sulfoxide products including alkyl and dialkyl derivatives of benzothiophenes and dibenzothiophenes. In addition, aqueous formic acid selective solvent formulations of about 50 W % to about 70 W % are also useful for extraction of bulky sulfoxidation products including sulfoxides and sulfones with minimal co-extraction of aromatics, untreated organosulfur compounds and other hydrocarbons.

In Table 6B, activity coefficients for targeted sulfoxides for which extraction is favored are marked with an asterisk ("*"), activity coefficients for non-targeted underlying organosulfur compounds and in certain cases corresponding sulfones for which co-extraction is minimized are marked with a pound symbol ("#"). Furthermore, activity coefficients for targeted sulfones for which extraction is favored (i.e., in combination with corresponding sulfoxides) are marked with a letter "C".

It is noted that although the activity coefficient values for certain high concentration formic acid formulations indicate favorable extraction of certain bulky or non-bulky sulfoxidation products (including sulfoxides and sulfones), these high concentration formic acid formulations (e.g., greater than 70 W %) also extract untargeted species and therefore are not particularly desirable for extraction of a broad array of organosulfur oxidation products.

TABLE 6A

| Compound | Solvent (Formic Acid W %/Water W %) | | | | | | | | | | |
|---|---|---|---|---|---|---|---|---|---|---|---|
| | 0/100 | 10/90 | 20/80 | 30/70 | 40/60 | 50/50 | 60/40 | 70/30 | 80/20 | 90/10 | 100/0 |
| | Activity Coefficient | | | | | | | | | | |
| dibenzothiophene 5-oxide (DBT sulfoxide) | 321.00 | 20.10 | 3.29 | 0.87 | 0.30 | 0.12 | 0.05 | 0.03 | 0.01 | 0.01 | 0.00 |
| dibenzothiophene 5,5-dioxide (DBT sulfone) | 6063.00 | 550.00 | 116.00 | 38.50 | 17.00 | 8.94 | 5.37 | 3.56 | 2.51 | 1.86 | 1.43 |
| dibenzothiophene (DBT) | 7.90E+05 | 3.03E+04 | 3866.00 | 925.00 | 327.01 | 147.00 | 79.00 | 48.40 | 32.10 | 22.90 | 17.30 |
| 1-butylsulfinyl-butane (Di-butyl Sulfoxide) | 51.40 | 4.35 | 0.79 | 0.21 | 0.07 | 0.03 | 0.01 | 0.00 | 0.00 | 0.00 | 0.00 |
| 1-butylsulfonyl-butane (Di-butyl Sulfone) | 337.00 | 53.50 | 14.90 | 5.75 | 2.72 | 1.45 | 0.83 | 0.51 | 0.33 | 0.22 | 0.15 |
| 1-butylsulfanyl-butane (Di-butyl Sulfide) | 5.04E+05 | 3.60E+04 | 6248.00 | 1808.00 | 706.00 | 344.00 | 192.00 | 120.00 | 81.40 | 58.00 | 43.80 |
| Thiophene Sulfoxide | 2.83 | 0.63 | 0.23 | 0.11 | 0.06 | 0.03 | 0.02 | 0.01 | 0.01 | 0.00 | 0.00 |
| Thiophene Sulfone | 49.40 | 15.80 | 7.39 | 4.35 | 2.89 | 2.10 | 1.62 | 1.30 | 1.06 | 0.90 | 0.77 |
| Thiophene | 2208.00 | 299.00 | 84.80 | 35.50 | 18.80 | 11.50 | 7.85 | 5.75 | 4.48 | 3.63 | 3.03 |
| Naphthalene | 4.44E+04 | 4447.00 | 992.00 | 340.00 | 156.00 | 84.80 | 53.00 | 36.20 | 26.60 | 20.50 | 16.40 |
| Toluene | 9799.00 | 1541.00 | 455.00 | 191.00 | 99.50 | 60.30 | 40.80 | 29.70 | 22.90 | 18.40 | 15.30 |
| $nC_{12}$ | 3.52E+08 | 2.02E+07 | 2.93E+06 | 7.29E+05 | 2.58E+05 | 1.16E+05 | 6.11E+04 | 3.63E+04 | 2.39E+04 | 1.68E+04 | 1.23E+04 |

TABLE 6B

| Compound | | Solvent (Formic Acid W %/Water W %) | | | | | |
|---|---|---|---|---|---|---|---|
| Common Name | IUPAC | 0/100 | 10/90 | 20/80 | 30/70 | 40/60 | 50/50 |
| | | Activity Coefficient | | | | | |
| 6-Methylbenzothiophene oxide | 6-methyl-1-benzo(b)thiophene 1-oxide | 47.00 | 4.66* | 1.00* | 0.31* | 0.12* | 0.05* |
| 6-Methylbenzothiophene sulfone | 6-methyl-1-benzo(b)thiophene 1,1-dioxide | 988.00 | 137.92# | 37.53# | 14.86 C | 7.42 C | 4.33 C |
| 6-Methylbenzothiophene | 6-methyl-1-benzo(b)thiophene | 1.20E+05 | 7996.47# | 1404.85# | 420.07# | 173.74# | 89.09# |
| 2,6-Dimethylbenzothiophene oxide | 2,6-dimethyl-1-benzo(b)thiophene 1-oxide | 88.00 | 6.96* | 1.27* | 0.35* | 0.12* | 0.05* |
| 2,6-Dimethylbenzothiophene sulfone | 2,6-dimethyl-1-benzo(b)thiophene 1,1-dioxide | 1967.00 | 224.00# | 53.33# | 19.19# | 8.91 C | 4.90 C |
| 2,6-Dimethylbenzothiophene | 2,6-dimethyl-1-benzo(b)thiophene | 3.87E+05 | 2.10E+04# | 3214.43# | 871.68# | 335.39# | 162.83# |
| 2,3,6-Trimethylbenzothiophene-oxide | 2,3,6-trimethyl-1-benzo(b)thiophene 1-oxide | 313.00 | 20.72 | 3.38* | 0.87* | 0.29* | 0.12* |
| 2,3,6-Trimethylbenzothiophene sulfone | 2,3,6-trimethyl-1-benzo(b)thiophene 1,1-dioxide | 5917.00 | 560.48 | 118.20# | 39.07# | 17.04# | 8.95 C |
| 2,3,6-Trimethylbenzothiophene | 2,3,6-trimethyl-1-benzo(b)thiophene | 1.17E+06 | 5.34E+04 | 7260.63# | 1812.20# | 655.91# | 304.08# |
| Dibenzothiophene oxide | dibenzothiophene 5-oxide | 251.00 | 16.05* | 2.61* | 0.68* | 0.23* | 0.09* |
| Dibenzothiophene sulfone | dibenzothiophene 5,5-dioxide | 6267.00 | 558.13# | 115.43# | 38.08# | 16.73# | 8.89 C |
| Dibenzothiophene | dibenzothiophene | 6.67E+05 | 2.90E+04# | 3898.94# | 975.20# | 355.37# | 165.95# |
| 4-Methyldibenzothiophene oxide | 4-methyldibenzothiophene 5-oxide | 718.00 | 38.85 | 5.66* | 1.37* | 0.44* | 0.17* |
| 4-Methyldibenzothiophene sulfone | 4-methyldibenzothiophene 5,5-dioxide | 1.79E+04 | 1321.69 | 241.96# | 73.25# | 30.20# | 15.30 C |
| 4-Methyldibenzothiophene | 4-methyldibenzothiophene | 1.84E+06 | 6.73E+04# | 8077.23# | 1862.05# | 638.81# | 285.02# |
| 3,6-Dimethyldibenzothiophene oxide | 3,6-dimethyldibenzothiophene 5-oxide | 1664.00 | 65.78 | 8.16* | 1.75* | 0.51* | 0.18* |

TABLE 6B-continued

| | | | | | | | |
|---|---|---|---|---|---|---|---|
| 3,6-Dimethyldibenzothiophene sulfone | 3,6-dimethyldibenzothiophene 5,5-dioxide | 4.41E+04 | 2372.72 | 381.46# | 105.25# | 40.44# | 19.38# |
| 3,6-Dimethyldibenzothiophene | 3,6-dimethyldibenzothiophene | 5.81E+06 | 1.78E+05 | 1.86E+04# | 3874.72# | 1235.12# | 521.29# |
| 4,6-Dimethyldibenzothiophene oxide | 4,6-dimethyldibenzothiophene 5-oxide | 2468.00 | 72.03 | 9.03* | 1.96* | 0.58* | 0.21* |
| 4,6-Dimethyldibenzothiophene sulfone | 4,6-dimethyldibenzothiophene 5,5-dioxide | 3.74E+04 | 2657.10 | 424.30# | 116.55# | 44.66# | 21.38# |
| 4,6-Dimethyldibenzothiophene | 4,6-dimethyldibenzothiophene | 5.04E+06 | 1.73E+05 | 1.80E+04# | 3771.02# | 1203.06# | 508.06# |
| 2,4-Dimethyldibenzothiophene oxide | 2,4-dimethyldibenzothiophene 5-oxide | 1542.00 | 112.92 | 14.77* | 3.33* | 1.03* | 0.38* |
| 2,4-Dimethyldibenzothiophene sulfone | 2,4-dimethyldibenzothiophene 5,5-dioxide | 3.90E+04 | 2412.31 | 403.33# | 114.42# | 44.88# | 21.86# |
| 2,4-Dimethyldibenzothiophene | 2,4-dimethyldibenzothiophene | 6.02E+06 | 1.56E+05 | 1.68E+04# | 3584.22# | 1160.45# | 495.62# |
| 2,4,7-Trimethyldibenzothiophene oxide | 2,4,7-trimethyldibenzothiophene 5-oxide | 4095.00 | 140.32 | 15.05* | 2.92* | 0.79* | 0.26* |
| 2,4,7-Trimethyldibenzothiophene sulfone | 2,4,7-trimethyldibenzothiophene 5,5-dioxide | 9.72E+04 | 4760.04 | 664.33# | 165.77# | 59.04# | 26.66# |
| 2,4,7-Trimethyldibenzothiophene | 2,4,7-trimethyldibenzothiophene | 2.05E+07 | 4.87E+05 | 4.40E+04# | 8297.46# | 2455.13# | 979.44# |
| 4-Ethyldibenzothiophene oxide | 4-ethyldibenzothiophene 5-oxide | 1706.00 | 76.65 | 9.88* | 2.19* | 0.66* | 0.24* |
| 4-Ethyldibenzothiophene sulfone | 4-ethyldibenzothiophene 5,5-dioxide | 5.43E+04 | 3318.88 | 535.45# | 148.47# | 57.46# | 27.79# |
| 4-Ethyldibenzothiophene | 4-ethyldibenzothiophene | 5.28E+06 | 1.63E+05 | 1.74E+04# | 3715.68# | 1202.49# | 513.46# |
| 4-Propyldibenzothiophene oxide | 4-propyldibenzothiophene 5-oxide | 4103.00 | 149.01 | 16.62 | 3.32* | 0.92* | 0.32* |
| 4-Propyldibenzothiophene sulfone | 4-propyldibenzothiophene 5,5-dioxide | 1.60E+05 | 7954.43 | 1116.39 | 280.50# | 100.92# | 46.18# |
| 4-Propyldibenzothiophene | 4-propyldibenzothiophene | 1.72E+07 | 4.27E+05 | 3.96E+04 | 7627.44# | 2291.23# | 924.80# |
| 2-Butyldibenzothiophene oxide | 2-butyldibenzothiophene 5-oxide | 1.43E+04 | 380.74 | 34.47 | 5.92* | 1.46* | 0.46* |
| 2-Butyldibenzothiophene sulfone | 2-butyldibenzothiophene 5,5-dioxide | 3.38E+05 | 1.31E+04 | 1552.18 | 345.81# | 113.43# | 48.19# |
| 2-Butyldibenzothiophene | 2-butyldibenzothiophene | 7.58E+07 | 1.42E+06 | 1.09E+05 | 1.83E+04# | 4987.54# | 1867.14# |
| 2-Pentyldibenzothiophene oxide | 2-pentyldibenzothiophene 5-oxide | 5.25E+04 | 1139.55 | 90.23 | 14.14* | 3.28* | 0.97* |
| 2-Pentyldibenzothiophene sulfone | 2-pentyldibenzothiophene 5,5-dioxide | 1.07E+06 | 3.36E+04 | 3462.04 | 697.84# | 212.60# | 85.42# |
| 2-Pentyldibenzothiophene | 2-pentyldibenzothiophene | 2.67E+08 | 4.03E+06 | 2.68E+05 | 4.08E+04# | 1.03E+04# | 3644.60# |
| 1-Phenyldibenzothiophene oxide | 1-phenyldibenzothiophene 5-oxide | 1.17E+04 | 289.12 | 25.56 | 4.37* | 1.09* | 0.34* |
| 1-Phenyldibenzothiophene sulfone | 1-phenyldibenzothiophene 5,5-dioxide | 3.46E+05 | 1.18E+04 | 1334.18 | 289.97# | 94.21# | 39.97# |
| 1-Phenyldibenzothiophene | 1-phenyldibenzothiophene | 4.77E+07 | 8.08E+05 | 5.97E+04 | 9896.86# | 2679.68# | 1002.89# |
| 4-Phenyldibenzothiophene oxide | 4-phenyldibenzothiophene 5-oxide | 6.25E+04 | 1472.81 | 127.96 | 22.10 | 5.68* | 1.88* |
| 4-Phenyldibenzothiophene sulfone | 4-phenyldibenzothiophene 5,5-dioxide | 3.59E+05 | 1.22E+04 | 1364.82 | 295.10 | 95.56# | 40.45# |
| 4-Phenyldibenzothiophene | 4-phenyldibenzothiophene | 5.26E+07 | 8.50E+05 | 6.06E+04 | 9785.16 | 2597.17# | 957.22# |
| Dodecane | Dodecane | 6.02E+08 | 2.50E+07 | 2.99E+06 | 6.61E+05 | 2.16E+05 | 9.21E+04 |
| Naphthalene | bicyclo[4.4.0]deca-1,3,5,7,9-pentene | 5.55E+04 | 5137.60 | 1085.50 | 365.60 | 164.40 | 89.70 |
| Dibutyl sulfoxide | 1-butylsulfinyl-butane | 49.90 | 3.80* | 0.60* | 0.16* | 0.05* | 0.02* |
| Dibutyl sulfone | 1-butylsulfonyl-butane | 324.80 | 44.30# | 11.30 C | 4.10 C | 1.80 C | 0.90 C |
| Dibutyl sulfide | 1-butylsulfanyl-butane | 5.23E+05 | 3.73E+04# | 6457.00# | 1854.50# | 732.00# | 358.00# |
| Thiophene sulfide | tetrahydrothiophene 1-oxide | 2.00* | 0.50* | 0.19* | 0.09* | 0.05* | 0.03 |
| Thiophene sulfone | tetrahydrothiophene 1,1-dioxide | 43.10# | 14.40 C | 6.90 C | 4.10 C | 2.70 C | 2.00 |
| Thiophene | Thiophene | 1819.20# | 292.10# | 90.50# | 40.10# | 22.10# | 14.00 |
| Toluene | Methylbenzene | 1.26E+04 | 1811.50 | 505.50 | 205.70 | 105.90 | 63.80 |

TABLE 6B-continued

| Compound | | Solvent (Formic Acid W %/Water W %) | | | | |
|---|---|---|---|---|---|---|
| | | 60/40 | 70/30 | 80/20 | 90/10 | 100/0 |
| Common Name | IUPAC | Activity Coefficient | | | | |
| 6-Methylbenzothiophene oxide | 6-methyl-1-benzo(b)thiophene 1-oxide | 0.03* | 0.01* | 0.01* | 0.00* | 0.00 |
| 6-Methylbenzothiophene sulfone | 6-methyl-1-benzo(b)thiophene 1,1-dioxide | 2.81 $^C$ | 1.97 $^C$ | 1.45 $^C$ | 1.11 $^C$ | 0.89 |
| 6-Methylbenzothiophene | 6-methyl-1-benzo(b)thiophene | 52.96# | 34.95# | 24.90# | 18.76# | 14.79 |
| 2,6-Dimethylbenzothiophene oxide | 2,6-dimethyl-1-benzo(b)thiophene 1-oxide | 0.02* | 0.01* | 0.01* | 0.00* | 0.00* |
| 2,6-Dimethylbenzothiophene sulfone | 2,6-dimethyl-1-benzo(b)thiophene 1,1-dioxide | 3.03 $^C$ | 2.03 $^C$ | 1.45 $^C$ | 1.07 $^C$ | 0.83 $^C$ |
| 2,6-Dimethylbenzothiophene | 2,6-dimethyl-1-benzo(b)thiophene | 92.76# | 59.17# | 41.02# | 30.20# | 23.37# |
| 2,3,6-Trimethylbenzothiophene-oxide | 2,3,6-trimethyl-1-benzo(b)thiophene 1-oxide | 0.05* | 0.02* | 0.01* | 0.01* | 0.00* |
| 2,3,6-Trimethylbenzothiophene sulfone | 2,3,6-trimethyl-1-benzo(b)thiophene 1,1-dioxide | 5.35 $^C$ | 3.49 $^C$ | 2.43 $^C$ | 1.78 $^C$ | 1.36 $^C$ |
| 2,3,6-Trimethylbenzothiophene | 2,3,6-trimethyl-1-benzo(b)thiophene | 167.16# | 103.64# | 70.22# | 50.73# | 38.64# |
| Dibenzothiophene oxide | dibenzothiophene 5-oxide | 0.04* | 0.02* | 0.01* | 0.01* | 0.00* |
| Dibenzothiophene sulfone | dibenzothiophene 5,5-dioxide | 5.39 $^C$ | 3.57 $^C$ | 2.53 $^C$ | 1.89 $^C$ | 1.47 $^C$ |
| Dibenzothiophene | dibenzothiophene | 91.86# | 57.34# | 39.09# | 28.41# | 21.74# |
| 4-Methyldibenzothiophene oxide | 4-methyldibenzothiophene 5-oxide | 0.07* | 0.04* | 0.02* | 0.01* | 0.01* |
| 4-Methyldibenzothiophene sulfone | 4-methyldibenzothiophene 5,5-dioxide | 8.94 $^C$ | 5.76 $^C$ | 3.99 $^C$ | 2.91 $^C$ | 2.23 $^C$ |
| 4-Methyldibenzothiophene | 4-methyldibenzothiophene | 152.30# | 92.43# | 61.59# | 43.93# | 33.10# |
| 3,6-Dimethyldibenzothiophene oxide | 3,6-dimethyldibenzothiophene 5-oxide | 0.07* | 0.03* | 0.02* | 0.01* | 0.01* |
| 3,6-Dimethyldibenzothiophene sulfone | 3,6-dimethyldibenzothiophene 5,5-dioxide | 10.82 $^C$ | 6.70 $^C$ | 4.49 $^C$ | 3.18 $^C$ | 2.38 $^C$ |
| 3,6-Dimethyldibenzothiophene | 3,6-dimethyldibenzothiophene | 266.77# | 156.42# | 101.35# | 70.62# | 52.19# |
| 4,6-Dimethyldibenzothiophene oxide | 4,6-dimethyldibenzothiophene 5-oxide | 0.09* | 0.04* | 0.02* | 0.01* | 0.01* |
| 4,6-Dimethyldibenzothiophene sulfone | 4,6-dimethyldibenzothiophene 5,5-dioxide | 11.93 $^C$ | 7.40 $^C$ | 4.96 $^C$ | 3.52 $^C$ | 2.64 $^C$ |
| 4,6-Dimethyldibenzothiophene | 4,6-dimethyldibenzothiophene | 260.12# | 152.57# | 98.89# | 68.92# | 50.95# |
| 2,4-Dimethyldibenzothiophene oxide | 2,4-dimethyldibenzothiophene 5-oxide | 0.16* | 0.08* | 0.04* | 0.02* | 0.01* |
| 2,4-Dimethyldibenzothiophene sulfone | 2,4-dimethyldibenzothiophene 5,5-dioxide | 12.36 $^C$ | 7.74 $^C$ | 5.24 $^C$ | 3.74 $^C$ | 2.82 $^C$ |
| 2,4-Dimethyldibenzothiophene | 2,4-dimethyldibenzothiophene | 256.02# | 151.26# | 98.62# | 69.07# | 51.28# |
| 2,4,7-Trimethyldibenzothiophene oxide | 2,4,7-trimethyldibenzothiophene 5-oxide | 0.10* | 0.04* | 0.02* | 0.01* | 0.01* |
| 2,4,7-Trimethyldibenzothiophene sulfone | 2,4,7-trimethyldibenzothiophene 5,5-dioxide | 14.18 $^C$ | 8.44 $^C$ | 5.46 $^C$ | 3.76 $^C$ | 2.74 $^C$ |
| 2,4,7-Trimethyldibenzothiophene | 2,4,7-trimethyldibenzothiophene | 479.76# | 271.64# | 171.09# | 116.42# | 84.38# |
| 4-Ethyldibenzothiophene oxide | 4-ethyldibenzothiophene 5-oxide | 0.10* | 0.05* | 0.02* | 0.01* | 0.01* |
| 4-Ethyldibenzothiophene sulfone | 4-ethyldibenzothiophene 5,5-dioxide | 15.68 $^C$ | 9.84 $^C$ | 6.67 $^C$ | 4.80 $^C$ | 3.63 $^C$ |
| 4-Ethyldibenzothiophene | 4-ethyldibenzothiophene | 265.19# | 156.66# | 102.14# | 71.54# | 53.11# |
| 4-Propyldibenzothiophene oxide | 4-propyldibenzothiophene 5-oxide | 0.13* | 0.06* | 0.03* | 0.01* | 0.01* |

TABLE 6B-continued

| | | | | | | |
|---|---|---|---|---|---|---|
| 4-Propyldibenzothiophene sulfone | 4-propyldibenzothiophene 5,5-dioxide | 24.95# | 15.12 C | 9.98 C | 7.01 C | 5.20 C |
| 4-Propyldibenzothiophene | 4-propyldibenzothiophene | 457.22# | 260.88# | 165.37# | 113.16# | 82.40# |
| 2-Butyldibenzothiophene oxide | 2-butyldibenzothiophene 5-oxide | 0.17* | 0.07* | 0.03* | 0.02* | 0.01* |
| 2-Butyldibenzothiophene sulfone | 2-butyldibenzothiophene 5,5-dioxide | 24.48# | 14.06 C | 8.85 C | 5.95 C | 4.26 C |
| 2-Butyldibenzothiophene | 2-butyldibenzothiophene | 870.44# | 473.86# | 289.12# | 191.64# | 135.89# |
| 2-Pentyldibenzothiophene oxide | 2-pentyldibenzothiophene 5-oxide | 0.34* | 0.14* | 0.06* | 0.03* | 0.02* |
| 2-Pentyldibenzothiophene sulfone | 2-pentyldibenzothiophene 5,5-dioxide | 41.54# | 23.05# | 14.11 C | 9.27 C | 6.50 C |
| 2-Pentyldibenzothiophene | 2-pentyldibenzothiophene | 1626.19# | 854.93# | 507.09# | 328.32# | 228.33# |
| 1-Phenyldibenzothiophene oxide | 1-phenyldibenzothiophene 5-oxide | 0.13* | 0.05* | 0.02* | 0.01* | 0.01* |
| 1-Phenyldibenzothiophene sulfone | 1-phenyldibenzothiophene 5,5-dioxide | 20.37# | 11.79 C | 7.49 C | 5.09 C | 3.68 C |
| 1-Phenyldibenzothiophene | 1-phenyldibenzothiophene | 468.53# | 255.95# | 156.80# | 104.39# | 74.32# |
| 4-Phenyldibenzothiophene oxide | 4-phenyldibenzothiophene 5-oxide | 0.74* | 0.33* | 0.16* | 0.09* | 0.05* |
| 4-Phenyldibenzothiophene sulfone | 4-phenyldibenzothiophene 5,5-dioxide | 20.59# | 11.91 C | 7.56 C | 5.14 C | 3.72 C |
| 4-Phenyldibenzothiophene | 4-phenyldibenzothiophene | 441.88# | 239.11# | 145.36# | 96.15# | 68.09# |
| Dodecane | Dodecane | 4.72E+04 | 2.75E+04 | 1.77E+04 | 1.23E+04 | 9012.40 |
| Naphthalene | bicyclo[4.4.0]deca-1,3,5,7,9-pentene | 55.90 | 38.30 | 28.10 | 21.80 | 17.50 |
| Dibutyl sulfoxide | 1-butylsulfinyl-butane | 0.01* | 0.00* | 0.00* | 0.00* | 0.00* |
| Dibutyl sulfone | 1-butylsulfonyl-butane | 0.50 C | 0.32 C | 0.20 C | 0.13 C | 0.09 C |
| Dibutyl sulfide | 1-butylsulfanyl-butane | 203.00# | 128.00# | 87.40# | 63.40# | 48.10# |
| Thiophene sulfide | tetrahydrothiophene 1-oxide | 0.02 | 0.01 | 0.01 | 0.00 | 0.00 |
| Thiophene sulfone | tetrahydrothiophene 1,1-dioxide | 1.50 | 1.20 | 1.00 | 0.90 | 0.80 |
| Thiophene | Thiophene | 9.80 | 7.40 | 5.90 | 4.80 | 4.10 |
| Toluene | Methylbenzene | 42.90 | 31.20 | 24.00 | 19.30 | 16.10 |

Figure 21:
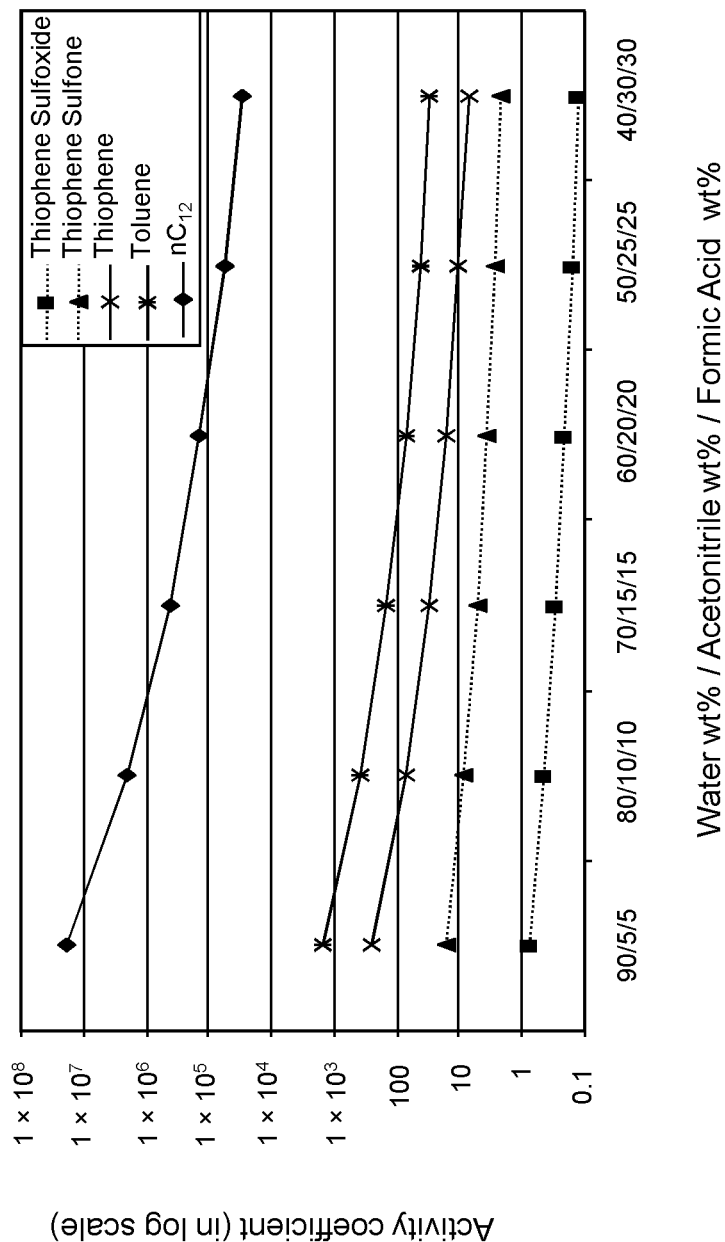
FIGS. 21 and 22 are plots of computational models of the activity coefficient values for a range of concentrations of an acetonitrile/formic acid aqueous solvent formulation for sulfoxidation products of thiophene and DBT, respectively, relative to other components in a hydrocarbon mixture.
Figure 22:
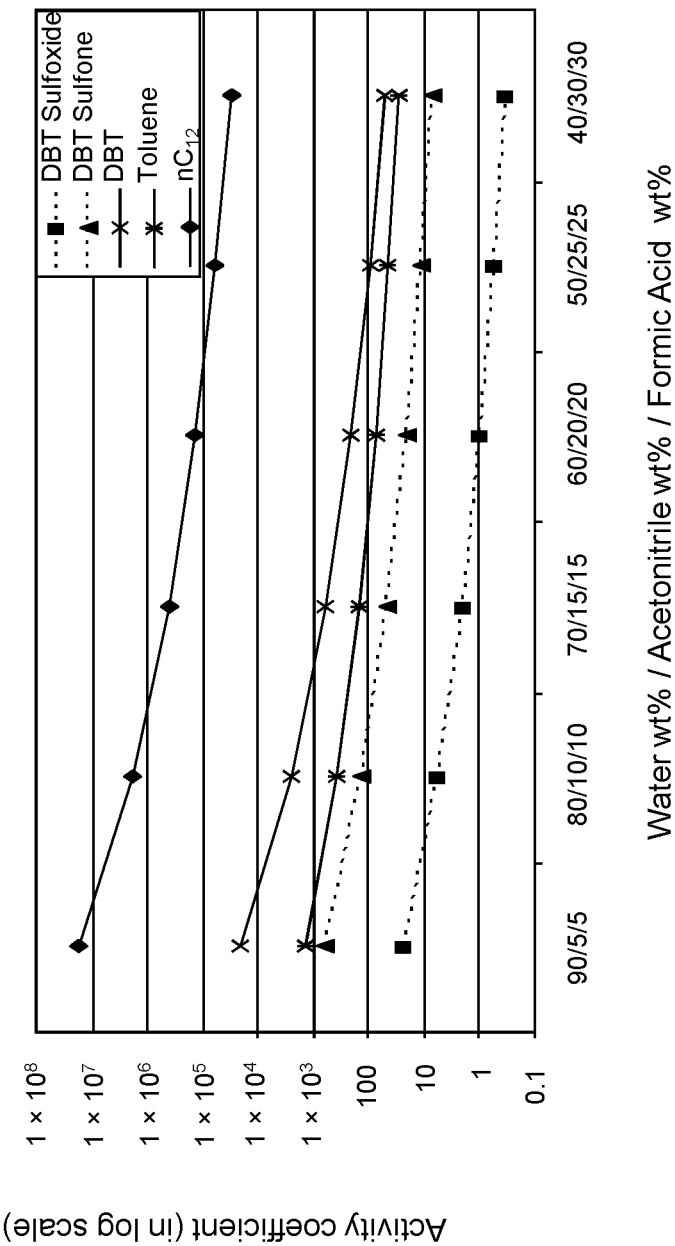

In a further embodiment of the present invention, the solvent formulation comprises an aqueous solution of acetonitrile and formic acid. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. In an extractive simulation, COSMO-RS software was used to simulate γ for selective extraction of oxidized model A fuel by solvent formulations of aqueous formic acid and acetonitrile. Table 7A illustrates the activity coefficient of different concentrations of aqueous formic acid/acetonitrile. Based on the activity coefficient values in Table 7A, a useful aqueous formic acid/acetonitrile selective solvent formulation has a concentration of 10 W % formic acid, 10 W % acetonitrile and 80 W % water for extraction of thiophene sulfoxide and sulfone, as shown in FIG. 21. It is also apparent from FIG. 22 and the data in Table 7A that a suitable concentration of 25 W % formic acid. 25 W % acetonitrile and 50 W % water for extraction for extraction of DBT sulfoxide combined with DBT sulfone is effective.

TABLE 7A

| | Compound | | | | | | | |
|---|---|---|---|---|---|---|---|---|
| Solvent | nC$_{12}$ | DBT sulfoxide | DBT sulfone | DBT Activity Coefficient | Thiophene Sulfoxide | Thiophene sulfone | Thiophene | Toluene |
| Water 90 W % Acetonitrile 5 W % Formic acid 5 W % | 1.79E+07 | 22.90 | 580.10 | 2.11E+04 | 0.80 | 16.20 | 250.60 | 1435.10 |
| Water 80 W % Acetonitrile 10 W % Formic acid 10 W % | 1.92E+06 | 5.30 | 125.10 | 2480.70 | 0.40 | 8.20 | 72.20 | 369.10 |
| Water 70 W % Acetonitrile 15 W % Formic acid 15 W % | 4.13E+05 | 1.90 | 43.20 | 581.30 | 0.30 | 5.10 | 30.80 | 144.80 |
| Water 60 W % Acetonitrile 20 W % Formic acid 20 W % | 1.35E+05 | 0.90 | 19.90 | 204.70 | 0.20 | 3.60 | 16.60 | 73.20 |
| Water 50 W % Acetonitrile 25 W % Formic acid 25 W % | 5.79E+04 | 0.50 | 11.10 | 93.40 | 0.20 | 2.70 | 10.40 | 43.50 |
| Water 40 W % Acetonitrile 30 W % Formic acid 30 W % | 2.98E+04 | 0.30 | 7.10 | 50.80 | 0.10 | 2.20 | 7.20 | 29.00 |

Figure 23:
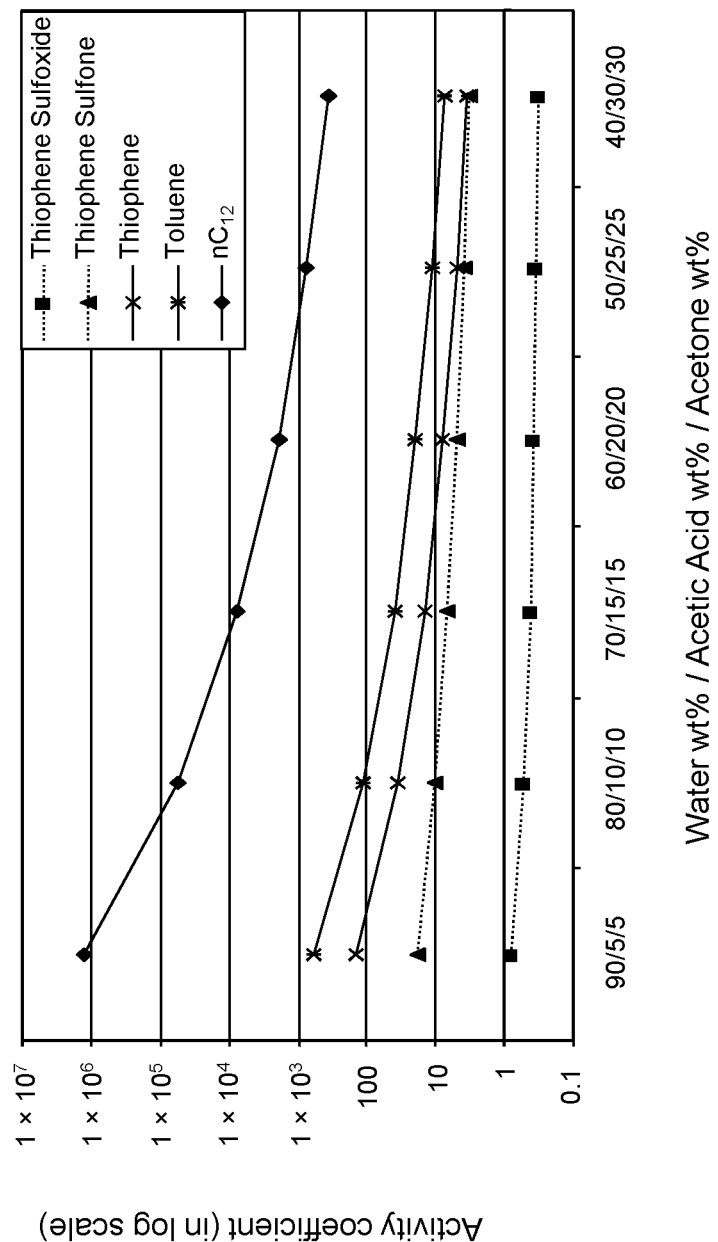
FIGS. 23 and 24 are plots of computational models of the activity coefficient values for a range of concentrations of an acetic acid/acetone aqueous solvent formulation for sulfoxidation products of thiophene and DBT, respectively, relative to other components in a hydrocarbon mixture.
Figure 24:
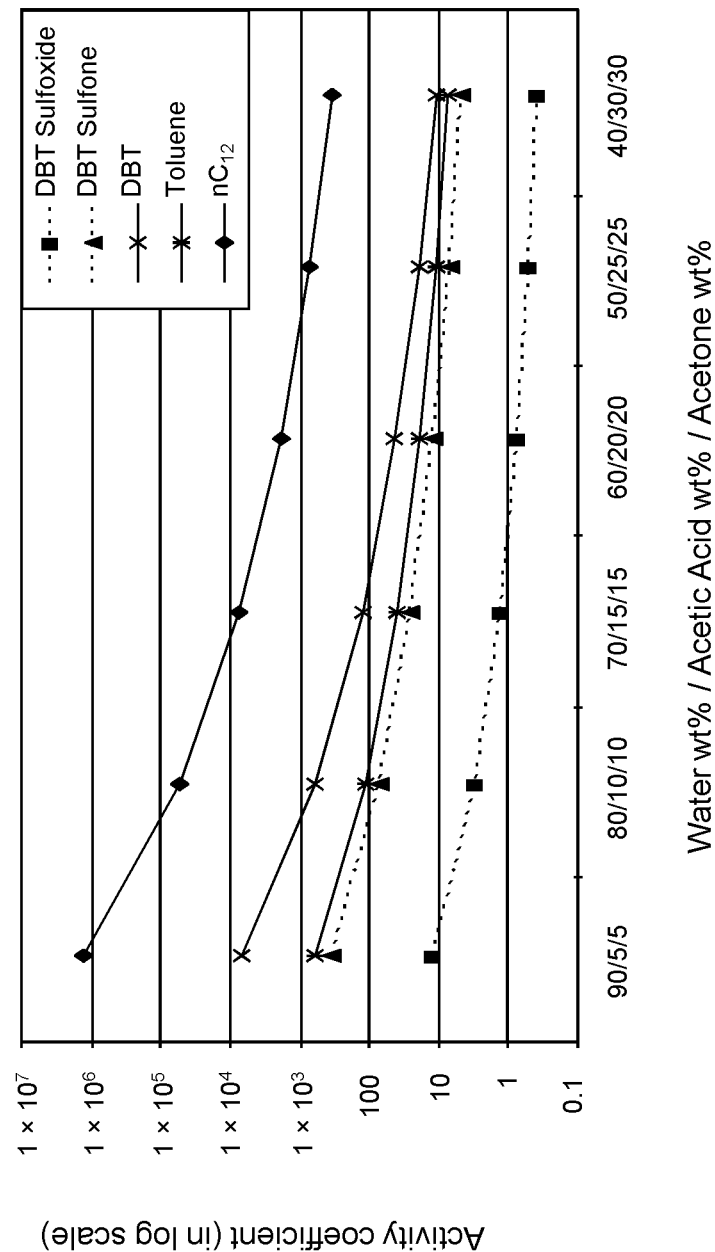

In still another embodiment of the process described herein, the solvent formulation comprises an aqueous solution of acetic acid and acetone. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. In an extractive simulation, COSMO-RS software was used to simulate γ for selective extraction of oxidized model A fuel by solvent formulations of aqueous acetic acid and acetone. Table 8A illustrates the activity coefficient of different concentrations of aqueous acetic acid/acetone. Based on the activity coefficient values in Table 8A, a useful aqueous acetic acid/acetone selective solvent formulation has a concentration of 10 W % acetic acid, 10 W % acetone and 80 W % water for extraction of thiophene sulfoxide and sulfone, as shown in FIG. 23. It is also apparent from FIG. 24 and the data in Table 8A that a suitable concentration of 20 W % acetic acid, 20 W % acetone and 60 W % water for extraction for extraction of DBT sulfoxide combined with DBT sulfone is effective.

TABLE 8A

| | Compound | | | | | | | |
|---|---|---|---|---|---|---|---|---|
| Solvent | $nC_{12}$ | DBT sulfoxide | DBT sulfone | DBT Activity Coefficient | Thiophene Sulfoxide | Thiophene sulfone | Thiophene | Toluene |
| Water 90 W % Acetic Acid 5 W % Acetone 5 W % | 1.29E+06 | 12.30 | 330.70 | 6889.30 | 0.80 | 17.50 | 145.90 | 586.00 |
| Water 80 W % Acetic Acid 10 W % Acetone 10 W % | 5.27E+04 | 2.90 | 68.30 | 586.40 | 0.50 | 10.00 | 36.00 | 112.60 |
| Water 70 W % Acetic Acid 15 W % Acetone 15 W % | 7299.10 | 1.30 | 24.40 | 123.90 | 0.40 | 6.60 | 14.70 | 39.40 |
| Water 60 W % Acetic Acid 20 W % Acetone 20 W % | 1923.60 | 0.70 | 11.80 | 42.80 | 0.40 | 4.80 | 7.80 | 19.10 |
| Water 50 W % Acetic Acid 25 W % Acetone 25 W % | 731.30 | 0.50 | 6.90 | 19.70 | 0.30 | 3.70 | 4.90 | 11.20 |
| Water 40 W % Acetic Acid 30 W % Acetone 30 W % | 350.40 | 0.40 | 4.50 | 10.90 | 0.30 | 3.10 | 3.50 | 7.40 |

Figure 25:
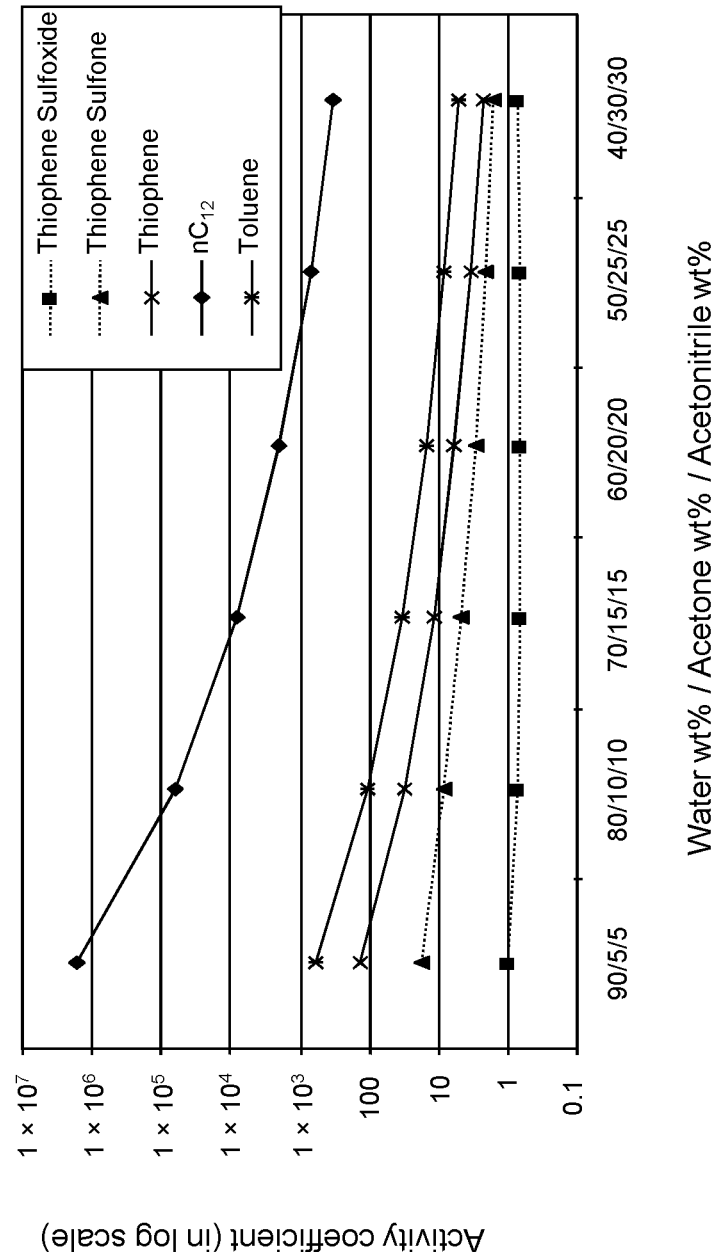
FIGS. 25 and 26 are plots of computational models of the activity coefficient values for a range of concentrations of an acetonitrile/acetone aqueous solvent formulation for sulfoxidation products of thiophene and DBT, respectively, relative to other components in a hydrocarbon mixture.
Figure 26:
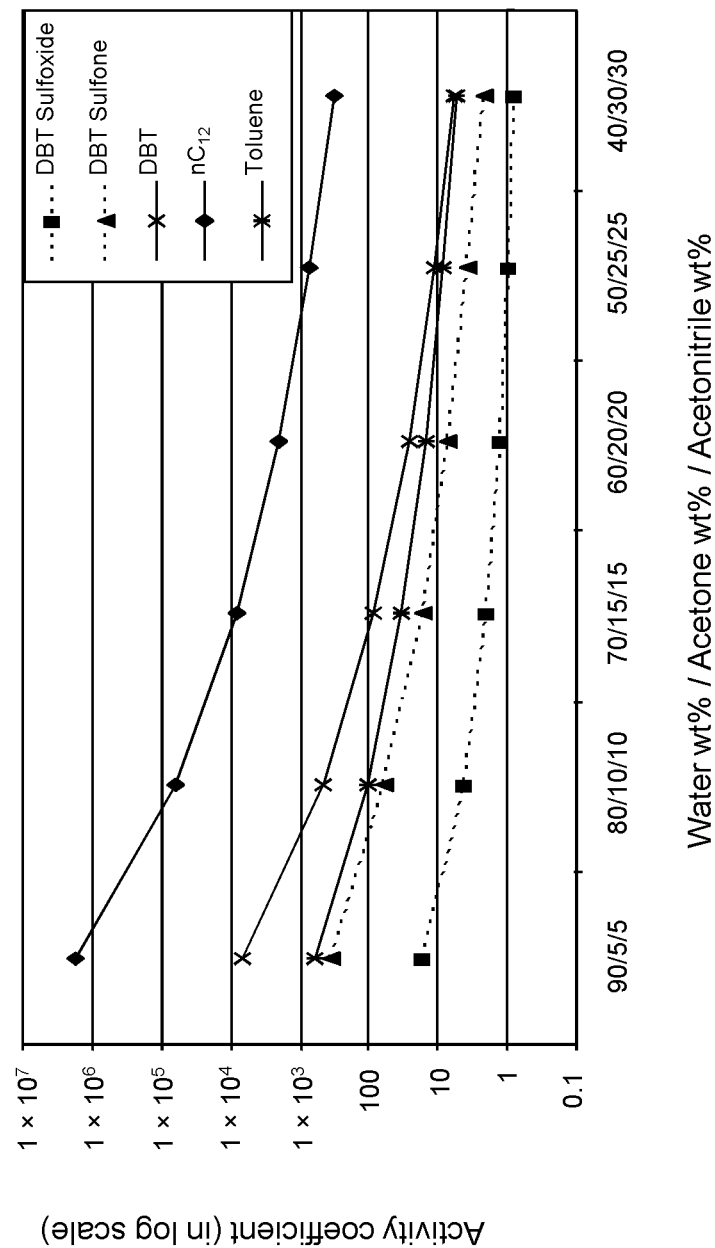

In yet a further embodiment of the process described herein, the solvent formulation comprises an aqueous solution of acetonitrile and acetone. The level of extraction and the specific concentration of the selective solvent formulation depend on factors including, but not limited to the sulfur speciation of the feed hydrocarbon mixture and whether the target sulfoxide products or sulfoxidation products to be extracted are non-bulky or bulky. In an extractive simulation. COSMO-RS software was used to simulate γ for selective extraction of oxidized model A fuel by solvent formulations of aqueous acetonitrile and acetone. Table 9A illustrates the activity coefficient of different concentrations of aqueous acetone/acetonitrile. Based on the activity coefficient values in Table 9A and FIGS. 25 and 26, aqueous acetone/acetonitrile selective solvent formulations are useful for extraction of sulfoxides, and extraction of sulfones is possible with concentration adjustments.

TABLE 9A

| | Compound | | | | | | | |
|---|---|---|---|---|---|---|---|---|
| Solvent | $nC_{12}$ | DBT sulfoxide | DBT sulfone | DBT Activity Coefficient | Thiophene Sulfoxide | Thiophene sulfone | Thiophene | Toluene |
| Water 90 W % Acetonitrile 5 W % Acetone 5 W % | 1.71E+06 | 16.40 | 334.60 | 6452.90 | 1.00 | 16.80 | 139.50 | 588.60 |
| Water 80 W % Acetonitrile 10 W % Acetone 10 W % | 6.43E+04 | 4.10 | 56.70 | 456.00 | 0.70 | 8.20 | 30.80 | 101.90 |
| Water 70 W % Acetonitrile 15 W % Acetone 15 W % | 8164.20 | 1.90 | 16.90 | 83.70 | 0.70 | 4.60 | 11.50 | 32.80 |

TABLE 9A-continued

| Solvent | nC$_{12}$ | DBT sulfoxide | DBT sulfone | DBT Activity Coefficient | Thiophene Sulfoxide | Thiophene sulfone | Thiophene | Toluene |
|---|---|---|---|---|---|---|---|---|
| | | | | Compound | | | | |
| Water 60 W % Acetonitrile 20 W % Acetone 20 W % | 1981.00 | 1.20 | 7.00 | 25.90 | 0.60 | 3.00 | 5.80 | 14.90 |
| Water 50 W % Acetonitrile 25 W % Acetone 25 W % | 706.30 | 0.90 | 3.60 | 10.90 | 0.70 | 2.10 | 3.50 | 8.30 |
| Water 40 W % Acetonitrile 30 W % Acetone 30 W % | 322.40 | 0.70 | 2.10 | 5.70 | 0.70 | 1.60 | 2.30 | 5.30 |

EXAMPLES

Example 1

A quantity of 100 mL of a model diesel feed formed of xylene, DBT, DBT sulfoxide and DBT sulfone (with a total sulfur content of 1635 ppmw) was oxidized by 30 W % aqueous hydrogen peroxide at a temperature of 37° C. and at a pressure of 1 atmosphere for a period of 70 minutes with solid ZnO catalyst (1.2 g) and a ratio of oxidant (H$_2$O$_2$) to organic sulfur of 4:1 in acetic acid, about 10 mL. After the sold catalyst settled, the model diesel was removed for extraction of sulfoxidation products and removal of aqueous H$_2$O$_2$ using an embodiment of the selective solvent formulation of the present invention.

DBT sulfoxide and DBT sulfone were extracted using a selective solvent formulation of 50 W % aqueous acetic acid. Two batch extractions were sequentially conducted using a solvent-to-model diesel ratio of about 1:1 at a temperature of 23° C. and at a pressure of 1 atmosphere for a period of 2 minutes, during which the contents were stirred. Table 10A represents the abundance units as determined by gas chromatographic analysis. The total extraction of DBT sulfoxide and DBT sulfone was 95 W % and 55 W % respectively. Furthermore, the co-extraction of xylene was limited to 1.9 W % after both extractions, and the co-extraction of DBT (not oxidized) was limited to 13.2 W % after both extractions. The total sulfur measured by sulfur speciation (using an ANTEK Model 9000 analyzer commercially available from Antek Instruments, Inc., Houston, Tex. USA) determined that the overall sulfur content was reduced by 55 W % as shown at Table 10B.

TABLE 10A

| | Xylene (aromatic) | DBT (untreated sulfur) | DBT sulfoxide | DBT sulfone |
|---|---|---|---|---|
| Model diesel oxidized | 9283.7 | 24.44 | 24.02 | 25.09 |
| 1$^{st}$ extraction | 9155.2 | 22.09 | 7.81 | 19.15 |
| | (−1.4%) | (−9.6%) | (−67.5%) | (−23.7%) |
| 2$^{nd}$ extraction | 9108.19 | 21.22 | 1.26 | 11.39 |
| | (−1.9%) | (−13.2%) | (−94.8%) | (−54.8%) |

TABLE 10B

| Sample ID | Total Sulfur, ppm |
|---|---|
| Model diesel reference | 1635 |
| Oxidize model diesel (reference) | 1694 |

TABLE 10B-continued

| Sample ID | Total Sulfur, ppm |
|---|---|
| 1$^{st}$ extraction | 1110 |
| | (−32%) |
| 2$^{nd}$ extraction | 740 |
| | (−55%) |

Example 2

A quantity of oxidized model diesel feed as used in Example 1 was subjected to extraction to remove DBT sulfoxide and DBT sulfone using a selective solvent formulation of 70 W % aqueous formic acid. Two batch extractions were sequentially conducted using a solvent to model diesel ratio of about 1:1 at a temperature of 23° C. and at a pressure of 1 atmosphere for a period of 2 minutes, during which the contents were stirred. Table 11A represents the abundance units as a result of gas chromatography. The total extraction of DBT sulfoxide and DBT sulfone was 94 W % and 56 W % respectively. Furthermore, the co-extraction of xylene was limited to 2 W % after the first extraction, and increased by 3.8 W % after the second extraction, based on the normalization percentage of the peak regions for the GC analysis for each extraction. The normalization method is qualitative and quasi-quantitative, so that the peak area varies. The slight positive (3.8%) of xylene is due to the normalization of the sum of all peaks and it was changed by material balance variation and/or with measurement error.

The co-extraction of DBT (not oxidized) was limited to 10 W % after both extractions. The total sulfur measured by sulfur speciation determined that the overall sulfur content was reduced by 56 W % as shown in Table 11B.

TABLE 11A

| | Xylene (aromatic) | DBT (untreated sulfur) | DBT sulfoxide | DBT sulfone |
|---|---|---|---|---|
| Model diesel oxidized | 9283.7 | 24.44 | 24.02 | 25.09 |
| 1$^{st}$ extraction | 9111.6 | 21.89 | 6.45 | 17.46 |
| | (−1.9%) | (−10.4%) | (−73.1%) | (−30.4%) |
| 2$^{nd}$ extraction | 9635.5 | 22 | 1.38 | 11.14 |
| | (+3.8%) | (−10.0%) | (−94%) | (−55.6%) |

TABLE 11B

| Sample ID | Total Sulfur, ppm |
| --- | --- |
| Model diesel reference | 1635 |
| Oxidize model diesel (reference) | 1694 |
| $1^{st}$ extraction | 960 |
| | (−41%) |
| $2^{nd}$ extraction | 720 |
| | (−56%) |

Example 3

A quantity of oxidized model diesel feed as used in Example 1 was subjected to extraction to remove DBT sulfoxide and DBT sulfone using a selective solvent formulation of 50 W % aqueous methanol. One extraction was conducted using a solvent to model diesel ratio of about 1:1 at a temperature of 23° C. and at a pressure of 1 atmosphere for a period of 2 minutes, during which the contents were stirred. Table 12A represents the abundance units as a result of gas chromatography. The total extraction of DBT sulfoxide was 51.5 W %. Furthermore, there was no co-extraction of xylene, as the amount of xylene increased by 2.8 W % after extraction (based on the normalized GC results). The co-extraction of DBT (not oxidized) was limited to 3.1 W %. The total sulfur measured by sulfur speciation determined that the overall sulfur content was reduced by 16 W % as shown at Table 12B.

TABLE 12A

| | Xylene (aromatic) | DBT (untreated sulfur) | DBT sulfoxide | DBT sulfone |
| --- | --- | --- | --- | --- |
| Model diesel oxidized | 9283.7 | 24.44 | 24.02 | 25.09 |
| $1^{st}$ extraction | 9540.4 | 23.69 | 11.64 | 24.49 |
| | +2.8%) | (−3.1%) | (−51.5%) | (−2.4%) |

TABLE 12B

| Sample ID | Total Sulfur, ppm |
| --- | --- |
| Model diesel reference | 1635 |
| Oxidize model diesel (reference) | 1694 |
| $1^{st}$ extraction | 1376 |
| | (−16%) |

Example 4

A quantity of 60 mL of straight run diesel from a refinery that contained about 7600 ppm sulfur was oxidized by 10 g 30 W % hydrogen peroxide and 20 g acetic acid at mild temperature (35° C.) for 4 hours to generate sulfoxide and sulfones of organic sulfur in diesel.

The oxidized diesel was extracted twice at ratio of 1:2 solvent to diesel of each batch extraction. The total sulfur content was measured by sulfur speciation (using an ANTEK Model 9000 analyzer) after oxidative desulfurization treatment.

After the first batch extraction using 30 ml 50 W % acetic acid, the total sulfur was decreased from 7600 ppm to 5402 ppm (28.9 W %) and the total reduction of diesel volume was 3 mL (5 volume % or V %). After the second batch extraction using 30 ml 50 W % acetic acid, the total sulfur after both extractions was decreased to 4875 ppm (36 W %) and the total reduction of diesel volume after both extractions was 3.5 mL (6 V %).

Example 5

A quantity of 60 mL of straight run diesel from a refinery that contained about 7600 ppm sulfur was oxidized by 5 g 30 W % hydrogen peroxide and 20 g acetic acid at mild temperature (35° C.) for 7 hours to generate sulfoxide and sulfones of organic sulfur in diesel.

The oxidized diesel was extracted twice at ratio of 1:2 solvent to diesel of each batch extraction. The total sulfur content was measured by sulfur speciation (using an ANTEK Model 9000 analyzer) after oxidative desulfurization treatment.

After the first batch extraction using 30 ml 50 W % acetic acid, the total sulfur was decreased from 7600 ppm to 4957 ppm (34.8 W %) and the total reduction of diesel volume was 3 mL (5 V %). After the second batch extraction using 30 ml 50 W % acetic acid, the total sulfur after both extractions was decreased to 4426 ppm (42 W %) and the total reduction of diesel volume after both extractions was 3.5 mL (6 V %).

Example 6

A quantity of 60 mL of straight run diesel from a refinery that contained about 7600 ppm sulfur was oxidized by 10 g 30 W % hydrogen peroxide and 20 g 85 W % formic acid at mild temperature (35° C.) for 4 hours to generate sulfoxide and sulfones of organic sulfur in diesel.

The oxidized diesel was extracted twice at ratio of 1:2 solvent to diesel of each batch extraction. The total sulfur content was measured by sulfur speciation (using an ANTEK Model 9000 analyzer) after oxidative desulfurization treatment.

After the first batch extraction using 30 ml 50 W % acetic acid, the total sulfur was decreased from 7600 ppm to 4941 ppm (35 W %) and the total reduction of diesel volume was 3 mL (5 V %). After the second batch extraction using 30 ml 50 W % acetic acid, the total sulfur after both extractions was decreased to 4322 ppm (43 W %) and the total reduction of diesel volume after both extractions was 3.5 mL (6 V %).

Example 7

A quantity of 50 mL of a straight run diesel was tested for the total acid number using the testing standards set forth under ASTM D664, before and after sulfoxidation treatment. The total acid number of the diesel before oxidation was 0.084 mg KOH/g. The diesel was oxidized according to the procedure described in Example 4. The oxidized sulfur components from the diesel feed were extracted by a 50 W % aqueous acetic acid selective solvent formulation, followed by water polishing. The sulfoxides combined with sulfones were extracted. The total acid number of diesel after oxidation and extraction was 0.024 mg KOH/g. The tests in Example 7 indicate that the acid number is lower after extraction with the acetic acid formulation followed by water polishing as compared to the original diesel feed.

The method and system of the present invention have been described in the above description, examples and in the attached drawings; however, modifications will be apparent to those of ordinary skill in the art and the scope of protection for the invention is to be defined by the claims that follow.

We claim:

1. An oxidative desulfurization process comprising:
reactively sulfoxidating a hydrocarbon fraction containing organosulfur compounds to produce a hydrocarbon mixture containing product components, and by-product sulfoxides or a combination of sulfoxides and sulfones;
contacting the mixture with a selective solvent formulation at a temperature in the range of about 0° C. to about 40° C.; and
recovering a hydrocarbon product of reduced sulfur content,
wherein the selective solvent formulation is determined by
qualitatively analyzing the hydrocarbon mixture to determine the composition including the type of sulfoxidation reaction products, the type of aromatic hydrocarbons and the type of non-aromatic hydrocarbons;
selecting as target sulfoxidation reaction products one or more sulfoxides or a combination of one or more sulfoxides and one or more sulfones;
determining the activity coefficient γ of a range of extraction solvent compositions for the target sulfoxidation reaction products and at least one type of aromatic or non-aromatic hydrocarbon in the hydrocarbon fraction, the extraction solvent compositions within the range of extraction solvent compositions comprising an aqueous solution having a concentration of about 2.5 weight % to about 70 weight % by weight polar organic solvent in water, the polar organic solvent selected from the group consisting of acetic acid, formic acid and combinations comprising acetic acid or formic acid; and
selecting, as the selective solvent formulation, an extraction solvent composition having an activity coefficient of less than about 16.5 for the target sulfoxidation reaction products that maximizes extraction of the target sulfoxidation reaction product, and an activity coefficient equal to or greater than about 16.5 for the at least one type of aromatic or non-aromatic hydrocarbon that minimizes co-extraction of the at least one type of aromatic or non-aromatic hydrocarbon.

2. The process as in claim 1, wherein the concentration of the aqueous solution is about 2.5 weight % to about 20 weight % of acetic acid, and wherein the target compounds for extraction are non-bulky sulfoxide products.

3. The process as in claim 1, wherein the concentration of the aqueous solution is about 20 weight % to about 40 weight % of acetic acid, and wherein the target compounds for extraction are bulky sulfoxide products.

4. The process as in claim 1, wherein the concentration of the aqueous solution is about 5 weight % to about 20 weight % of formic acid, and wherein the target compounds for extraction are non-bulky sulfoxide products.

5. The process as in claim 1, wherein the concentration of the aqueous solution is about 5 weight % to about 30 weight % of acetonitrile and about 5 weight % to about 30 weight % of formic acid.

6. The process as in claim 1, wherein the concentration of the aqueous solution is about 5 weight % to about 30 weight % of acetic acid and about 5 weight % to about 30 weight % of acetone.

7. The process as in claim 1, wherein the concentration of the aqueous solution is about 20 weight % to about 40 weight % of formic acid, and wherein the target compounds for extraction include 4,6-dimethyldibenzothiophene oxide.

8. The process as in claim 1, wherein the concentration of the aqueous solution is about 10 weight % to about 30 weight % of acetic acid, and wherein the target compounds for extraction include thiophene sulfide and thiophene sulfone.

9. The process as in claim 1, wherein the concentration of the aqueous solution is about 30 weight % to about 40 weight % of formic acid, and wherein the target compounds for extraction include thiophene sulfide and thiophene sulfone.

10. The process as in claim 1, wherein reactively sulfoxidating a hydrocarbon fraction is effected by an oxidation process selected from the group consisting of photooxidation, photochemical oxidation, ozonation, ionic liquid oxidation, electro chemical oxidation, bio-desulfurization, oxidation by hydrogen peroxide, oxidation by organic peracid, oxidation by peroxomonophosphoric acid, oxidation by nitrogen oxides, oxidation by nitric acid, and a combination of any of the foregoing oxidation processes.

11. An oxidative desulfurization process comprising:
reactively sulfoxidating a hydrocarbon fraction containing organosulfur compounds to produce a hydrocarbon mixture containing product components, and by-product sulfoxides or a combination of sulfoxides and sulfones;
contacting the mixture with a selective solvent formulation at a temperature in the range of about 0° C. to about 40° C.; and
recovering a hydrocarbon product of reduced sulfur content,
wherein the selective solvent formulation is an aqueous solution determined by selecting as target sulfoxidation reaction products one or more sulfoxides or a combination of one or more sulfoxides and one or more sulfones, and wherein the aqueous solution is selected from the group consisting of
about 2.5 weight % to about 20 weight % of acetic acid and wherein the target compounds for extraction are non-bulky sulfoxide products,
about 20 weight % to about 40 weight % of acetic acid and wherein the target compounds for extraction are bulky sulfoxide products,
about 5 weight % to about 20 weight % of formic acid, and wherein the target compounds for extraction are non-bulky sulfoxide products,
about 5 weight % to about 30 weight % of acetonitrile and about 5 weight % to about 30 weight % of formic acid and wherein the target compounds for extraction are a combination of 1 or more sulfoxides and 1 or more sulfones,
about 5 weight % to about 30 weight % of acetic acid and about 5 weight % to about 30 weight % of acetone and wherein the target compounds for extraction are a combination of 1 or more sulfoxides and 1 or more sulfones,
about 20 weight % to about 40 weight % of formic acid and wherein the target compounds for extraction include 4,6-dimethyldibenzothiophene oxide,
about 10 weight % to about 30 weight % of acetic acid and wherein the target compounds for extraction include thiophene sulfide and thiophene sulfone, and
about 30 weight % to about 40 weight % of formic acid and wherein the target compounds for extraction include thiophene sulfide and thiophene sulfone.

* * * * *